United States Patent
Li et al.

(10) Patent No.: US 11,421,010 B2
(45) Date of Patent: Aug. 23, 2022

(54) T CELLS EXPRESSING MEMBRANE-ANCHORED IL-12 FOR THE TREATMENT OF CANCER

(71) Applicant: Board of Regents, The University of Texas System, Austin, TX (US)

(72) Inventors: Shulin Li, Houston, TX (US); Jiemiao Hu, Houston, TX (US); Xueqing Xia, Houston, TX (US)

(73) Assignee: Board of Regents, The University of Texas System, Austin, TX (US)

(*) Notice: Subject to any disclaimer, the term of this patent is extended or adjusted under 35 U.S.C. 154(b) by 450 days.

(21) Appl. No.: 16/339,691

(22) PCT Filed: Oct. 6, 2017

(86) PCT No.: PCT/US2017/055645
§ 371 (c)(1),
(2) Date: Apr. 4, 2019

(87) PCT Pub. No.: WO2018/068008
PCT Pub. Date: Apr. 12, 2018

(65) Prior Publication Data
US 2020/0048322 A1 Feb. 13, 2020

Related U.S. Application Data

(60) Provisional application No. 62/405,796, filed on Oct. 7, 2016.

(51) Int. Cl.
| | | |
|---|---|---|
| *C07K 14/54* | (2006.01) | |
| *A61P 35/00* | (2006.01) | |
| *A61K 31/675* | (2006.01) | |
| *A61K 31/704* | (2006.01) | |
| *A61K 31/7076* | (2006.01) | |
| *A61K 35/17* | (2015.01) | |
| *A61K 38/20* | (2006.01) | |
| *C12N 5/0783* | (2010.01) | |
| *C12N 7/00* | (2006.01) | |
| *C12N 15/86* | (2006.01) | |

(52) U.S. Cl.
CPC ........ *C07K 14/5434* (2013.01); *A61K 31/675* (2013.01); *A61K 31/704* (2013.01); *A61K 31/7076* (2013.01); *A61K 35/17* (2013.01); *A61K 38/208* (2013.01); *A61P 35/00* (2018.01); *C12N 5/0636* (2013.01); *C12N 7/00* (2013.01); *C12N 15/86* (2013.01); *C07K 2319/03* (2013.01); *C12N 2501/998* (2013.01); *C12N 2740/15043* (2013.01)

(58) Field of Classification Search
CPC .............................. C07K 14/5434; A61P 35/00
See application file for complete search history.

(56) References Cited

U.S. PATENT DOCUMENTS

| | | |
|---|---|---|
| 9,657,077 B2 | 5/2017 | Li et al. |
| 2007/0014761 A1 | 1/2007 | West et al. |
| 2007/0122380 A1 | 5/2007 | Goldschneider et al. |
| 2013/0052663 A1 | 2/2013 | De Smedt et al. |
| 2017/0291934 A1 | 10/2017 | Reed et al. |

FOREIGN PATENT DOCUMENTS

| | | | |
|---|---|---|---|
| EP | 1418184 | 5/2004 | |
| WO | WO96/24676 | * 8/1996 | ............ C12N 15/62 |
| WO | WO2016/048903 | * 3/2016 | ............ C07K 14/54 |
| WO | WO 2016/048903 | 3/2016 | |
| WO | WO 2017/062953 | 4/2017 | |
| WO | WO 2018/068008 | 4/2018 | |
| WO | WO 2018/165228 | 9/2018 | |
| WO | WO 2018/213731 | 11/2018 | |
| WO | WO 2020/160350 | 8/2020 | |

OTHER PUBLICATIONS

Chinnasamy et al. (Clin Cancer Res; 18(6); 1672-83 [2012]). (Year: 2012).*
Fine et al. (Cellular Immunology 19 1, 49-59 ( 1999)). (Year: 1999).*
Wen-Xue Ma et al. "Cloning of transmembrane domain sequence of EGFR gene" Zhejiang Da Xue Xue Bao Yi Xue Ban. (Aug. 2002);31(4):235-238. (Year: 2002).*
Weinstein-Marom et al. (J Immunother 2016; 39:60-70) (Year: 2016).*
Cutrera et al., "Discovery of a Linear Peptide for Improving Tumor Targeting of Gene Products and Treatment of Distal Tumors by IL-12 Gene Therapy," *Mol Ther.*, 19(8):1468-1477, 2011.
Dudley et al., "Adoptive cell transfer therapy following non-myeloablative but lymphodepleting chemotherapy for the treatment of patients with refractory metastatic melanoma," *J Clin Oncol.*, 23(10):2346-2357, 2005.
Extended European Search Report issued in European Application No. 17859294.5, dated May 18, 2020.
Gambotto et al., "Induction of Antitumor Immunity by Direct Intratumoral Injection of a Recombinant Adenovirus Vector Expressing interleukin-12," *Cancer Gene Therapy*, 6(1):45-53, 1999.
Hu et al., "CD8+T Cell-Specific Induction of NKG2D Receptor by Doxorubicin Plus interleukin-12 and Its Contribution to CD8+T Cell Accumulation in Tumors," *Molecular Cancer*, 13(1):34, 2014.
Pan et al., "Cancer Immunotherapy Using a Membrane-Bound interleukin-12 With B7-1 Transmembrane and Cytoplasmic Domains," *Molecular Therapy*, 20(5):927-937, 2012.

(Continued)

*Primary Examiner* — Scott Long
(74) *Attorney, Agent, or Firm* — Parker Highlander PLLC

(57) ABSTRACT

Provided herein are polypeptides comprising membrane-anchored IL-12. Also provided herein are T cells expressing the membrane-anchored IL-12. Further, methods of treating cancer comprising administering T cells expressing membrane-anchored IL-12 are provided herein. Also provided are combination treatments comprising T cells expressing membrane-anchored IL-12 and T cell chemoattractant-inducing chemokines. In addition, methods are provided for activating T cells to express NKG2D and methods of their use in the treatment of cancer.

34 Claims, 25 Drawing Sheets
Specification includes a Sequence Listing.

(56) References Cited

OTHER PUBLICATIONS

PCT International Search Report and Written Opinion issued in International Application No. PCT/US2017/055645, dated Feb. 22, 2018.

PCT International Search Report and Written Opinion issued in International Application No. PCT/US2020/016016, dated Apr. 8, 2020.

Preston et al., "The ratios of CD8+ T cells to CD4+CD25+ FOXP3+ and FOXP3− T cells correlate with poor clinical outcome in human serous ovarian cancer," *PLoS One*, 8(11):e80063, 2013.

Radvanyi et al., "Specific lymphocyte subsets predict response to adoptive cell therapy using expanded autologous tumor-infiltrating lymphocytes in metastatic melanoma patients," *Clin Cancer Res.*, 18(24):6758-6770, 2012.

Yang et al., "Mouse interleukin-12/FasTI: A Novel Bi-Functional Fusion Protein for Cancer immuno/gene Therapy," *International Journal of Oncology*, 48(6):2381-2386, 2016.

Zhang et al., "Interleukin-12 Improves Cytotoxicity of Natural Killer Cells via Upregulated Expression of NKG2D," *Hum Immunol.*, 69:490-500, 2008.

Zhang et al., "Tumor-Infiltrating Lymphocytes Genetically Engineered with an Inducible Gene Encoding Interleukin-12 for the Immunotherapy of Metastatic Melanoma," *Clin Can Res*, 21(10):2278-2288, 2015.

Zhao et al., "Structural Design of Engineered Costimulation Determines Tumor Rejection Kinetics and Persistence of Car T Cells," *Cancer Cell*, 28(4):415-428, 2015.

Zhu et al., "Doxorubicin Directs the Accumulation of interleukin-12 Induced IFN Gamma Into Tumors for Enhancing STAT1 Dependent Antitumor Effect," *Clin Cancer Res.*, 13:4252-4260, 2007.

Zhu et al., "Systemic IL-12 Gene Therapy for Treating Malignancy via Intramuscular Electroporation," *Methods Mol Biol.*, 423:327-337, 2008.

* cited by examiner

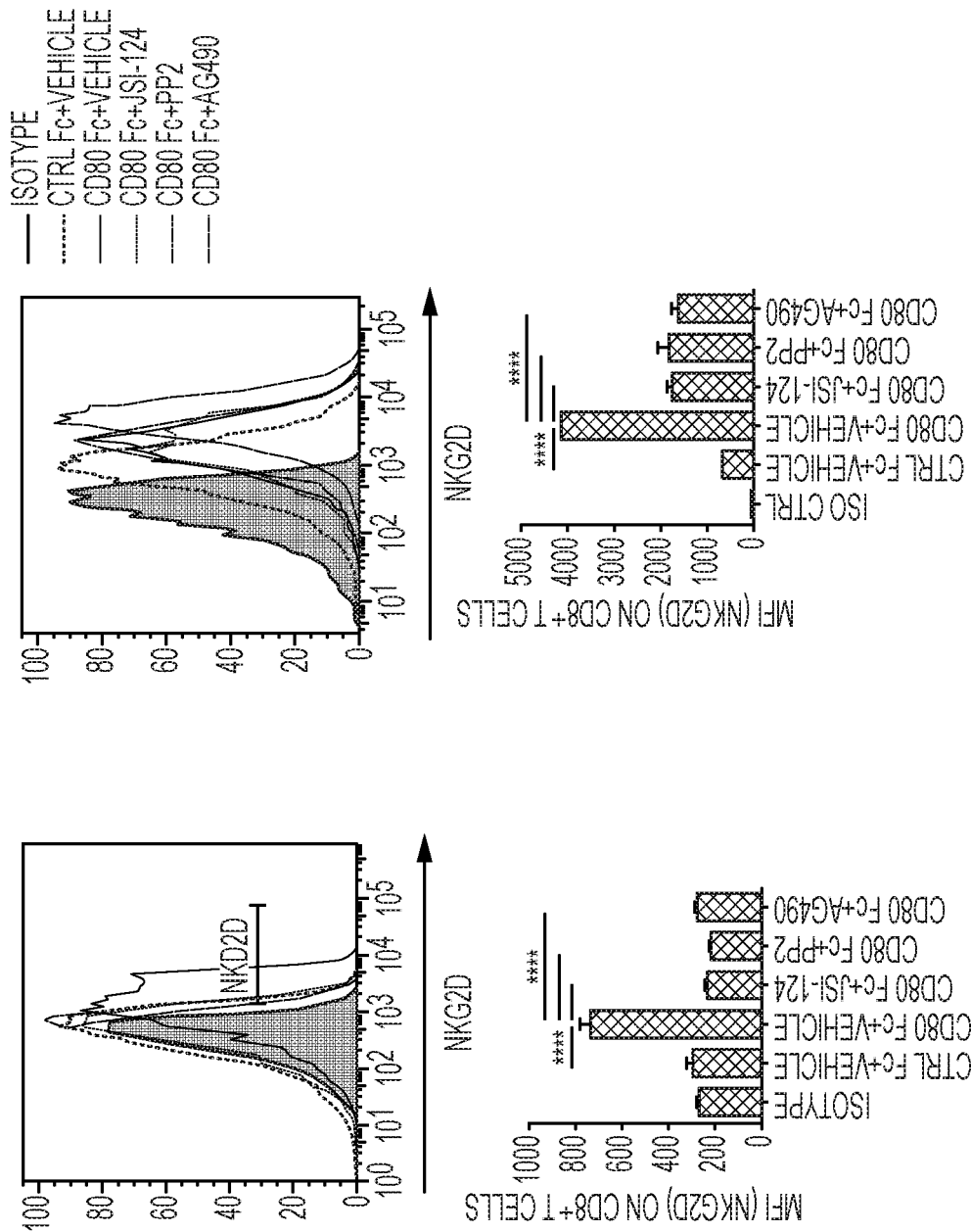

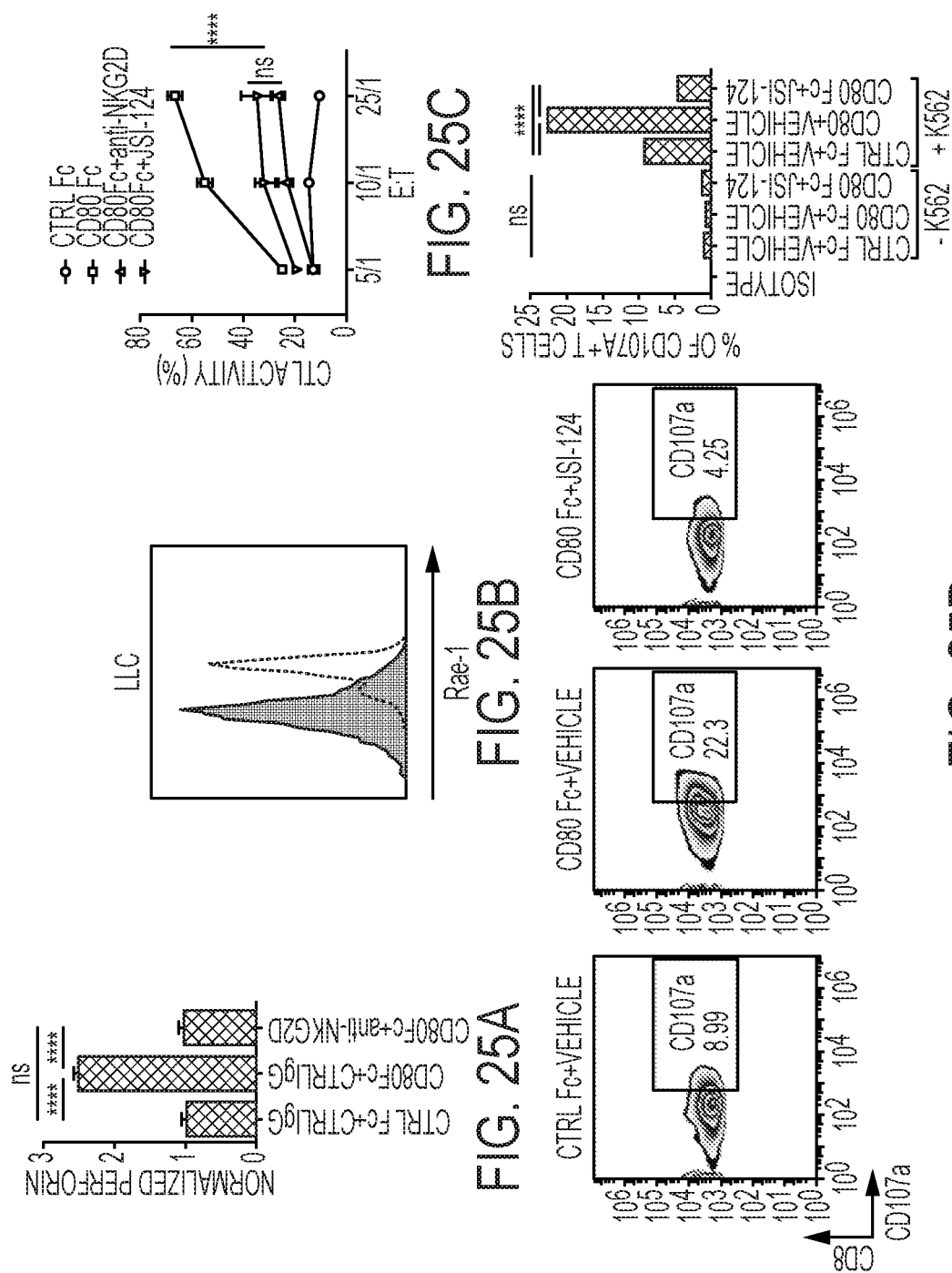

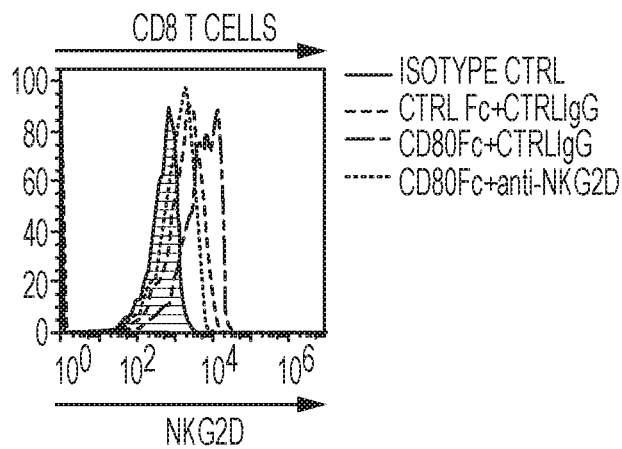
FIG. 26A
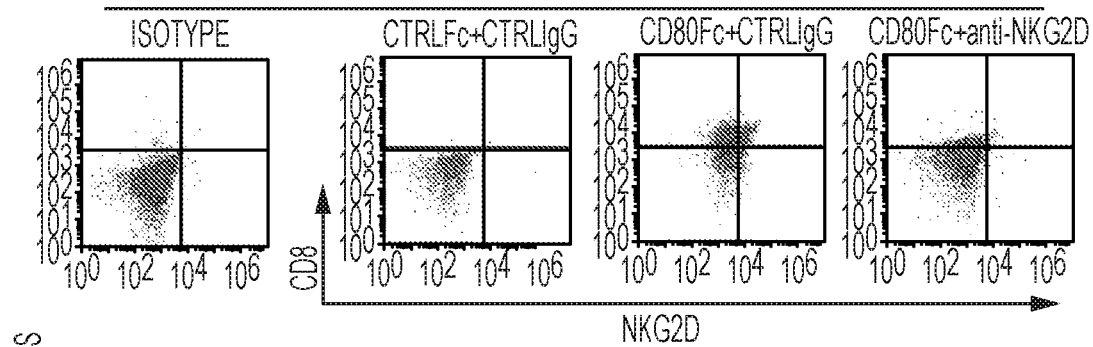
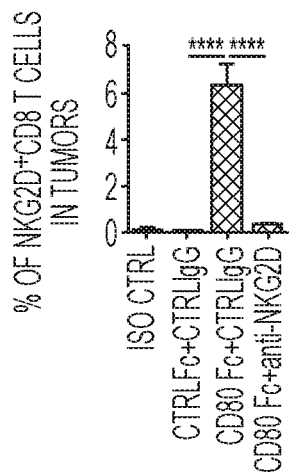
FIG. 26B
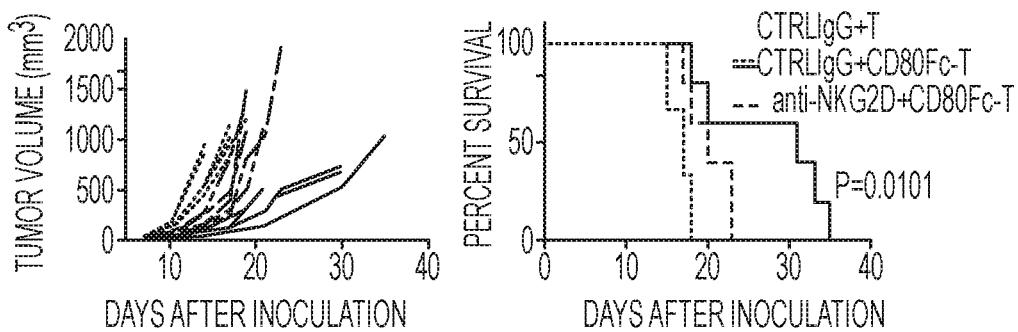
FIG. 26C

SEQUENCE LISTING

<160> NUMBER OF SEQ ID NOS: 7

<210> SEQ ID NO 1
<211> LENGTH: 306

<212> TYPE: PRT
<213> ORGANISM: Artificial Sequence
<220> FEATURE:
<223> OTHER INFORMATION: p35-TM fusion protein

<400> SEQUENCE: 1

Met Trp Pro Pro Gly Ser Ala Ser Gln Pro Pro Ser Pro Ala Ala
1               5                   10                  15

Ala Thr Gly Leu His Pro Ala Ala Arg Pro Val Ser Leu Gln Cys Arg
            20                  25                  30

Leu Ser Met Cys Pro Ala Arg Ser Leu Leu Leu Val Ala Thr Leu Val
            35                  40                  45

Leu Leu His Leu Ser Leu Ala Arg Asn Leu Pro Val Ala Thr Pro Asp
        50                  55                  60

Pro Gly Met Phe Pro Cys Leu His His Ser Gln Asn Leu Leu Arg Ala
65                  70                  75                  80

Val Ser Asn Met Leu Gln Lys Ala Arg Gln Thr Leu Glu Phe Tyr Pro
                85                  90                  95

Cys Thr Ser Glu Glu Ile Asp His Glu Asp Ile Thr Lys Asp Lys Thr
                100                 105                 110

Ser Thr Val Glu Ala Cys Leu Pro Leu Glu Leu Thr Lys Asn Glu Ser
            115                 120                 125

Cys Leu Asn Ser Arg Glu Thr Ser Phe Ile Thr Asn Gly Ser Cys Leu
130                 135                 140

Ala Ser Arg Lys Thr Ser Phe Met Met Ala Leu Cys Leu Ser Ser Ile
145                 150                 155                 160

Tyr Glu Asp Leu Lys Met Tyr Gln Val Glu Phe Lys Thr Met Asn Ala
                165                 170                 175

Lys Leu Leu Met Asp Pro Lys Arg Gln Ile Phe Leu Asp Gln Asn Met
            180                 185                 190

Leu Ala Val Ile Asp Glu Leu Met Gln Ala Leu Asn Phe Asn Ser Glu
        195                 200                 205

Thr Val Pro Gln Lys Ser Ser Leu Glu Glu Pro Asp Phe Tyr Lys Thr
    210                 215                 220

Lys Ile Lys Leu Cys Ile Leu Leu His Ala Phe Arg Ile Arg Ala Val
225                 230                 235                 240

Thr Ile Asp Arg Val Met Ser Tyr Leu Asn Ala Ser Gly Gly Gly Gly
                245                 250                 255

Ser Gly Gly Gly Gly Ser Ser Ile Ala Thr Gly Met Val Gly Ala Leu
            260                 265                 270

Leu Leu Leu Leu Val Val Ala Leu Gly Ile Gly Leu Phe Met Arg Arg
        275                 280                 285

Arg His Ile Val Arg Lys Arg Thr Leu Arg Arg Leu Leu Gln Glu Arg
    290                 295                 300

Glu Leu
305

<210> SEQ ID NO 2
<211> LENGTH: 251
<212> TYPE: PRT
<213> ORGANISM: Homo sapiens

<400> SEQUENCE: 2

Met Trp Pro Pro Gly Ser Ala Ser Gln Pro Pro Ser Pro Ala Ala
1               5                   10                  15

Ala Thr Gly Leu His Pro Ala Ala Arg Pro Val Ser Leu Gln Cys Arg

```
                    20                  25                  30

Leu Ser Met Cys Pro Ala Arg Ser Leu Leu Val Ala Thr Leu Val
            35                  40                  45

Leu Leu His Leu Ser Leu Ala Arg Asn Leu Pro Val Ala Thr Pro Asp
 50                  55                  60

Pro Gly Met Phe Pro Cys Leu His His Ser Gln Asn Leu Leu Arg Ala
 65                  70                  75                  80

Val Ser Asn Met Leu Gln Lys Ala Arg Gln Thr Leu Glu Phe Tyr Pro
                 85                  90                  95

Cys Thr Ser Glu Glu Ile Asp His Glu Asp Ile Thr Lys Asp Lys Thr
            100                 105                 110

Ser Thr Val Glu Ala Cys Leu Pro Leu Glu Leu Thr Lys Asn Glu Ser
            115                 120                 125

Cys Leu Asn Ser Arg Glu Thr Ser Phe Ile Thr Asn Gly Ser Cys Leu
            130                 135                 140

Ala Ser Arg Lys Thr Ser Phe Met Met Ala Leu Cys Leu Ser Ser Ile
145                 150                 155                 160

Tyr Glu Asp Leu Lys Met Tyr Gln Val Glu Phe Lys Thr Met Asn Ala
                165                 170                 175

Lys Leu Leu Met Asp Pro Lys Arg Gln Ile Phe Leu Asp Gln Asn Met
            180                 185                 190

Leu Ala Val Ile Asp Glu Leu Met Gln Ala Leu Asn Phe Asn Ser Glu
        195                 200                 205

Thr Val Pro Gln Lys Ser Ser Leu Glu Glu Pro Asp Phe Tyr Lys Thr
    210                 215                 220

Lys Ile Lys Leu Cys Ile Leu Leu His Ala Phe Arg Ile Arg Ala Val
225                 230                 235                 240

Thr Ile Asp Arg Val Met Ser Tyr Leu Asn Ala
                245                 250

<210> SEQ ID NO 3
<211> LENGTH: 43
<212> TYPE: PRT
<213> ORGANISM: Artificial Sequence
<220> FEATURE:
<223> OTHER INFORMATION: Transmembrane domain

<400> SEQUENCE: 3

Ile Ala Thr Gly Met Val Gly Ala Leu Leu Leu Leu Val Val Ala
1               5                  10                  15

Leu Gly Ile Gly Leu Phe Met Arg Arg Arg His Ile Val Arg Lys Arg
                20                  25                  30

Thr Leu Arg Arg Leu Leu Gln Glu Arg Glu Leu
        35                  40

<210> SEQ ID NO 4
<211> LENGTH: 328
<212> TYPE: PRT
<213> ORGANISM: Homo sapiens

<400> SEQUENCE: 4

Met Cys His Gln Gln Leu Val Ile Ser Trp Phe Ser Leu Val Phe Leu
1               5                  10                  15

Ala Ser Pro Leu Val Ala Ile Trp Glu Leu Lys Lys Asp Val Tyr Val
                20                  25                  30

Val Glu Leu Asp Trp Tyr Pro Asp Ala Pro Gly Glu Met Val Val Leu
            35                  40                  45
```

-continued

```
Thr Cys Asp Thr Pro Glu Glu Asp Gly Ile Thr Trp Thr Leu Asp Gln
 50                  55                  60

Ser Ser Glu Val Leu Gly Ser Gly Lys Thr Leu Thr Ile Gln Val Lys
 65                  70                  75                  80

Glu Phe Gly Asp Ala Gly Gln Tyr Thr Cys His Lys Gly Gly Glu Val
                 85                  90                  95

Leu Ser His Ser Leu Leu Leu Leu His Lys Glu Asp Gly Ile Trp
            100                 105                 110

Ser Thr Asp Ile Leu Lys Asp Gln Lys Glu Pro Lys Asn Lys Thr Phe
            115                 120                 125

Leu Arg Cys Glu Ala Lys Asn Tyr Ser Gly Arg Phe Thr Cys Trp Trp
130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
            195                 200                 205

Glu Val Met Val Asp Ala Val His Lys Leu Lys Tyr Glu Asn Tyr Thr
210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
            275                 280                 285

Val Phe Thr Asp Lys Thr Ser Ala Thr Val Ile Cys Arg Lys Asn Ala
290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
                325
```

<210> SEQ ID NO 5
<211> LENGTH: 11
<212> TYPE: PRT
<213> ORGANISM: Artificial Sequence
<220> FEATURE:
<223> OTHER INFORMATION: Linker

<400> SEQUENCE: 5

```
Gly Gly Gly Gly Ser Gly Gly Gly Gly Ser Ser
 1               5                   10
```

<210> SEQ ID NO 6
<211> LENGTH: 12
<212> TYPE: PRT
<213> ORGANISM: Artificial Sequence
<220> FEATURE:
<223> OTHER INFORMATION: Synthetic linker

<400> SEQUENCE: 6

Ser Gly Gly Gly Gly Ser Gly Gly Gly Gly Ser Ser

```
<210> SEQ ID NO 7
<211> LENGTH: 10
<212> TYPE: PRT
<213> ORGANISM: Artificial Sequence
<220> FEATURE:
<223> OTHER INFORMATION: Synthetic linker

<400> SEQUENCE: 7

Gly Gly Gly Gly Ser Gly Gly Gly Gly Ser
1               5                   10
```

T CELLS EXPRESSING MEMBRANE-ANCHORED IL-12 FOR THE TREATMENT OF CANCER

This application is a national phase application under 35 U.S.C. § 371 of International Application No. PCT/US2017/055645, which claims the benefit of U.S. Provisional Patent Application No. 62/405,796, filed Oct. 7, 2016, the entirety of each of which is incorporated herein by reference.

The sequence listing that is contained in the file named "UTFCP1302WO_ST25.txt", which is 9 KB (as measured in Microsoft Windows) and was created on Oct. 6, 2017, is filed herewith by electronic submission and is incorporated by reference herein.

BACKGROUND OF THE INVENTION

1. Field of the Invention

The present invention relates generally to the fields of immunology and medicine. More particularly, it concerns T cell therapies, such as with membrane-anchored IL-12, and use thereof for the treatment of cancer.

2. Description of Related Art

Autologous tumor-infiltrating lymphocyte (TIL) infusion has been a remarkable breakthrough in the treatment of patients with refractory melanoma and has resulted in higher response rates than has BRAF-targeted therapy or CTLA-4-blocking therapy. Most patients should experience a response to TIL transfer because TILs can be isolated from their tumors. However, in practice, the response rates are only about 50%, including a 10%-15% complete response rate (Besser et al., 2010; Radvanyi et al., 2012; Dudley et al., 2005).

Major challenges in TIL therapy are the reduced tumor homing ability of TILs after reinfusion as well as the changes in the tumor microenvironment. In recent clinical trials, $1.5\text{-}2\times10^{11}$ TILs were infused to ensure enough tumor-targeting TILs and successful tumor remission (Radvanyi et al., 2012; Dudley et al., 2005). However, transferring such large numbers of TILs into cancer patients can cause off-target adverse effects. Approaches are needed that enable TILs to be delivered to tumor sites more efficiently and therefore require much smaller numbers of infused T cells.

One critical reason that TILs cannot reach tumor sites is the loss of tumor homing characteristics during ex vivo culture; thus, new therapies use T cells that have been engineered with receptors that recognize tumor antigens (e.g., CD19), known as chimeric antigen receptor (CAR)-T cell therapy. CAR-T cell therapy more specifically targets tumor cells and has had substantial success in treating hematologic malignancies, in which CAR-T cells target tumor cells in the blood and bone marrow. However, the efficacy of CAR-T cell therapy is limited in solid tumors. Common antigens are lacking on solid tumor cells due to their heterogeneity. In addition, the host conditioning often avoids T cells entering the tumor stroma.

There are multiple challenges for using T cell therapy including CAR-T, TIL, and TCR-T (CTL) cells to treat solid tumors including tumor heterogeneity to escape the antigen or target specific T cell attack, T cell penetration into solid tumors, inactivation of the infiltrated T cells by the immune suppressive environment, and the exhaustion of effector T cells. Thus, there is an unmet need for T cell therapies that are able to penetrate deep into solid tumors.

SUMMARY OF THE INVENTION

In a first embodiment, the present disclosure provides a membrane-anchored interleukin 12 (IL-12) heterodimer protein comprising a first polypeptide comprising an IL-12 alpha subunit p35 (e.g., SEQ ID NO:2) or a polypeptide at least 90% similar thereto, a second polypeptide comprising an IL-12 beta subunit p40 (e.g., SEQ ID NO:41 or a polypeptide at least 90% similar thereto, and a transmembrane domain (TMD) fused to a terminus of the first polypeptide and/or the second polypeptide.

In some aspects, the first polypeptide is fused to the transmembrane domain. In particular aspects, the transmembrane domain is C-terminal to the first polypeptide. In some aspects, the transmembrane domain comprises a sequence at least 90% identical to SEQ ID NO:3. In certain aspects, the transmembrane domain comprises the amino acid sequence of SEQ ID NO:3.

In certain aspects, the first polypeptide is N-terminal to the second polypeptide. In other aspects, the first polypeptide is C-terminal to the second polypeptide. In one particular aspect, the protein comprises from N-terminal to C-terminal the first polypeptide, the transmembrane domain, and the second polypeptide. In other aspects, the protein comprises from N-terminal to C-terminal the second polypeptide, the transmembrane domain, and the first polypeptide. The first polypeptide, second polypeptide, TMD, and optionally a linker may be fused in various configurations. For example, the protein may comprise a configuration such as, but not limited to, p35-TMD-p40, p40-TMD-p35, p35-linker-TMD-p40, p40-linker-TMD-p35, p35-TMD-linker-p40, p40-TMD-linker-p35, TMD-p35-p40, TMD-p40-p35, p35-p40-TMD, or p40-p35-TMD.

In some aspects, the first polypeptide is an IL-12 alpha subunit p35 or a polypeptide at least 90% identical thereto and the second polypeptide is an IL-12 beta subunit p40 or a polypeptide at least 90% identical thereto.

In certain aspects, the protein further comprises a linker. In some aspects, the linker comprises the amino acid sequence GGGGSGGGGSS (SEQ ID NO:5). In some further aspects, the linker comprises the amino acid sequence SGGGGSGGGGSS (SEQ ID NO:6). In still further aspects, the linker comprises the amino acid sequence GGGGSGGGGS (SEQ ID NO:7). In particular aspects, the linker is between the IL-12 alpha subunit p35 and the transmembrane domain.

In some aspects, the first polypeptide comprises an amino acid sequence at least 90% similar to SEQ ID NO:1. In certain aspects, the first polypeptide comprises an amino acid sequence at least 90% identical to SEQ ID NO:1. In some aspects, the first polypeptide is at least 91%, 92%, 93%, 94%, 95% or 96% similar to SEQ ID NO:1. In particular aspects, the first polypeptide is at least 91%, 92%, 93%, 94%, 95% or 96% identical to SEQ ID NO:1.

In certain aspects, the second polypeptide comprises an amino acid sequence at least 90% similar to SEQ ID NO:4. In some aspects, the second polypeptide comprises an amino acid sequence at least 90% identical to SEQ ID NO:4. In some aspects, the second polypeptide is at least 91%, 92%, 93%, 94%, 95% or 96% similar to SEQ ID NO:4. In particular aspects, the second polypeptide is at least 91%, 92%, 93%, 94%, 95% or 96% identical to SEQ ID NO:4.

Further provided herein is a polynucleotide encoding the membrane-anchored IL-12 protein of the embodiments.

Also provided herein are expression vectors comprising the polynucleotide encoding the membrane-anchored IL-12. The expression vector may be a viral vector, such as a lentiviral vector, retroviral vector, adenoviral vector, or adeno-associated viral vector.

In another embodiment, there is provided a population of T cells engineered to express membrane-anchored IL-12 of the embodiments. In certain aspects, the T cells may express the expression vector of the embodiments, such as a viral vector encoding the membrane-anchored IL-12. In some aspects, the T cells are tumor infiltrating lymphocytes (TILs), CD8$^+$ T cells and/or CD4$^+$ T cells. In particular aspects, the T cells are CD8$^+$ T cells. In some aspects, the T cells are tumor-specific T cells. In some aspects, the T cells are further engineered to express a T cell receptor (TCR) or chimeric antigen receptor (CAR) having antigenic specificity for a tumor-associated antigen. In certain aspects, the (CAR) comprises an intracellular signaling domain, a transmembrane domain, and an extracellular domain comprising a tumor-associated antigen binding region. In some aspects, the antigen binding region is an F(ab')2, Fab', Fab, Fv, or scFv. In particular aspects, the intracellular signaling domain is a T-lymphocyte activation domain. In some aspects, the intracellular signaling domain comprises CD3ζ, CD28, OX40/CD134, 4-1BB/CD137, FcεRIγ, ICOS/CD278, ILRB/CD122, IL-2RG/CD132, DAP molecules, CD70, cytokine receptor, CD40, Toll-like receptor 9, or a combination thereof. In certain aspects, the transmembrane domain comprises CD28 transmembrane domain, IgG4Fc hinge, Fc regions, CD4 transmembrane domain, the CD3ξ transmembrane domain, cysteine mutated human CD3ξ domain, CD16 transmembrane domain, CD8 transmembrane domain, or erythropoietin receptor transmembrane domain.

A further embodiment provides a method for producing the population of T cells engineered to express membrane-anchored IL-12 comprising obtaining a starting population of T cells and introducing a vector expressing membrane-anchored IL-12, thereby generating a population of T cells expressing membrane-anchored IL-12. In certain aspects, the expression vector is a viral vector, such as a lentiviral vector. In some aspects, membrane-anchored IL-12 is under the control of two constitutive promoters, such as cytomegalovirus (CMV). In some aspects, introducing comprises performing electroporation. In further aspects, the T cells may be activated with anti-CD3 and CD80-FC recombinant protein. The T cells may be treated with the anti-CD3 (e.g., for about 1 day) prior to the CD80-Fc (e.g., for about 1-5 days, such as 4 days).

In yet another embodiment, there is provided a method of treating a cancer in a subject comprising administering an effective amount of T cells engineered to express membrane-anchored IL-12 of the embodiments to the subject. In some aspects, the subject is a human. In certain aspects, the T cells are autologous T cells. In certain aspects, the method further comprises lymphodepletion of the subject prior to administration of the T cells. In particular aspects, the cancer is colon cancer or lung cancer. In some aspects, the T cells and/or at least one additional therapy is administered more than once. In particular aspects, the T cells penetrate to or near the center of a tumor within the subject.

In some aspects, the T cells are engineered to express membrane-anchored IL-12 by lentiviral transduction. In specific aspects, there is low or essentially no T cell accumulation in the subject's lungs after administering the T cells engineered to express membrane-anchored IL-12. In certain aspects, lentiviral transduction results in a reduced risk of cytokine response syndrome (CRS), reduced systemic toxicity, and/or increased effectiveness of treatment.

In some aspects, lymphodepletion comprises administration of cyclophosphamide and/or fludarabine. In certain aspects, the method further comprises administering at least one additional therapeutic agent. In certain aspects, the at least one additional therapeutic agent is chemotherapy, immunotherapy, surgery, radiotherapy, or biotherapy. In some aspects, the chemotherapy is selected from the group consisting of cyclophosphamide, methotrexate, fluorouracil, doxorubicin, vincristine, ifosfamide, cisplatin, gemcytabine, busulfan, ara-C, and combinations thereof. In particular aspects, the chemotherapy is doxorubicin or cyclophosphamide. In some aspects, the chemotherapy is administered prior to the T cells. In certain aspects, the chemotherapy is administered 15 to 25 hours prior to the T cell therapy. In certain aspects, the T cells and/or at least one additional therapeutic agent is administered intravenously, intraperitoneally, intratracheally, intratumorally, intramuscularly, endoscopically, intralesionally, percutaneously, subcutaneously, regionally, or by direct injection or perfusion.

In certain aspects, administration of the T cells expressing membrane-anchored IL-12 does not induce IFNγ or induces a lower level of IFNγ as compared to administration of T cells with wild-type IL-12. In some aspects, the IFNγ is measured in a serum sample or in medium. In some aspects, the T cells induce expression of CXCL9, CXCL10 and/or CCL17. In some aspects, administering the T cells induces expression of NKG2D and/or NKG2D ligands. In certain aspects, the T cells induce expression of costimulatory receptor CD28. In some aspects, the T cells decrease expression of an immune checkpoint inhibitor. In particular aspects, the immune checkpoint inhibitor is PD-1 or PD-L1.

In another embodiment, there is provided an in vitro method for generating NKG2D-positive CD8$^+$ T cells comprising obtaining a starting population of T cells and culturing the starting population of T cells in the presence of anti-CD3 (e.g., anti-CD3 microbeads) and CD80 (e.g., CD80-Fc recombinant protein) for a period of time sufficient to induce NKG2D expression, thereby generating NKG2D$^+$ CD8$^+$ T cells. In some aspects, the culturing is further defined as pre-treating the starting population of T cells to anti-CD3 and then treating the T cells with CD80. In some aspects, the starting population of T cells are CD28-positive. In certain aspects, the starting population of T cells are TILs, CD8$^+$ T cells and/or CD4$^+$ T cells. In some aspects, the starting population of T cells are CD8$^+$ T cells. In certain aspects, pre-treating with anti-CD3 is for 12-48 hours, such as about 24 hours. In some aspects, culturing in the presence of CD80 is for 1-5 days, such as 1, 2, 3, 4, or 5 days. In some aspects, treating with CD80 results in phosphorylation of STAT3.

In some aspects, the T cells are further engineered to express a TCR or CAR having antigenic specificity for a tumor-associated antigen. In certain aspects, the CAR comprises an intracellular signaling domain, a transmembrane domain, and an extracellular domain comprising a tumor-associated antigen binding region. In certain aspects, the antigen binding region is an F(ab')2, Fab', Fab. Fv, or scFv. In some aspects, the intracellular signaling domain is a T-lymphocyte activation domain. In certain aspects, the intracellular signaling domain comprises CD3ξ, CD28, OX40/CD134, 4-1BB/CD137, FcεRIγ, ICOS/CD278, ILRB/CD122, IL-2RG/CD132. DAP molecules, CD70, cytokine receptor, CD40. Toll-like receptor 9, or a combination thereof. In certain aspects, the transmembrane domain comprises CD28 transmembrane domain, IgG4Fc hinge, Fc regions, CD4 transmembrane domain, the CD3ζ transmembrane domain, cysteine mutated human CD3ζ domain, CD16 transmembrane domain, CD8 transmembrane domain, or erythropoietin receptor transmembrane domain.

Further provided herein is a method of treating a cancer in a subject comprising administering an effective amount of NKG2D⁺CD8⁺ T cells of the embodiments to the subject. In further aspects, the T cells express membrane-anchored IL-12 of the embodiments, such as by lentiviral transduction of a lentiviral vector. In some aspects, the subject is a human. In certain aspects, the T cells are autologous T cells. In particular aspects, the cancer is colon cancer or lung cancer.

In additional aspects, the method further comprises administering at least one additional therapeutic agent. In some aspects, the at least one additional therapeutic agent is chemotherapy, immunotherapy, surgery, radiotherapy, or biotherapy. In certain aspects, the chemotherapy is selected from the group consisting of cyclophosphamide, methotrexate, fluorouracil, doxorubicin, vincristine, ifosfamide, cisplatin, gemcytabine, busulfan, ara-C, and combinations thereof. In some aspects, the chemotherapy is doxorubicin or cyclophosphamide. In particular aspects, the chemotherapy is administered prior to the T cells. In specific aspects, the chemotherapy is administered 15 to 25 hours prior to the T cell therapy. In some aspects, the T cells and/or at least one additional therapeutic agent is administered intravenously, intraperitoneally, intratracheally, intratumorally, intramuscularly, endoscopically, intralesionally, percutaneously, subcutaneously, regionally, or by direct injection or perfusion.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 24A-24B: Blockade of Lck/JAK/STAT3 signaling abolishes CD28 activation-mediated induction of NKG2D expression on mouse and human $CD8^+$ T cells. (A, B) Mouse (A) and human (B) $CD8^+$ T cells were stimulated with anti-CD3 microbeads and treated with control Fc or CD80-FC in the presence or absence of the pharmacologic inhibitor JSI-124, PP2, or AG-490 for 24 h. The CD80+ vehicle has the highest expression of NKG2D. NKG2D expression on the surface of $CD8^+$ T cells was measured using flow cytometry. The bar graphs show the median (±SEM) MFI of NKG2D (n=3). The data are representative of three repeated experiments.

FIGS. 25A-25D: Augmentation of $CD8^+$ T-cell antitumor cytolytic activity by treatment with CD80-Fc. (A-C) Induction of antitumor cytolytic activity by mouse $CD8^+$ T cells after exposure to Rae-$1^+$ LLC cells. Splenocytes were collected from LLC-bearing mice on day 14 after tumor-cell inoculation. $CD8^+$ T cells were isolated from splenocytes and treated with control Fc or CD80-Fc in the presence or absence of an anti-NKG2D antibody or JSI-124 for 24 h. (A) $CD8^+$ T cells were co-incubated with CFSE-labeled LLC cells at a ratio of 25:1 (E:T) for 5 h. The cell culture medium was subjected to ELISA analysis of perforin. The bar graphs show the median (±SEM) normalized concentration of perforin (n=3). (B) Flow cytometry analysis of NKG2D ligand Rae-1 expression on LLC tumor cells. (C) $CD8^+$ T cells were co-incubated with CFSE-labeled LLC cells at ratios of 5:1, 10:1, and 25:1 (E:T) for 5 h. After incubation, the cells were stained with PI (1 mg/mL). Live target cells were identified according to light-scatter parameters and PI negativity. Survival of the target cells was measured as the percentage of normalized target cells that remained after incubation with CD8$^+$ T cells. The data are representative of three repeated experiments. (D) Induction of human CD8$^+$ T-cell degranulation by CD80-Fc binding after exposure to target cells. Human CD8$^+$ T cells were enriched from PBMCs, incubated with anti-CD3 microbeads, and treated with control IgG or CD80-Fc in the presence or absence of the STAT3 inhibitor JSI-124 for 24 h. After stimulation, human CD8$^+$ T cells were exposed to CFSE-labeled target K562 cells at a ratio of 1:1 and co-incubated with an anti-CD107a antibody or isotype control antibody for 4 h. Cells were then stained with CD8$^+$ and NKG2D for flow cytometric analysis. The bar graphs show the mean (±SEM) percentage of CD107a$^+$CD8$^+$ T cells before and after exposure to the target cells (n=3). The results represent those for three different healthy donors.

FIGS. 26A-26C: Adoptive transfer of CD80 pre-treated CD8$^+$ T cells improved the antitumor therapeutic effects in LLC tumor model. CD8$^+$ T cells were isolated from the spleens of LLC tumor bearing mice, and stimulated with anti-CD3 plus control Fc (1 mg/mL) and control IgG (10 mg/mL), CD80 Fc (1 mg/mL) and control IgG (10 mg/mL), or CD80 Fc (1 mg/mL) and anti-NKG2D antibody (10 mg/mL) for 48 h. 5×10$^6$ stimulated CD8$^+$ T cells were adoptively transferred to LLC tumor bearing mice (nom) weekly via intravenous injection. (A) NKG2D expression on isolated CD8$^+$ T cells after 48 h treatment with control Fc plus control IgG, CD80 Fc plus control IgG, or CD80 Fc plus NKG2D blocking antibody. CD80Fc+control IgG has the highest NKG2D expression, followed by control Fc+control IgG, CD80Fc+anti-NKG2D, and isotype control. (B) Tumors were dissociated and stained with anti-mouse CD45, CD8$^+$, and NKG2D antibodies to assess NKG2D expression on tumor infiltrating CD8$^+$ T cells. The bar graphs show the median (±SEM). (C) Individual tumor volume (left panel) and survival time (right panel) were monitored twice weekly. The data are representative of three repeated experiments. The control IgG+CD80Fc T cells treatment resulted in the lowest tumor volume and highest percent survival followed by the anti-NKG2D+CD80Fc T cells treatment.

DESCRIPTION OF ILLUSTRATIVE EMBODIMENTS

Figure 1:
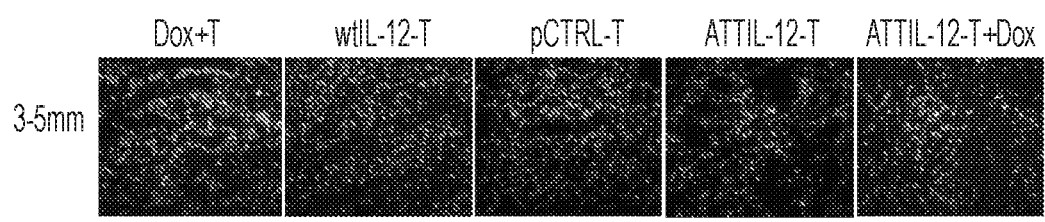
FIG. 1: A549 tumor sections with anti-human CD3 and AF488 anti-rabbit antibody staining. The images represent the center of each section. T cell penetration can be found in the following three treatments in this tumor area: (1) Doxorubicin (Dox) treatment followed by infusion of expanded T cells (Dox+T). (2) Infusion of attIL-12-T cells (attIL-12-T). (3) Infusion of attIL-12 plus prior Dox treatment (attIL-12-T+Dox). There was no detectable T cell penetration in the tumors treated with infusion of T cell alone (pCtrl-T) or wildtype IL-12 modified T cells (wtIL-12-T).

The lack of anti-tumor activity in solid tumors from either TIL or modified T cells (e.g., CAR-T cells) is largely due to the heterogeneity of tumor cells and the lack of infiltration into tumors despite the presence of tumor-targeted antigens as well as inactivation of the infiltrated T cells. Thus, in some embodiments, the present disclosure provides methods for forcing infused T cell penetration into solid tumors with heterogeneity. Specifically, a membrane-anchored tumor targeted IL-12 (attIL-12) is provided herein which can facilitate the penetration of infused T cells into solid tumors. Also provided herein is a population of T cells (e.g., T cells with a CAR or TCR, or tumor infiltrating lymphocytes (TIL)) comprising attIL-12 as well as methods of treating cancer by administering said population of modified T cells. Methods are also provided for the isolation of T cells from the blood of a subject, modification with attIL-12, expansion, and administration to the subject. In addition, subjects may be pretreated with doxorubicin or other T cell recruiting inducers.

Studies in the present disclosure showed that treatment with attIL-12 T cells not only boosted T cell infiltration to solid tumors, but also upregulated the levels of the T cell-attracting chemokines, attracting T cells to the tumor microenvironment and enhancing the persistence of infiltrated T cells by improving the ratios of costimulatory/coinhibitory receptors. In particular, the modified T cells penetrated to the center of tumors (i.e., 5-10 mm from the tumor margin). Interestingly, the attIL-12-modified T cells plus doxorubicin treatment did not induce any detectable toxic IFNγ expression either in the culture medium in vitro or in serum in vivo. This is significant because the induction of IFNγ by wildtype IL12 limits the clinical utility of IL12 due to toxicity. In fact, attIL-12 was observed to inhibit IFNγ induction and promote CD8$^+$ T cell penetration into tumors, resulting in tumor eradication.

In further aspects, the T cells may be engineered to express the attIL-12 by lentiviral transduction of attIL-12 lentivirus. In the present studies, these lentiviral attIL-12 T cells following doxorubicin treatment were shown to effectively inhibit tumor growth. The lentiviral attIL-12 T cells also had reduced T cell accumulation in organs, such as the lungs, compared to control lentiviral T cells. Thus, due to this reduced T cell accumulation in normal tissues, there is a reduced risk of cytokine response syndrome (CRS) as compared to subjects who receive control lentiviral T cell therapy. In some aspects, this method also reduces systemic toxicity and increases the effectiveness of treatment. In addition, the present method can increase T cell survival, increase non-exhausting signal gene CD28 expression, and increase CD80 expression in tumor cells. This CD28 and CD80 interaction can further facilitate the anti-tumor immune response initiated by the NKG2D ligand. Thus, the modified T cells provided herein can be used for the treatment of solid cancers by penetrating into the tumors following their infusion.

In further embodiments, there are provided methods for generating NKG2D$^+$CD8$^+$ T cells by culturing the T cells in the presence of CD80. The T cells may be pre-treated with anti-CD3 microbeads followed by treatment with CD80, such as CD80-Fc recombinant protein, for a period of time (e.g., 1-5 days) sufficient to induce expression of NKG2D in the T cells. The present studies found that T cells which express CD28 are activated by treatment with CD80 through a STAT3 phosphorylation-dependent mechanism. Thus, CD80 may be used to induce NKG2D expression on CD8$^+$ T cells.

I. DEFINITIONS

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

As used herein, the terms "treat," "treatment," "treating," or "amelioration" when used in reference to a disease, disorder or medical condition, refer to therapeutic treatments for a condition, wherein the object is to reverse, alleviate, ameliorate, inhibit, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a condition is reduced or halted. That is, "treatment" includes not just the improvement of symptoms or markers, but also a cessation or at least slowing of progress or worsening of symptoms that would be expected in the absence of treatment. Beneficial or desired clinical results include, but are not limited to, alleviation of one or more symptom(s), diminishment of extent of the deficit, stabilized (i.e., not worsening) state of a tumor or malignancy, delay or slowing of tumor growth and/or metastasis, and an increased lifespan as compared to that expected in the absence of treatment.

"Subject" and "patient" refer to either a human or non-human, such as primates, mammals, and vertebrates. In particular embodiments, the subject is a human.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the size of a tumor, a reduction in the invasiveness of a tumor, reduction in the growth rate of the cancer, or prevention of metastasis. Treatment of cancer may also refer to prolonging survival of a subject with cancer.

An "anti-cancer" agent is capable of negatively affecting a cancer cell/tumor in a subject, for example, by promoting killing of cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer.

By "expression construct" or "expression cassette" is meant a nucleic acid molecule that is capable of directing transcription. An expression construct includes, at a minimum, one or more transcriptional control elements (such as promoters, enhancers or a structure functionally equivalent thereof) that direct gene expression in one or more desired cell types, tissues or organs. Additional elements, such as a transcription termination signal, may also be included.

A "vector" or "construct" (sometimes referred to as a gene delivery system or gene transfer "vehicle") refers to a macromolecule or complex of molecules comprising a polynucleotide to be delivered to a host cell, either in vitro or in vivo.

A "plasmid," a common type of a vector, is an extra-chromosomal DNA molecule separate from the chromosomal DNA that is capable of replicating independently of the chromosomal DNA. In certain cases, it is circular and double-stranded.

A "gene," "polynucleotide," "coding region," "sequence," "segment," "fragment," or "transgene" that "encodes" a particular protein, is a nucleic acid molecule that is transcribed and optionally also translated into a gene product, e.g., a polypeptide, in vitro or in vivo when placed under the control of appropriate regulatory sequences. The coding region may be present in either a cDNA, genomic DNA, or RNA form. When present in a DNA form, the nucleic acid molecule may be single-stranded (i.e., the sense strand) or double-stranded. The boundaries of a coding region are determined by a start codon at the 5' (amino) terminus and a translation stop codon at the 3' (carboxy) terminus. A gene can include, but is not limited to, cDNA from prokaryotic or eukaryotic mRNA, genomic DNA sequences from prokaryotic or eukaryotic DNA, and synthetic DNA sequences. A transcription termination sequence will usually be located 3' to the gene sequence.

The term "control elements" refers collectively to promoter regions, polyadenylation signals, transcription termination sequences, upstream regulatory domains, origins of replication, internal ribosome entry sites (IRES), enhancers, splice junctions, and the like, which collectively provide for the replication, transcription, post-transcriptional processing, and translation of a coding sequence in a recipient cell. Not all of these control elements need be present so long as the selected coding sequence is capable of being replicated, transcribed, and translated in an appropriate host cell.

The term "promoter" is used herein in its ordinary sense to refer to a nucleotide region comprising a DNA regulatory sequence, wherein the regulatory sequence is derived from a gene that is capable of binding RNA polymerise and initiating transcription of a downstream (3' direction) coding sequence. It may contain genetic elements at which regulatory proteins and molecules may bind, such as RNA polymerase and other transcription factors, to initiate the specific transcription of a nucleic acid sequence. The phrases "operatively positioned," "operatively linked," "under control,"

and "under transcriptional control" mean that a promoter is in a correct functional location and/or orientation in relation to a nucleic acid sequence to control transcriptional initiation and/or expression of that sequence.

By "enhancer" is meant a nucleic acid sequence that, when positioned proximate to a promoter, confers increased transcription activity relative to the transcription activity resulting from the promoter in the absence of the enhancer domain.

By "operably linked" or co-expressed" with reference to nucleic acid molecules is meant that two or more nucleic acid molecules (e.g., a nucleic acid molecule to be transcribed, a promoter, and an enhancer element) are connected in such a way as to permit transcription of the nucleic acid molecule. "Operably linked" or "co-expressed" with reference to peptide and/or polypeptide molecules means that two or more peptide and/or polypeptide molecules are connected in such a way as to yield a single polypeptide chain, i.e., a fusion polypeptide, having at least one property of each peptide and/or polypeptide component of the fusion. The fusion polypeptide is preferably chimeric, i.e., composed of heterologous molecules.

The term "antibody" herein is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

The term "monoclonal antibody" as used herein refers to an antibody obtained from a population of substantially homogeneous antibodies, e.g., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The phrases "pharmaceutical or pharmacologically acceptable" refers to molecular entities and compositions that do not produce an adverse, allergic, or other untoward reaction when administered to an animal, such as a human, as appropriate. The preparation of a pharmaceutical composition comprising an antibody or additional active ingredient will be known to those of skill in the art in light of the present disclosure. Moreover, for animal (e.g., human) administration, it will be understood that preparations should meet sterility, pyrogenicity, general safety, and purity standards as required by FDA Office of Biological Standards.

As used herein, "pharmaceutically acceptable carrier" includes any and all aqueous solvents (e.g., water, alcoholic/aqueous solutions, saline solutions, parenteral vehicles, such as sodium chloride, and Ringer's dextrose), non-aqueous solvents (e.g., propylene glycol, polyethylene glycol, vegetable oil, and injectable organic esters, such as ethyloleate), dispersion media, coatings, surfactants, antioxidants, preservatives (e.g., antibacterial or antifungal agents, anti-oxidants, chelating agents, and inert gases), isotonic agents, absorption delaying agents, salts, drugs, drug stabilizers, gels, binders, excipients, disintegration agents, lubricants, sweetening agents, flavoring agents, dyes, fluid and nutrient replenishers, such like materials and combinations thereof, as would be known to one of ordinary skill in the art. The pH and exact concentration of the various components in a pharmaceutical composition are adjusted according to well-known parameters.

The term "unit dose" or "dosage" refers to physically discrete units suitable for use in a subject, each unit containing a predetermined quantity of the therapeutic composition calculated to produce the desired responses discussed above in association with its administration, i.e., the appropriate route and treatment regimen. The quantity to be administered, both according to number of treatments and unit dose, depends on the effect desired. The actual dosage amount of a composition of the present embodiments administered to a patient or subject can be determined by physical and physiological factors, such as body weight, the age, health, and sex of the subject, the type of disease being treated, the extent of disease penetration, previous or concurrent therapeutic interventions, idiopathy of the patient, the route of administration, and the potency, stability, and toxicity of the particular therapeutic substance. For example, a dose may also comprise from about 1 µg/kg/body weight to about 1000 mg/kg/body weight (this such range includes intervening doses) or more per administration, and any range derivable therein. In non-limiting examples of a derivable range from the numbers listed herein, a range of about 5 µg/kg/body weight to about 100 mg/kg/body weight, about 5 µg/kg/body weight to about 500 mg/kg/body weight, etc., can be administered. The practitioner responsible for administration will, in any event, determine the concentration of active ingredient(s) in a composition and appropriate dose(s) for the individual subject.

As used herein, the term "antigen" is a molecule capable of being bound by an antibody or T-cell receptor. An antigen may generally be used to induce a humoral immune response and/or a cellular immune response leading to the production of B and/or T lymphocytes.

The term "immune checkpoint" refers to a molecule such as a protein in the immune system which provides inhibitory signals to its components in order to balance immune reactions. Known immune checkpoint proteins comprise CTLA-4, PD1 and its ligands PD-L1 and PD-L2 and in addition LAG-3, BTLA, B7H3, B7H4, TIM3, KIR. The pathways involving LAG3, BTLA, B7H3, B7H4, TIM3, and KIR are recognized in the art to constitute immune checkpoint pathways similar to the CTLA-4 and PD-1 dependent pathways (see e.g. Pardoll, 2012. *Nature Rev Cancer* 12:252-264; Mellman et al., 2011. *Nature* 480:480-489).

An "immune checkpoint inhibitor" refers to any compound inhibiting the function of an immune checkpoint protein. Inhibition includes reduction of function and full blockade. In particular the immune checkpoint protein is a human immune checkpoint protein. Thus the immune checkpoint protein inhibitor in particular is an inhibitor of a human immune checkpoint protein.

The terms "tumor-associated antigen," "tumor antigen" and "cancer cell antigen" are used interchangeably herein. In each case, the terms refer to proteins, glycoproteins or carbohydrates that are specifically or preferentially expressed by cancer cells.

The term "membrane-anchored IL-12" or "membrane-anchored tumor-targeted IL-12 (attIL-12)" refers to an IL-12 protein that has been modified to comprise a transmembrane domain.

A polynucleotide or polynucleotide region (or a polypeptide or polypeptide region) has a certain percentage (for example, 80%, 85%, 90%, or 95%) of "percent similarity" or "sequence similarity" which refers to the degree by which one amino acid may substitute for another amino acid without loss of function. This percent similarity can be determined through the use of a matrix such as the PAM250 or BLOSUM62 matrix.

A polynucleotide or polynucleotide region (or a polypeptide or polypeptide region) has a certain percentage (for example, 80%, 85%, 90%, or 95%) of "sequence identity" or "homology" to another sequence means that, when aligned, that percentage of bases (or amino acids) are the same in comparing the two sequences. This alignment and the percent homology or sequence identity can be determined using software programs known in the art, for example those described in CURRENT PROTOCOLS IN MOLECULAR BIOLOGY (F. M. Ausubel et al., eds., 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR.

II. ADOPTIVE T CELL THERAPY

Certain embodiments of the present disclosure concern obtaining a starting population of T cells, modifying the T cells, and administering the modified T cells to a subject as an immunotherapy to target cancer cells. In particular, the T cells express membrane-anchored interleukin 12 (IL-12). Several basic approaches for the derivation, activation and expansion of functional anti-tumor effector T cells have been described in the last two decades. These include: autologous cells, such as tumor-infiltrating lymphocytes (TILs); T cells activated ex-vivo using autologous DCs, lymphocytes, artificial antigen-presenting cells (APCs) or beads coated with T cell ligands and activating antibodies, or cells isolated by virtue of capturing target cell membrane; allogeneic cells naturally expressing anti-host tumor T cell receptor (TCR); and non-tumor-specific autologous or allogeneic cells genetically reprogrammed or "redirected" to express tumor-reactive TCR or chimeric TCR molecules displaying antibody-like tumor recognition capacity known as "T-bodies". These approaches have given rise to numerous protocols for T cell preparation and immunization which can be used in the methods described herein.

A. T Cell Preparation

In some embodiments, the starting population of T cells are derived from the blood, bone marrow, lymph, or lymphoid organs. In some aspects, the cells are human cells. The cells typically are primary cells, such as those isolated directly from a subject and/or isolated from a subject and frozen. In some embodiments, the cells include one or more subsets of T cells or other cell types, such as whole T cell populations, CD4$^+$ cells, CD8$^+$ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. In some aspects, such as for off-the-shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, as described herein, and re-introducing them into the same patient, before or after cryopreservation.

Among the sub-types and subpopulations of T cells (e.g., CD4$^+$ and/or CD8$^+$ T cells) are naive T ($T_N$) cells, effector T cells ($T_{EFF}$), memory T cells and sub-types thereof, such as stem cell memory T ($TSC_M$), central memory T ($TC_M$), effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, one or more of the T cell populations is enriched for or depleted of cells that are positive for a specific marker, such as surface markers, or that are negative for a specific marker. In some cases, such markers are those that are absent or expressed at relatively low levels on certain populations of T cells (e.g., non-memory cells) but are present or expressed at relatively higher levels on certain other populations of T cells (e.g., memory cells).

In some embodiments, T cells are separated from a PBMC sample by negative selection of markers expressed on non-T cells, such as B cells, monocytes, or other white blood cells, such as CD14. In some aspects, a CD4$^+$ or CD8$^+$ selection step is used to separate CD4$^+$ helper and CD8$^+$ cytotoxic T cells. Such CD4$^+$ and CD8$^+$ populations can be further sorted into sub-populations by positive or negative selection for markers expressed or expressed to a relatively higher degree on one or more naive, memory, and/or effector T cell subpopulations.

In some embodiments, CD8$^+$ T cells are further enriched for or depleted of naive, central memory, effector memory, and/or central memory stem cells, such as by positive or negative selection based on surface antigens associated with the respective subpopulation. In some embodiments, enrichment for central memory T ($T_{CM}$) cells is carried out to increase efficacy, such as to improve long-term survival, expansion, and/or engraftment following administration, which in some aspects is particularly robust in such sub-populations. See Terakura et al. (2012) *Blood.* 1:72-82; Wang et al. (2012) *J Immunother.* 35(9):689-701.

In some embodiments, the T cells are autologous T cells. In this method, tumor samples are obtained from patients and a single cell suspension is obtained. The single cell suspension can be obtained in any suitable manner, e.g., mechanically (disaggregating the tumor using, e.g., a gentleMACS™ Dissociator, Miltenyi Biotec, Auburn, Calif.) or enzymatically (e.g., collagenase or DNase). Single-cell suspensions of tumor enzymatic digests are cultured in interleukin-2 (IL-2). The cells are cultured until confluence (e.g., about $2\times10^6$ lymphocytes), e.g., from about 5 to about 21 days, preferably from about 10 to about 14 days. For example, the cells may be cultured from 5 days, 5.5 days, or 5.8 days to 21 days, 21.5 days, or 21.8 days, such as from 10 days, 10.5 days, or 10.8 days to 14 days, 14.5 days, or 14.8 days.

The cultured T cells can be pooled and rapidly expanded. Rapid expansion provides an increase in the number of antigen-specific T-cells of at least about 50-fold (e.g., 50-, 60-, 70-, 80-, 90-, or 100-fold, or greater) over a period of about 10 to about 14 days. More preferably, rapid expansion provides an increase of at least about 200-fold (e.g., 200-, 300-, 400-, 500-, 600-, 700-, 800-, 900-, or greater) over a period of about 10 to about 14 days.

Expansion can be accomplished by any of a number of methods as are known in the art. For example, T cells can be rapidly expanded using non-specific T-cell receptor stimulation in the presence of feeder lymphocytes and either interleukin-2 (IL-2) or interleukin-15 (IL-15), with IL-2 being preferred. The non-specific T-cell receptor stimulus can include around 30 ng/ml of OKT3, a mouse monoclonal anti-CD3 antibody (available from Ortho-McNeil®, Raritan, N.J.). Alternatively, T cells can be rapidly expanded by stimulation of peripheral blood mononuclear cells (PBMC) in vitro with one or more antigens (including antigenic portions thereof, such as epitope(s), or a cell) of the cancer, which can be optionally expressed from a vector, such as an human leukocyte antigen A2 (HLA-A2) binding peptide, in the presence of a T-cell growth factor, such as 300 IU/ml IL-2 or IL-15, with IL-2 being preferred. The in vitro-induced T-cells are rapidly expanded by re-stimulation with the same antigen(s) of the cancer pulsed onto HLA-A2-expressing antigen-presenting cells. Alternatively, the T-cells can be re-stimulated with irradiated, autologous lymphocytes or with irradiated HLA-A2$^+$ allogeneic lymphocytes and IL-2, for example.

The autologous T-cells can be modified to express a T-cell growth factor that promotes the growth and activation of the autologous T-cells. Suitable T-cell growth factors include, for example, interleukin (IL)-2, IL-7, IL-15, and IL-12. Suitable methods of modification are known in the art. See, for instance, Sambrook et al., *Molecular Cloning: A Laboratory Manual*, 3$^{rd}$ ed., Cold Spring Harbor Press, Cold Spring Harbor, N.Y. 2001; and Ausubel et al., *Current Protocols in Molecular Biology*, Greene Publishing Associates and John Wiley & Sons, N Y, 1994. In particular aspects, modified autologous T-cells express the T-cell growth factor at high levels. T-cell growth factor coding sequences, such as that of IL-12, are readily available in the art, as are promoters, the operable linkage of which to a T-cell growth factor coding sequence promote high-level expression.

B. T Cell Activation

In some embodiments, the present disclosure provides methods of activating T cells to increase expression of NKG2D receptor on the T cells, such as CD8$^+$ T cells. The starting population of T cells may be pre-treated with anti-CD3, such anti-CD3 beads. The pre-treatment may be for about 12 hours to 3 days, such as about 24 hours. The expanded T cells may then be cultured with CD80 protein, such as CD80-Fc recombinant protein to induce CD28 activation and, thus, NKG2D expression. The culture with CD80 may be for about 1-6 days, such as about 1, 2, 3, 4, 5, or 6 days, particularly about 4 days. In some aspects, the T cells may be treated with anti-CD3 and CD80 simultaneously.

C. T Cells with Membrane-Anchored IL-12

In particular embodiments, T cells expressing membrane-anchored IL-12 are provided herein. The membrane-anchored IL-12 of the present disclosure may comprise SEQ ID NO:1 and SEQ ID NO:4 which comprises the IL-12 alpha subunit p35 (NCBI Reference Sequence: NP_000873.2; SEQ ID NO:2), a linker, a transmembrane domain (e.g., SEQ ID NO:31 and IL-12 beta subunit p40 (NCBI Reference Sequence: NP_002178.2; SEQ ID NO:4). Also provided herein are compositions comprising membrane-anchored IL-12 which can include protein and/or nucleic acids encoding membrane-anchored IL-12. In some aspects, the membrane-anchored IL-12 heterodimer protein provided herein has at least about 90% sequence identity with SEQ ID NO:1 and SEQ ID NO:4, such as at least about 91%, 92%, 93%, 94%, 95%, 96%, 97%, 98% or 99% sequence identity with SEQ ID NO: 1 and SEQ ID NO:4.

In some embodiments, the C-terminal of the IL-12 p35 subunit is fused to a transmembrane domain. The transmembrane domain may comprise SEQ ID NO:3. In other embodiments, the transmembrane domain may comprise other transmembrane sequence known in the art such as disclosed in Kozma et al., *Nucleic Acids Research* 41 Database Issue, D524-D529, 2013. In other embodiments, the IL-12 p40 comprises a transmembrane domain. Well known examples of transmembrane proteins having one or more transmembrane polypeptide domains include members of the integrin family, CD44, glycophorin. MHC Class I and II glycoproteins, EGF receptor, G protein coupled receptor (GPCR) family, receptor tyrosine kinases (such as insulin-like growth factor 1 receptor (IGFR) and platelet-derived growth factor receptor (PDGFR)), porin family and other transmembrane proteins. Certain embodiments of the present disclosure contemplate using a portion of a transmembrane polypeptide domain such as a truncated polypeptide having membrane-inserting characteristics as may be determined according to standard and well known methodologies.

A variety of linkers can be used in the membrane-anchored IL-12 of the embodiments. In some aspects a linker can be a random string of one or more amino acids (e.g., 2, 3, 4, 5, 10, 15, 20 or more amino acids). Some specific linkers for use according the embodiments include the 218 (GSTSGSGKPGSGEGSTKG), the HL (EAAAK) and the G$_4$S (GGCGS) linkers The membrane-anchored IL-12 protein sequences that can be used in various embodiments include the amino acid sequences described herein, as well as analogues and derivatives thereof. The analogues and derivatives can include, but are not limited to, additions or substitutions of amino acid residues within the amino acid sequences encoded by a nucleotide sequence, but that result in a silent change, thus producing a functionally equivalent gene product. Amino acid substitutions may be made on the basis of similarity in polarity, charge, solubility, hydrophobicity, hydrophilicity, and/or the amphipathic nature of the residues involved. For example: nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

Amino acid substitutions may alternatively be made on the basis of the hydropathic index of amino acids. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). The use of the hydropathic amino acid index in conferring interactive biological function on a protein is understood in the art (Kyte and Doolittle, *J. Mol. Biol.* 157:105-132, 1982). It is known that in certain instances, certain amino acids may be substituted for other amino acids having a similar hydropathic index or score and still retain a similar biological activity. In making changes based upon the hydropathic index, in certain embodiments the substitution of amino acids whose hydropathic indices are within ±2 is included, while in other embodiments amino acid substitutions that are within ±1 are included, and in yet other embodiments amino acid substitutions within ±0.5 are included.

Amino acid substitutions may alternatively be made on the basis of hydrophilicity, particularly where the biologically functional protein or peptide thereby created is intended for use in immunological embodiments. In certain embodiments, the greatest local average hydrophilicity of a protein, as governed by the hydrophilicity of its adjacent amino acids, correlates with its immunogenicity and antigenicity, i.e., with a biological property of the protein. The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments the substitution of amino acids whose hydrophilicity values are within ±2 is included, in certain embodiments those that are within ±1 are included, and in certain embodiments those within ±0.5 are included. One may also identify epitopes from primary amino acid sequences on the basis of hydrophilicity.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

In some aspects, a nucleic acid encoding the membrane-anchored IL-12 is administered or introduced to a cell, such as a T cell. The nucleic acid typically is administered in the form of an expression vector. In some aspects, the expression vector is a retroviral expression vector, an adenoviral expression vector, a DNA plasmid expression vector, or an AAV expression vector. In some aspects, one or more polynucleotides encoding the membrane-anchored IL-12 is delivered to the cell. In some aspects, the delivery is by delivery of one or more vectors, one or more transcripts thereof, and/or one or more proteins transcribed therefrom, is delivered to the cell.

In some embodiments, the polypeptides are synthesized in situ in the cell as a result of the introduction of polynucleotides encoding the polypeptides into the cell. In some aspects, the polypeptides could be produced outside the cell and then introduced thereto. Methods for introducing a polynucleotide construct into animal cells are known and include, as non-limiting examples stable transformation methods wherein the polynucleotide construct is integrated into the genome of the cell, transient transformation methods wherein the polynucleotide construct is not integrated into the genome of the cell, and virus mediated methods. In some embodiments, the polynucleotides may be introduced into the cell by for example, recombinant viral vectors (e.g. retroviruses, adenoviruses), liposome and the like. For example, in some aspects, transient transformation methods include microinjection, electroporation, or particle bombardment. In some embodiments, the polynucleotides may be included in vectors, more particularly plasmids or virus, in view of being expressed in the cells.

In some embodiments, viral and non-viral based gene transfer methods can be used to introduce nucleic acids in mammalian cells or target tissues. Such methods can be used to administer nucleic acids encoding components of a CRISPR, ZFP, ZFN, TALE, and/or TALEN system to cells in culture, or in a host organism. Non-viral vector delivery systems include DNA plasmids, RNA (e.g. a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell. For a review of gene therapy procedures, see Anderson, 1992; Nabel & Feigner, 1993; Mitani & Caskey, 1993; Dillon, 1993; Miller, 1992; Van Brunt, 1988; Vigne, 1995; Kremer & Perricaudet, 1995; Haddada et al., 1995; and Yu et al., 1994.

Methods of non-viral delivery of nucleic acids include lipofection, nucleofection, microinjection, biolistics, virosomes, liposomes, immunoliposomes, polycation or lipid:nucleic acid conjugates, naked DNA, artificial virions, and agent-enhanced uptake of DNA. Lipofection is described in (e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Feigner, WO 91117424; WO 91116024. Delivery can be to cells (e.g. in vitro or ex vivo administration) or target tissues (e.g. in vivo administration).

In some embodiments, delivery is via the use of RNA or DNA viral based systems for the delivery of nucleic acids. Viral vectors in some aspects may be administered directly to patients (in vivo) or they can be used to treat cells in vitro or ex vivo, and then administered to patients. Viral-based systems in some embodiments include retroviral, lentivirus, adenoviral, adeno-associated and herpes simplex virus vectors for gene transfer.

In some aspects, a reporter gene which includes but is not limited to glutathione-5-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP), may be introduced into the cell to encode a gene product which serves as a marker by which to measure the alteration or modification of expression of the gene product. In a further embodiment, the DNA molecule encoding the gene product may be introduced into the cell via a vector. In some embodiments, the gene product is luciferase.

D. Genetically Engineered Antigen Receptors

The T cells of the present disclosure can be genetically engineered to express antigen receptors such as engineered TCRs and/or chimeric antigen receptors (CARs). For example, the autologous T-cells are modified to express a T cell receptor (TCR) having antigenic specificity for a cancer antigen. Suitable methods of modification are known in the art. See, for instance, Sambrook and Ausubel, supra. For example, the T cells may be transduced to express a T cell receptor (TCR) having antigenic specificity for a cancer antigen using transduction techniques described in Heemskerk et al. *Hum Gene Ther.* 19:496-510 (2008) and Johnson et al. *Blood* 114:535-46 (2009).

In some embodiments, the T cells comprise one or more nucleic acids introduced via genetic engineering that encode one or more antigen receptors, and genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature (e.g., chimeric).

In some embodiments, the CAR contains an extracellular antigen-recognition domain that specifically binds to an antigen. In some embodiments, the antigen is a protein expressed on the surface of cells. In some embodiments, the CAR is a TCR-like CAR and the antigen is a processed peptide antigen, such as a peptide antigen of an intracellular protein, which, like a TCR, is recognized on the cell surface in the context of a major histocompatibility complex (MHC) molecule.

Exemplary antigen receptors, including CARs and recombinant TCRs, as well as methods for engineering and introducing the receptors into cells, include those described, for example, in international patent application publication numbers WO200014257, WO2013126726, WO2012/129514, WO2014031687, WO2013/166321, WO2013/071154, WO2013/123061 U.S. patent application publication numbers US2002131960, US2013287748, US20130149337. U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., *Cancer Discov.* 2013 April; 3(4): 388-398; Davila et al. (2013) *PLoS ONE* 8(4): e61338; Turtle et al., *Curr. Opin. Immunol.*, 2012 October; 24(5): 633-39; Wu et al., *Cancer*, 2012 Mar. 18(2): 160-75. In some aspects, the genetically engineered antigen receptors include a CAR as described in U.S. Pat. No. 7,446,190, and those described in International Patent Application Publication No.: WO/2014055668 A1.

In some aspects, the tumor antigen is a human telomerase reverse transcriptase (hTERT), survivin, mouse double minute 2 homolog (MDM2), cytochrome P450 1B1 (CYP1B), HER2/neu, Wilms' tumor gene 1 (WT1), livin, alphafetoprotein (AFP), carcinoembryonic antigen (CEA), mucin 16 (MUC16), MUC1, prostate-specific membrane antigen (PSMA), p53 or cyclin (D1). For example, the target antigen is hTERT or survivin. In some aspects, the target antigen is CD38. In other aspects, the target antigen is CD33 or TIM-3. In other aspects, it is CD26, CD30, CD53, CD92, CD148, CD150, CD200, CD261, CD262, or CD362. In some embodiments, the engineered immune cells can contain an antigen that targets one or more other antigens. In some embodiments, the one or more other antigens is a tumor antigen or cancer marker. Other antigens include orphan tyrosine kinase receptor ROR1, tEGFR, Her2, L1-CAM, CD19, CD20, CD22, mesothelin, CEA, and hepatitis B surface antigen, anti-folate receptor, CD23, CD24, CD30, CD33, CD38, CD44, EGFR, EGP-2, EGP-4, EPHa2, ErbB2, 3, or 4, FBP, fetal acethycholine e receptor, GD2, GD3, HMW-MAA, IL-22R-alpha, IL-13R-alpha2, kdr, kappa light chain, Lewis Y, L1-cell adhesion molecule, MAGE-A1, mesothelin, MUC1, MUC16, PSCA, NKG2D Ligands, NY-ESO-1, MART-1, gp1OO, oncofetal antigen, ROR1, TAG72, VEGF-R2, carcinoembryonic antigen (CEA), prostate specific antigen, PSMA, Her2/neu, estrogen receptor, progesterone receptor, ephrinB2, CD 123, CS-1, c-Met, GD-2, and MAGE A3, CE7, Wilms Tumor 1 (WT-1), a cyclin, such as cyclin A1 (CCNA1), and/or biotinylated molecules, and/or molecules expressed by HIV, HCV, HBV or other pathogens.

1. Chimeric Antigen Receptors

In some embodiments, the engineered antigen receptors include chimeric antigen receptors (CARs), including activating or stimulatory CARs, costimulatory CARS (see WO2014/055668), and/or inhibitory CARs (iCARs, see Fedorov et al., *Sci. Transl. Medicine*, 5(215) (December, 2013). The CARs generally include an extracellular antigen (or ligand) binding domain linked to one or more intracellular signaling components, in some aspects via linkers and/or transmembrane domain(s). Such molecules typically mimic or approximate a signal through a natural antigen receptor, a signal through such a receptor in combination with a costimulatory receptor, and/or a signal through a costimulatory receptor alone.

In some embodiments, CAR is constructed with a specificity for a particular antigen (or marker or ligand), such as an antigen expressed in a particular cell type to be targeted by adoptive therapy, e.g., a cancer marker, and/or an antigen intended to induce a dampening response, such as an antigen expressed on a normal or non-diseased cell type. Thus, the CAR typically includes in its extracellular portion one or more antigen binding molecules, such as one or more antigen-binding fragment, domain, or portion, or one or more antibody variable domains, and/or antibody molecules. In some embodiments, the CAR includes an antigen-binding portion or portions of an antibody molecule, such as a single-chain antibody fragment (scFv) derived from the variable heavy (VH) and variable light (VL) chains of a monoclonal antibody (mAb).

In some aspects, the antigen-specific binding, or recognition component is linked to one or more transmembrane and intracellular signaling domains. In some embodiments, the CAR includes a transmembrane domain fused to the extracellular domain of the CAR. In one embodiment, the transmembrane domain that naturally is associated with one of the domains in the CAR is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 epsilon, CD45, CD4, CD5, CDS, CD9, CD16, CD22, CD33, CD37, CD64, CD80, CD86, CD134, CD137, CD 154. Alternatively the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain.

The CAR generally includes at least one intracellular signaling component or components. In some embodiments, the CAR includes an intracellular component of the TCR complex, such as a TCR CD3$^+$ chain that mediates T-cell activation and cytotoxicity, e.g., CD3 zeta chain. Thus, in some aspects, the antigen binding molecule is linked to one or more cell signaling modules. In some embodiments, cell signaling modules include CD3 transmembrane domain, CD3 intracellular signaling domains, and/or other CD transmembrane domains. In some embodiments, the CAR further includes a portion of one or more additional molecules such as Fc receptor γ, CD8, CD4, CD25, or CD16. For example, in some aspects, the CAR includes a chimeric molecule between CD3-zeta (CD3-Q or Fc receptor γ and CD8, CD4, CD25 or CD16.

2. T Cell Receptor (TCR)

In some embodiments, the genetically engineered antigen receptors include recombinant T cell receptors (TCRs) and/ or TCRs cloned from naturally occurring T cells. A "T cell receptor" or "TCR" refers to a molecule that contains a variable α and β chains (also known as TCRa and TCRp, respectively) or a variable γ and δ chains (also known as TCRy and TCR5, respectively) and that is capable of specifically binding to an antigen peptide bound to a MHC receptor. In some embodiments, the TCR is in the αβ form. Typically, TCRs that exist in αβ and γδ forms are generally structurally similar, but T cells expressing them may have distinct anatomical locations or functions. A TCR can be found on the surface of a cell or in soluble form. Generally, a TCR is found on the surface of T cells (or T lymphocytes) where it is generally responsible for recognizing antigens bound to major histocompatibility complex (MHC) molecules. In some embodiments, a TCR also can contain a constant domain, a transmembrane domain and/or a short cytoplasmic tail (see, e.g., Janeway et al, Immunobiology: The Immune System in Health and Disease, 3 rd Ed., Current Biology Publications, p. 4:33, 1997). For example, in some aspects, each chain of the TCR can possess one N-terminal immunoglobulin variable domain, one immunoglobulin constant domain, a transmembrane region, and a short cytoplasmic tail at the C-terminal end. In some embodiments, a TCR is associated with invariant proteins of the CD3 complex involved in mediating signal transduction.

Unless otherwise stated, the term "TCR" should be understood to encompass functional TCR fragments thereof. The term also encompasses intact or full-length TCRs, including TCRs in the αβ form or γδ form.

Thus, for purposes herein, reference to a TCR includes any TCR or functional fragment, such as an antigen-binding portion of a TCR that binds to a specific antigenic peptide bound in an MHC molecule, i.e. MHC-peptide complex. An "antigen-binding portion" or antigen-binding fragment" of a TCR, which can be used interchangeably, refers to a molecule that contains a portion of the structural domains of a TCR, but that binds the antigen (e.g. MHC-peptide complex) to which the full TCR binds. In some cases, an antigen-binding portion contains the variable domains of a TCR, such as variable a chain and variable β chain of a TCR, sufficient to form a binding site for binding to a specific MHC-peptide complex, such as generally where each chain contains three complementarity determining regions.

In some embodiments, the variable domains of the TCR chains associate to form loops, or complementarity determining regions (CDRs) analogous to immunoglobulins, which confer antigen recognition and determine peptide specificity by forming the binding site of the TCR molecule and determine peptide specificity. Typically, like immunoglobulins, the CDRs am separated by framework regions (FRs) (see, e.g., Jores et al., *PNAS U.S.A.* 87:9138, 1990; Chothia et al., *EMBO J.* 7:3745, 1988; see also Lefranc et al., *Dev. Comp. Immunol.* 27:55.2003). In some embodiments, CDR3 is the main CDR responsible for recognizing processed antigen, although CDR1 of the alpha chain has also been shown to interact with the N-terminal part of the antigenic peptide, whereas CDR1 of the beta chain interacts with the C-terminal part of the peptide. CDR2 is thought to recognize the MHC molecule. In some embodiments, the variable region of the β-chain can contain a further hypervariability (HV4) region.

In some embodiments, the TCR chains contain a constant domain. For example, like immunoglobulins, the extracellular portion of TCR chains (e.g., α-chain, β-chain) can contain two immunoglobulin domains, a variable domain (e.g., $V_a$ or Vp; typically amino acids 1 to 116 based on Kabat numbering Kabat et al., "Sequences of Proteins of Immunological Interest, US Dept. Health and Human Services, Public Health Service National Institutes of Health, 1991, 5$^{th}$ ed.) at the N-terminus, and one constant domain (e.g., a-chain constant domain or $C_a$, typically amino acids 117 to 259 based on Kabat, β-chain constant domain or Cp, typically amino acids 117 to 295 based on Kabat) adjacent to the cell membrane. For example, in some cases, the extracellular portion of the TCR formed by the two chains contains two membrane-proximal constant domains, and two membrane-distal variable domains containing CDRs. The constant domain of the TCR domain contains short connecting sequences in which a cysteine residue forms a disulfide bond, making a link between the two chains. In some embodiments, a TCR may have an additional cysteine residue in each of the α and β chains such that the TCR contains two disulfide bonds in the constant domains.

In some embodiments, the TCR chains can contain a transmembrane domain. In some embodiments, the transmembrane domain is positively charged. In some cases, the TCR chains contains a cytoplasmic tail. In some cases, the structure allows the TCR to associate with other molecules like CD3. For example, a TCR containing constant domains with a transmembrane region can anchor the protein in the cell membrane and associate with invariant subunits of the CD3 signaling apparatus or complex.

Generally, CD3 is a multi-protein complex that can possess three distinct chains (γ, δ, and ε) in mammals and the ζ-chain. For example, in mammals the complex can contain a CD3γ chain, a CD3δ chain, two CD3ε chains, and a homodimer of CD3ζ chains. The CD3γ, CD3δ, and CD3ε chains are highly related cell surface proteins of the immunoglobulin superfamily containing a single immunoglobulin domain. The transmembrane regions of the CD3γ, CD3δ, and CD3ε chains are negatively charged, which is a characteristic that allows these chains to associate with the positively charged T cell receptor chains. The intracellular tails of the CD3γ, CD3δ, and CD3ε chains each contain a single conserved motif known as an immunoreceptor tyrosine-based activation motif or ITAM, whereas each CD3ζ chain has three. Generally, ITAMs are involved in the signaling capacity of the TCR complex. These accessory molecules have negatively charged transmembrane regions and play a role in propagating the signal from the TCR into the cell. The CD3- and ζ-chains, together with the TCR, form what is known as the T cell receptor complex.

In some embodiments, the TCR may be a heterodimer of two chains α and β (or optionally γ and δ) or it may be a single chain TCR construct. In some embodiments, the TCR is a heterodimer containing two separate chains (α and β chains or γ and δ chains) that are linked, such as by a disulfide bond or disulfide bonds. In some embodiments, a TCR for a target antigen (e.g., a cancer antigen) is identified and introduced into the cells. In some embodiments, nucleic acid encoding the TCR can be obtained from a variety of sources, such as by polymerase chain reaction (PCR) amplification of publicly available TCR DNA sequences. In some embodiments, the TCR is obtained from a biological source, such as from cells such as from a T cell (e.g. cytotoxic T cell). T-cell hybridomas or other publicly available source. In some embodiments, the T-cells can be obtained from in vivo isolated cells. In some embodiments, a high-affinity T cell clone can be isolated from a patient, and the TCR isolated. In some embodiments, the T-cells can be a cultured T-cell hybridoma or clone. In some embodiments, the TCR clone for a target antigen has been generated in transgenic mice engineered with human immune system genes (e.g., the human leukocyte antigen system, or HLA). See, e.g., tumor antigens (see, e.g., Parkhurst et al. (2009) *Clin Cancer Res.* 15: 169-180 and Cohen et al. (2005) *J Immunol.* 175:5799-5808. In some embodiments, phage display is used to isolate TCRs against a target antigen (see, e.g., Varela-Rohena et al. (2008) *Nat Med.* 14: 1390-1395 and Li (2005) *Nat Biotechnol.* 23:349-354. In some embodiments, the TCR or antigen-binding portion thereof can be synthetically generated from knowledge of the sequence of the TCR.

3. Antigen-Presenting Cells

Antigen-presenting cells, which include macrophages, B lymphocytes, and dendritic cells, are distinguished by their expression of a particular MHC molecule. APCs internalize antigen and re-express a part of that antigen, together with the MHC molecule on their outer cell membrane. The major histocompatibility complex (MHC) is a large genetic complex with multiple loci. The MHC loci encode two major classes of MHC membrane molecules, referred to as class I and class II MHCs. T helper lymphocytes generally recognize antigen associated with MHC class II molecules, and T cytotoxic lymphocytes recognize antigen associated with MHC class I molecules. In humans the MHC is referred to as the HLA complex and in mice the H-2 complex.

In some cases, aAPCs are useful in preparing therapeutic compositions and cell therapy products of the embodiments. For general guidance regarding the preparation and use of antigen-presenting systems, see, e.g., U.S. Pat. Nos. 6,225,042, 6,355,479, 6,362,001 and 6,790,662; U.S. Patent Application Publication Nos. 2009/0017000 and 2009/0004142; and International Publication No. WO2007/103009.

aAPC systems may comprise at least one exogenous assisting molecule. Any suitable number and combination of assisting molecules may be employed. The assisting molecule may be selected from assisting molecules such as co-stimulatory molecules and adhesion molecules. Exemplary co-stimulatory molecules include CD86, CD64 (FcγRI), 41BB ligand, and IL-21. Adhesion molecules may include carbohydrate-binding glycoproteins such as selectins, transmembrane binding glycoproteins such as integrins, calcium-dependent proteins such as cadherins, and single-pass transmembrane immunoglobulin (Ig) superfamily proteins, such as intercellular adhesion molecules (ICAMs), which promote, for example, cell-to-cell or cell-to-matrix contact. Exemplary adhesion molecules include LFA-3 and ICAMs, such as ICAM-1. Techniques, methods, and reagents useful for selection, cloning, preparation, and expression of exemplary assisting molecules, including co-stimulatory molecules and adhesion molecules, are exemplified in, e.g., U.S. Pat. Nos. 6,225,042, 6,355,479, and 6,362,001.

III. METHODS OF TREATMENT

Further provided herein are methods for treating or delaying progression of cancer in an individual comprising administering to the individual an effective amount a T cell therapy, such as T cells expressing membrane-anchored IL-12 and/or T cells which have been activated to express NKG2D. Examples of cancers contemplated for treatment include lung cancer, head and neck cancer, breast cancer, pancreatic cancer, prostate cancer, renal cancer, bone cancer, testicular cancer, cervical cancer, gastrointestinal cancer, lymphomas, pre-neoplastic lesions in the lung, colon cancer, melanoma, and bladder cancer.

In some embodiments, the individual has cancer that is resistant (has been demonstrated to be resistant) to one or more anti-cancer therapies. In some embodiments, resistance to anti-cancer therapy includes recurrence of cancer or refractory cancer. Recurrence may refer to the reappearance of cancer, in the original site or a new site, after treatment. In some embodiments, resistance to anti-cancer therapy includes progression of the cancer during treatment with the anti-cancer therapy. In some embodiments, the cancer is at early stage or at late stage.

In some embodiments, the subject is administered a chemotherapeutic in combination with the T cell therapy. For example, the chemotherapeutic may be doxorubicin (Dox) or cyclophosphamide. Subjects may be pretreated with chemotherapeutic such as doxorubicin or other T cell recruiting inducers. The pretreatment may be 16-24 hours prior to the T cell therapy.

In some embodiments, T cells are autologous. However the cells can be allogeneic if the endogenous TCRs are knockout. In some embodiments, the T cells are isolated from the patient themself, so that the cells are autologous. If the T cells are allogeneic, the endogenous TCR needs to be removed. The cells are administered to the subject of interest in an amount sufficient to control, reduce, or eliminate symptoms and signs of the disease being treated.

The effectiveness of treatment can be measured by many methods known to those of skill in the art. In one embodiment, a white blood cell count (WBC) is used to determine the responsiveness of a subject's immune system. A WBC measures the number of white blood cells in a subject. Using methods well known in the art, the white blood cells in a subject's blood sample are separated from other blood cells and counted. Normal values of white blood cells are about 4,500 to about 10.000 white blood cells/µl. Lower numbers of white blood cells can be indicative of a state of immunosuppression in the subject.

In another embodiment, immunosuppression in a subject may be determined using a T-lymphocyte count. Using methods well known in the art, the white blood cells in a subject's blood sample are separated from other blood cells. T-lymphocytes are differentiated from other white blood cells using standard methods in the art, such as, for example, immunofluorescence or FACS. Reduced numbers of T cells, or a specific population of T-cells can be used as a measurement of immunosuppression. A reduction in the number of T cells, or in a specific population of T cells, compared to the number of T cells (or the number of cells in the specific population) prior to treatment can be used to indicate that immunosuppression has been induced.

In additional embodiments, tests to measure T cell activation, proliferation, or cytokine responses including those to specific antigens are performed. In some examples, the number of Treg or Breg cells can be measured in a sample from a subject. In additional examples, cytokines are measured in a sample, from a subject, such as IL-10.

In other examples, to assess inflammation, neutrophil infiltration at the site of inflammation can be measured. In order to assess neutrophil infiltration myeloperoxidase activity can be measured. Myeloperoxidase is a hemoprotein present in azurophilic granules of polymorphonuclear leukocytes and monocytes. It catalyzes the oxidation of halide ions to their respective hypohalous acids, which are used for microbial killing by phagocytic cells. Thus, a decrease in myeloperoxidase activity in a tissue reflects decreased neutrophil infiltration, and can serve as a measure of inhibition of inflammation.

In another example, effective treatment of a subject can be assayed by measuring cytokine levels in the subject. Cytokine levels in body fluids or cell samples are determined by conventional methods. For example, an immunospot assay, such as the enzyme-linked immunospot or "ELISPOT" assay, can be used. The immunospot assay is a highly sensitive and quantitative assay for detecting cytokine secretion at the single cell level. Immunospot methods and applications are well known in the art and are described, for example, in Czerkinsky et al., 1988; Olsson et al., 1990; and EP 957359. Variations of the standard immunospot assay are well known in the art and can be used to detect alterations in cytokine production in the methods of the disclosure (see, for example, U.S. Pat. Nos. 5,939,281 and 6,218,132).

In some embodiments, the subject can be administered nonmyeloablative lymphodepleting chemotherapy prior to the T cell therapy. The nonmyeloablative lymphodepleting chemotherapy can be any suitable such therapy, which can be administered by any suitable route. The nonmyeloablative lymphodepleting chemotherapy can comprise, for example, the administration of cyclophosphamide and fludarabine, particularly if the cancer is melanoma, which can be metastatic. An exemplary route of administering cyclophosphamide and fludarabine is intravenously. Likewise, any suitable dose of cyclophosphamide and fludarabine can be administered. In particular aspects, around 60 mg/kg of cyclophosphamide is administered for two days after which around 25 mg/m² fludarabine is administered for five days.

In certain embodiments, a T cell growth factor that promotes the growth and activation of the autologous T cells is administered to the subject either concomitantly with the autologous T cells or subsequently to the autologous T cells. The T cell growth factor can be any suitable growth factor that promotes the growth and activation of the autologous T-cells. Examples of suitable T cell growth factors include interleukin (IL)-2, IL-7, IL-15, and IL-12, which can be used alone or in various combinations, such as IL-2 and IL-7, IL-2 and IL-15, IL-7 and IL-15, IL-2, IL-7 and IL-15, IL-12 and IL-7, IL-12 and IL-15, or IL-12 and IL2. IL-12 is a preferred T-cell growth factor.

Intratumoral injection, or injection into the tumor vasculature is specifically contemplated for discrete, solid, accessible tumors. Local, regional or systemic administration also may be appropriate. For tumors of >4 cm, the volume to be administered will be about 4-10 ml (in particular 10 ml), while for tumors of <4 cm, a volume of about 1-3 ml will be used (in particular 3 ml). Multiple injections delivered as single dose comprise about 0.1 to about 0.5 ml volumes.

B. Pharmaceutical Compositions

Also provided herein are pharmaceutical compositions and formulations comprising a T cell therapy and a pharmaceutically acceptable carrier.

Pharmaceutical compositions and formulations as described herein can be prepared by mixing the active ingredients (such as an antibody or a polypeptide) having the desired degree of purity with one or more optional pharmaceutically acceptable carriers (Remington's Pharmaceutical Sciences 22nd edition, 2012), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

C. Additional Therapy

In certain embodiments, the compositions and methods of the present embodiments involve a T cell population, such as expressing membrane-anchored IL-12 and/or expressing NKG2D, in combination with at least one additional therapy. The additional therapy may be radiation therapy, surgery (e.g., lumpectomy and a mastectomy), chemotherapy, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant or neoadjuvant therapy.

A T cell therapy may be administered before, during, after, or in various combinations relative to an additional therapy, such as doxorubicin. The administrations may be in intervals ranging from concurrently to minutes to days to weeks. In embodiments where the T cell therapy is provided to a patient separately from an additional therapeutic agent, one would generally ensure that a significant period of time did not expire between the time of each delivery, such that the two compounds would still be able to exert an advantageously combined effect on the patient. In such instances, it is contemplated that one may provide a patient with the T cell therapy and the anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

The T cell therapy and the additional therapeutic agent may be administered by the same route of administration or by different routes of administration. In some embodiments, the T cell therapy and/or anti-platelet agent is administered intravenously, intramuscularly, subcutaneously, topically, orally, transdermally, intraperitoneally, intraorbitally, by implantation, by inhalation, intrathecally, intraventricularly, or intranasally. An effective amount of the T cell therapy and additional therapeutic agent may be administered for prevention or treatment of disease. The appropriate dosage of the T cell therapy and additional therapeutic agent be determined based on the type of disease to be treated, severity and course of the disease, the clinical condition of the individual, the individual's clinical history and response to the treatment, and the discretion of the attending physician.

In some embodiments, the additional therapy is the administration of small molecule enzymatic inhibitor or anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation. In some embodiments, the additional therapy is therapy targeting PBK/AKT/mTOR pathway, HSP90 inhibitor, tubulin inhibitor, apoptosis inhibitor, and/or chemopreventative agent. The additional therapy may be one or more of the chemotherapeutic agents known in the art.

Various combinations may be employed. For the example below a T cell therapy is "A" and an additional therapeutic agent is "B":

| | | | | | |
|---|---|---|---|---|---|
| A/B/A | B/A/B | B/B/A | A/A/B | A/B/B | B/A/A |
| A/B/B/B | B/A/B/B | B/B/B/A | B/B/A/B | A/A/B/B | A/B/A/B |
| A/B/B/A | B/B/B/A | B/A/B/A | B/A/A/B | A/A/A/B | B/A/A/A |
| A/B/A/A | A/A/B/A | | | | |

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy.

1. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammaI1 and calicheamicin omegaI1); dynemicin, including dynemicin A; bisphosphonates, such as clodronate; an esperamicin; as well as neocarzinostatin chromophore and related chromoprotein enediyne antibiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DMFO); retinoids, such as retinoic acid; capecitabine; carboplatin, procarbazine, plicomycin, gemcitabien, navelbine, farnesyl-protein tansferase inhibitors, transplatinum, and pharmaceutically acceptable salts, acids, or derivatives of any of the above.

2. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

3. Immunotherapy

The skilled artisan will understand that additional immunotherapies may be used in combination or in conjunction with methods of the embodiments. In the context of cancer treatment, immunotherapeutics, generally, rely on the use of immune effector cells and molecules to target and destroy cancer cells. Rituximab (RITUXAN®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve as a targeting agent. Alternatively, the effector may be a lymphocyte carrying a surface molecule that interacts, either directly or indirectly, with a tumor cell target. Various effector cells include cytotoxic T cells and NK cells Antibody-drug conjugates have emerged as a breakthrough approach to the development of cancer therapeutics. Cancer is one of the leading causes of deaths in the world. Antibody-drug conjugates (ADCs) comprise monoclonal antibodies (MAbs) that are covalently linked to cell-killing drugs. This approach combines the high specificity of MAbs against their antigen targets with highly potent cytotoxic drugs, resulting in "armed" MAbs that deliver the payload (drug) to tumor cells with enriched levels of the antigen (Carter et al., 2008; Teicher et al., 2014; Leal et al., 2014). Targeted delivery of the drug also minimizes its exposure in normal tissues, resulting in decreased toxicity and improved therapeutic index. The approval of two ADC drugs, ADCE-TRIS® (brentuximab vedotin) in 2011 and KADCYLA® (trastuzumab emtansine or T-DM1) in 2013 by FDA validated the approach. There are currently more than 30 ADC drug candidates in various stages of clinical trials for cancer treatment (Leal et al., 2014). As antibody engineering and linker-payload optimization are becoming more and more mature, the discovery and development of new ADCs are increasingly dependent on the identification and validation of new targets that are suitable to this approach (Teicher et al., 2009) and the generation of targeting MAbs. Two criteria for ADC targets are upregulated/high levels of expression in tumor cells and robust internalization.

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., *Mycobacterium bovis, Plasmodium falciparum*, dinitrochlorobenzene, and aromatic compounds (U.S. Pat. Nos. 5,801,005 and 5,739,169; Hui and Hashimoto, 1998; Christodoulides et al., 1998); cytokine therapy, e.g., interferons α, β, and γ, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and monoclonal antibodies. e.g., anti-CD20, anti-ganglioside GM2, and anti-p185 (Hollander, 2012; Hanibuchi et al., 1998; U.S. Pat. No. 5,824,311). It is contemplated that one or more anti-cancer therapies may be employed with the antibody therapies described herein.

In some embodiments, the immunotherapy may be an immune checkpoint inhibitor. Immune checkpoints are regulators in the immune system that either turn up a signal (e.g., co-stimulatory molecules) or turn down a signal. Inhibitory checkpoints that may be targeted by immune checkpoint blockade include adenosine A2A receptor (A2AR), B7-H3 (also known as CD276), B and T lymphocyte attenuator (BTLA), cytotoxic T-lymphocyte-associated protein 4 (CTLA-4, also known as CD152), indoleamine 2,3-dioxygenase (IDO), killer-cell immunoglobulin (KIR), lymphocyte activation gene-3 (LAG3), programmed death 1 (PD-1), T-cell immunoglobulin domain and mucin domain 3 (TIM-3) and V-domain Ig suppressor of T cell activation (VISTA). In particular, the immune checkpoint inhibitors target the PD-1 axis and/or CTLA-4.

The immune checkpoint inhibitors may be drugs such as small molecules, recombinant forms of ligand or receptors, or, in particular, are antibodies, such as human antibodies (e.g., International Patent Publication WO2015016718; Pardoll, *Nat Rev Cancer,* 12(4): 252-64, 2012; both incorporated herein by reference). Known inhibitors of the immune checkpoint proteins or analogs thereof may be used, in particular chimerized, humanized or human forms of antibodies may be used. As the skilled person will know, alternative and/or equivalent names may be in use for certain antibodies mentioned in the present disclosure. Such alternative and/or equivalent names are interchangeable in the context of the present invention. For example it is known that lambrolizumab is also known under the alternative and equivalent names MK-3475 and pembrolizumab.

In some embodiments, the PD-1 binding antagonist is a molecule that inhibits the binding of PD-1 to its ligand binding partners. In a specific aspect, the PD-1 ligand binding partners are PDL1 and/or PDL2. In another embodiment, a PDL1 binding antagonist is a molecule that inhibits the binding of PDL1 to its binding partners. In a specific aspect, PDL1 binding partners are PD-1 and/or B7-1. In another embodiment, the PDL2 binding antagonist is a molecule that inhibits the binding of PDL2 to its binding partners. In a specific aspect, a PDL2 binding partner is PD-1. The antagonist may be an antibody, an antigen binding fragment thereof, an immunoadhesin, a fusion protein, or oligopeptide. Exemplary antibodies are described in U.S. Pat. Nos. 8,735,553, 8,354,509, and 8,008,449, all incorporated herein by reference. Other PD-1 axis antagonists for use in the methods provided herein are known in the art such as described in U.S. Patent Application No. US20140294898, US2014022021, and US20110008369, all incorporated herein by reference.

In some embodiments, the PD-1 binding antagonist is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. In some embodiments, the PD-1 binding antagonist is an immunoadhesin (e.g., an immunoadhesin comprising an extracellular or PD-1 binding portion of PDL1 or PDL2 fused to a constant region (e.g., an Fc region of an immunoglobulin sequence). In some embodiments, the PD-1 binding antagonist is AMP-224. Nivolumab, also known as MDX-1106-04, MDX-1106, ONO-4538, BMS-936558, and OPDIVO®, is an anti-PD-1 antibody described in WO2006/121168. Pembrolizumab, also known as MK-3475, Merck 3475, lambrolizumab, KEYTRUDA®, and SCH-900475, is an anti-PD-1 antibody described in WO2009/114335. CT-011, also known as hBAT or hBAT-1, is an anti-PD-1 antibody described in WO2009/101611. AMP-224, also known as B7-DCIg, is a PDL2-Fc fusion soluble receptor described in WO2010/027827 and WO2011/066342.

Another immune checkpoint that can be targeted in the methods provided herein is the cytotoxic T-lymphocyte-associated protein 4 (CTLA-4), also known as CD152. The complete cDNA sequence of human CTLA-4 has the Genbank accession number L15006. CTLA-4 is found on the surface of T cells and acts as an "off" switch when bound to CD80 or CD86 on the surface of antigen-presenting cells. CTLA4 is a member of the immunoglobulin superfamily that is expressed on the surface of Helper T cells and transmits an inhibitory signal to T cells. CTLA4 is similar to the T-cell co-stimulatory protein, CD28, and both molecules bind to CD80 and CD86, also called B7-1 and B7-2 respectively, on antigen-presenting cells. CTLA4 transmits an inhibitory signal to T cells, whereas CD28 transmits a stimulatory signal. Intracellular CTLA4 is also found in regulatory T cells and may be important to their function. T cell activation through the T cell receptor and CD28 leads to increased expression of CTLA-4, an inhibitory receptor for B7 molecules.

In some embodiments, the immune checkpoint inhibitor is an anti-CTLA-4 antibody (e.g., a human antibody, a humanized antibody, or a chimeric antibody), an antigen binding fragment thereof, an immunoadhesin, a fusion protein, or oligopeptide.

Anti-human-CTLA-4 antibodies (or VH and/or VL domains derived therefrom) suitable for use in the present methods can be generated using methods well known in the art. Alternatively, art recognized anti-CTLA-4 antibodies can be used. For example, the anti-CTLA-4 antibodies disclosed in: U.S. Pat. No. 8,119,129, WO 01/14424, WO 98/42752; WO 00/37504 (CP675,206, also known as tremelimumab; formerly ticilimumab), U.S. Pat. No. 6,207,156; Hurwitz et al. (1998) Proc Natl Acad Sci USA 95(17): 10067-10071; Camacho et al. (2004) J Clin Oncology 22(145): Abstract No. 2505 (antibody CP-675206); and Mokyr et al. (1998) Cancer Res 58:5301-5304 can be used in the methods disclosed herein. The teachings of each of the aforementioned publications are hereby incorporated by reference. Antibodies that compete with any of these art-recognized antibodies for binding to CTLA-4 also can be used. For example, a humanized CTLA-4 antibody is described in International Patent Application No. WO2001014424, WO2000037504, and U.S. Pat. No. 8,017,114; all incorporated herein by reference.

An exemplary anti-CTLA-4 antibody is ipilimumab (also known as 10D1, MDX-010, MDX-101, and Yervoy®) or antigen binding fragments and variants thereof (see, e.g., WOO 1/14424). In other embodiments, the antibody comprises the heavy and light chain CDRs or VRs of ipilimumab. Accordingly, in one embodiment, the antibody comprises the CDR1, CDR2, and CDR3 domains of the VH region of ipilimumab, and the CDR1, CDR2 and CDR3 domains of the VL region of ipilimumab. In another embodiment, the antibody competes for binding with and/or binds to the same epitope on CTLA-4 as the above-mentioned antibodies. In another embodiment, the antibody has at least about 90% variable region amino acid sequence identity with the above-mentioned antibodies (e.g., at least about 90%, 95%, or 99% variable region identity with ipilimumab).

Other molecules for modulating CTLA-4 include CTLA-4 ligands and receptors such as described in U.S. Pat. Nos. 5,844,905, 5,885,796 and International Patent Application Nos. WO1995001994 and WO1998042752; all incorporated herein by reference, and immunoadhesins such as described in U.S. Pat. No. 8,329,867, incorporated herein by reference.

4. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

5. Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

IV. ARTICLES OF MANUFACTURE OR KITS

An article of manufacture or a kit is provided comprising T cells expressing membrane-anchored IL-12 and/or NKG2D is also provided herein. The article of manufacture or kit can further comprise a package insert comprising instructions for using the adoptive T cells optionally in conjunction with an additional therapeutic agent (e.g., doxorubicin) to treat or delay progression of cancer in an individual or to enhance immune function of an individual having cancer. Any of the adoptive T cells and/or additional therapeutic agents described herein may be included in the article of manufacture or kits. In some embodiments, the adoptive T cells and additional therapeutic agent are in the same container or separate containers. Suitable containers include, for example, bottles, vials, bags and syringes. The container may be formed from a variety of materials such as glass, plastic (such as polyvinyl chloride or polyolefin), or metal alloy (such as stainless steel or hastelloy). In some embodiments, the container holds the formulation and the label on, or associated with, the container may indicate directions for use. The article of manufacture or kit may further include other materials desirable from a commercial and user standpoint, including other buffers, diluents, filters, needles, syringes, and package inserts with instructions for use. In some embodiments, the article of manufacture further includes one or more of another agent (e.g., a chemotherapeutic agent, and anti-neoplastic agent). Suitable containers for the one or more agent include, for example, bottles, vials, bags and syringes.

V. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Expression of IL-12 on T Cell Membrane Promotes T Cell Infiltration into Solid Tumors In order to achieve T cell membrane expression of IL12, an IL-12 membrane-anchored protein fusion gene was generated. Specifically, p35 was modified with a membrane-anchoring sequence (underlined). The construct of PCMV-hP35-TM-pA was followed by a standard p40 expressing unit. The p35 fusion protein sequence had the following amino acid sequence (SEQ ID NO:1):

```
MWPPGSASQPPPSPAAATGLHPAARPVSLQCRLSMCPARSLLLVATLVLL
HLSLARNLPVATPGMFPCLHHSQNLLRAVSNMLQKARQTLEFYPCTSEEI
DHEDITKDKTSTVEACLPLELTKNESCLNSRETSFITNGSCLASRKTSFM
MALCLSSIYEDLKMYQVEFKTMNAKLLMDPKRQIFLDQNMLAVIDELMQA
LNFNSETVPQKSSLEEPDFYKTKIKLCILLHAFRIRAVTIDRVMSYLNAS
GGGGSGGGGSIATGMVGALLLLLVVALGIGLFMRRRHIVRKRTLRRLLQ
EREL
```

The p40 protein had the following amino acid sequence (SEQ ID NO:4):

```
P40 subunit
MCHQQLVISWFSLVFLASPLVAIWELKKDVYVVELDWYPDAPGEMVVLTC
DTPEEDGITWTLDQSSEVLGSGKTLTIQVKEFGDAGQYTCHKGGEVLSHS
LLLLHKKEDGIWSTDILKDQKEPKNKTFLRCEAKNYSGRFTCWWLTTIST
DLTFSVKSSRGSSDPQGVTCGAATLSAERVRGDNKEYEYSVECQEDSACP
AAEESLPIEVMVDAVHKLKYENYTSSFFIRDIIKPDPPKNLQLKPLKNSR
QVEVSWEYPDTWSTPHSYFSLTFCVQVQGKSKREKKDRVFTDKTSATVIC
RKNASISVRAQDRYYSSSWSEWASVPCS
```

Figure 3:
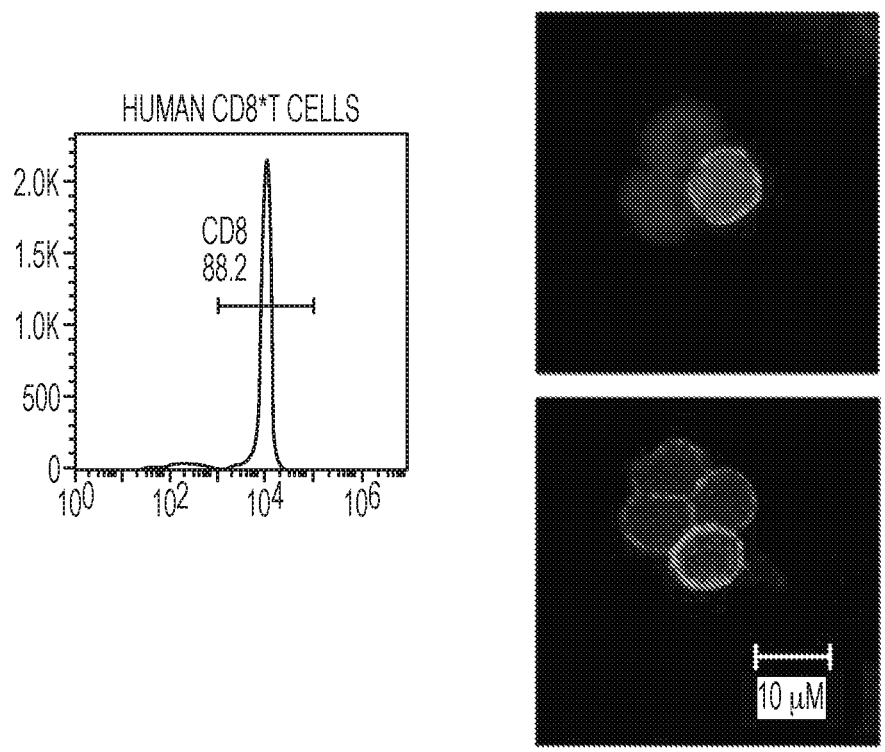
FIG. 3: Expression of attIL-12 on T cells 24 hours post transfection. The transfected T cells were spun on slides, fixed and stained for IL-12 p40 on the cell membrane. 7% of CD8⁺ T cells observed with membrane attIL-12 expression. Based on multiple independent transfection studies, the transfection efficiency varied in the range between 3-10%, but the therapeutic efficacy result is consistent within this range.

The attIL12 T cells were obtained by transfection of the IL12-membrane anchored protein fusion gene plasmid into CD8$^+$ T cells via electroporation using an electroporator. The expression duration of attIL12 after electroporation was detected at 4-6 hours and peaked in 24 hours but could last beyond 4 days for a small percentage of attIL12-T cells (Table 1). The expression of attIL12 on T cells 24 hours post transfection. The transfected T cells were spun on slides, fixed and stained for IL-12 p40 on the cell membrane. It was observed that 7% of the CD8$^+$ T cells expressed membrane attIL-12 (FIG. 3). Based on multiple independent transfection studies, the transfection efficiency varied in the range between 3-10%.

TABLE 1

| Transfection efficiency of attIL-12 plasmid. | |
|---|---|
| Time after transfection (h) | attIL-12 positive cells |
| 4 | 7% |
| 24 | 20% |
| 48 | 4.5% |
| 72 | 4% |
| 96 | 2.5% |

Figure 4:
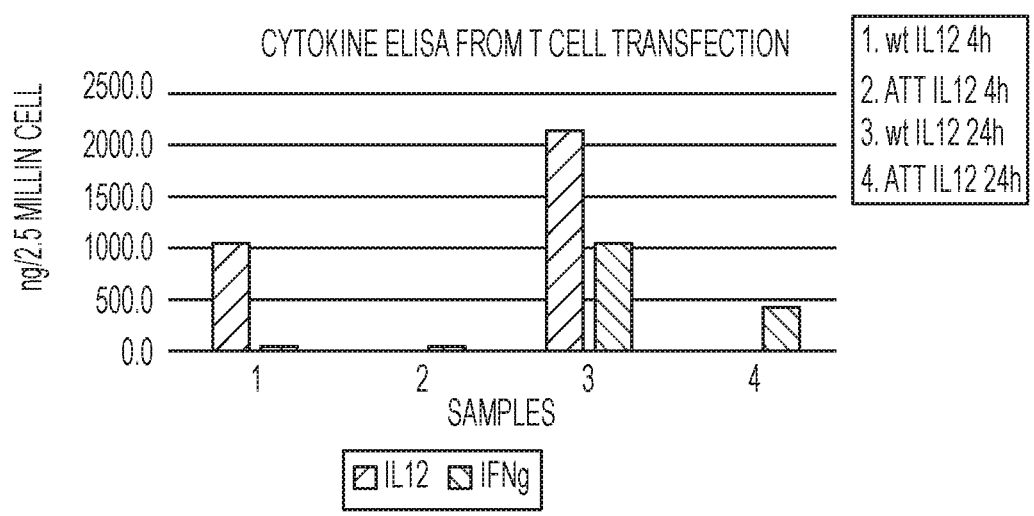
FIG. 4: T cells (2.5×10⁶) were transfected with 2 μg plasmid and incubated for 4 or 24 h in 1 ml RPMI/Click media. Medium was collected and assayed for the presence of IL12 and IFN-γ using ELISA. High levels of IL-12 was detected in the medium after wtIL-12 transfection, but not detectable by attIL-12 transfection at both 4 h and 24 h time points. WtIL-12 transfected T cells also produced a much higher level of IFNγ, compared to attIL-12 transfected T cells.
Figure 5:
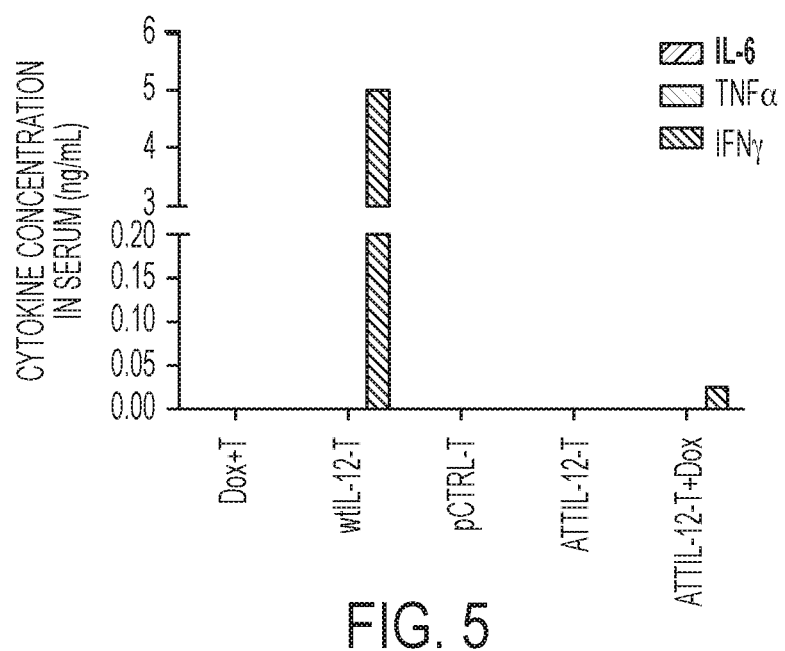
FIG. 5: Inflammatory cytokines in serum after indicated T cell transfer. Blood was collected 4 days after the second treatment, and tested for IL-6, TNFα and IFNγ levels in the serum using ELISA. IL-6 and TNFα are not detectable in any treatment groups. However, wtIL-12-T cell transfer induced a dramatically higher level of IFNγ in the blood, compared to attIL-12-T or attIL-12-T plus doxorubicin.

Next, studies were performed to characterize the attIL12 T cells. T cells ($2.5\times10^6$) were transfected with 2 µg plasmid and incubated 4 or 24 hours in 1 ml of RPMI/Click media. Medium was collected and assayed for the presence of IL12 and IFN-γ using ELISA. High levels of IL-12 was detected in the medium after wtIL-12 transfection, but was not detectable by attIL-12 transfection at both 4 h and 24 h time points. WtIL-12 transfected T cells also produced a slightly higher level of IFNγ as compared to the attIL-12 transfected T cells (FIG. 4).

Figure 6:
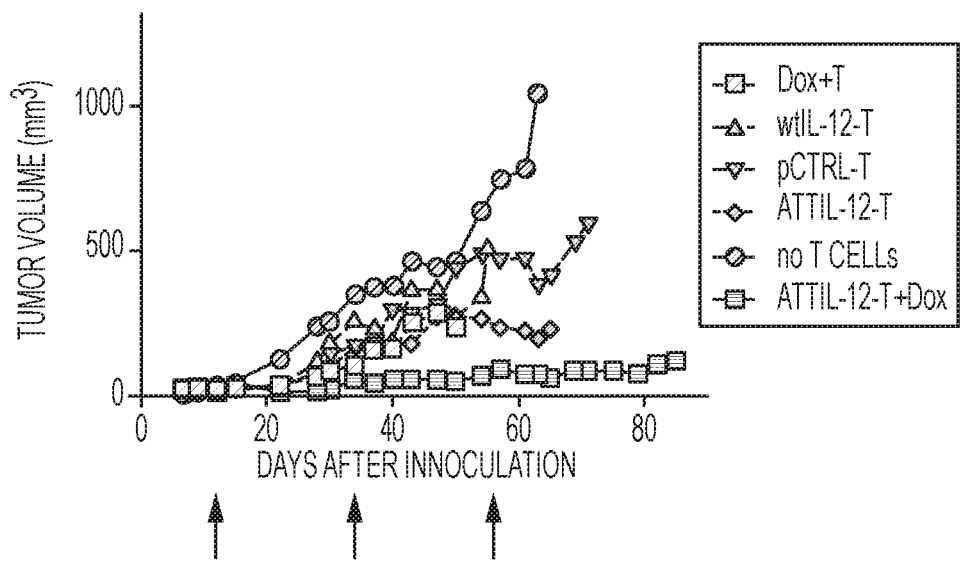
FIG. 6: Tumor volume of NSG mice inoculated with A549 cells subcutaneously, and subjected to the first described treatment (see FIG. 1) on day 12 after inoculation, followed by two more treatments at day 37 and 58. All mice received T cell treatment following the modification with control DNA (ctrlDNA), wildtype IL12 (wtIL12), or membrane anchored IL12 (attIL-12) unless specified.

Treatment with Doxorubicin Prior to attIL-12-T Cell Infusion Enhances Antitumor Therapeutic Efficacy:

NSG mice were inoculated with $5\times10^6$ A549 cells subcutaneously, and subjected to the first treatment on day 12 after inoculation, followed by two more treatments at days 37 and 58. All mice received T cell treatment ($2.5\times10^6$ T cells were administered for each infusion) following the modification with control DNA (ctrlDNA), wildtype IL12 (wtIL12), or membrane anchored IL12 (attIL12). Doxorubicin (Dox) was administered one day ahead of the T cell administration. Tumor volume was measured twice weekly. The results showed that attIL-12-T cell transfer plus Dox treatment effectively inhibited tumor development with prolonged survival time. Significantly, attIL12 T cell therapy significantly outperformed wtIL12 T cell therapy either without or with Dox treatment (FIG. 6).

A549 tumor sections were collected 3-5 mm from the tumor margin were subjected to anti-human CD3 and AF488 anti-rabbit antibody staining. The images represent the center of each section. T cell penetration was found in tumors treated with Dox followed by infusion of expanded T cells (Dox+T), infusion of attIL-12-T cells (attIL-12-T), and infusion of attIL-12 plus prior Dox treatment (attIL-12-T+Dox). Infusion of control T cells alone (pCtrl-T) or wildtype IL-12 modified T cells (wtIL-12-T) failed to have any detectable T cell penetration (FIG. 1).

Figure 2:
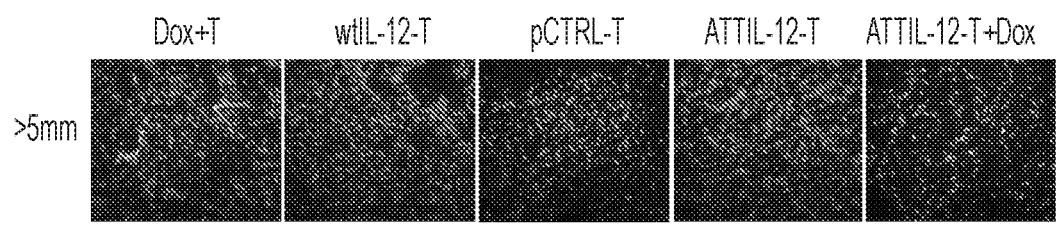
FIG. 2: A549 tumor sections which were collected more than 5 mm away from the tumor margin and toward the center of tumors were subjected to T cell staining. The images represent the center of each section. Only attIL-12-T cell transfer plus prior doxorubicin treatment showed deep tumor infiltration of the infused T cells.

A549 tumor sections which were collected more than 5 mm away from the tumor margin and toward the center of tumors were subjected to T cell staining. Only attIL-12-T cell transfer plus prior doxorubicin treatment showed deep tumor infiltration of the infused T cells (FIG. 2).

AttIL-12-T Cell Infusion can Reduce the Cytotoxic Cytokines Induced by wtIL-12:

Inflammatory cytokines were measured in the serum after T cell transfer. Blood was collected 4 days after the second treatment, and tested for IL-6, TNFα and IFNγ levels in the serum using ELISA. IL-6 and TNFα were not detectable in any treatment groups. However, wtIL-12-T cell transfer induced a dramatically higher level of IFNγ in the blood, compared with attIL-12-T or attIL-12-T plus doxorubicin. Thus, attIL-12 also reduces the risk of cytokine storm because attIL12 T cell do not induce the storm trigger IFNγ. Importantly, IFNγ also induces PD-L1 expression, which inhibits T cell function.

Figure 9:
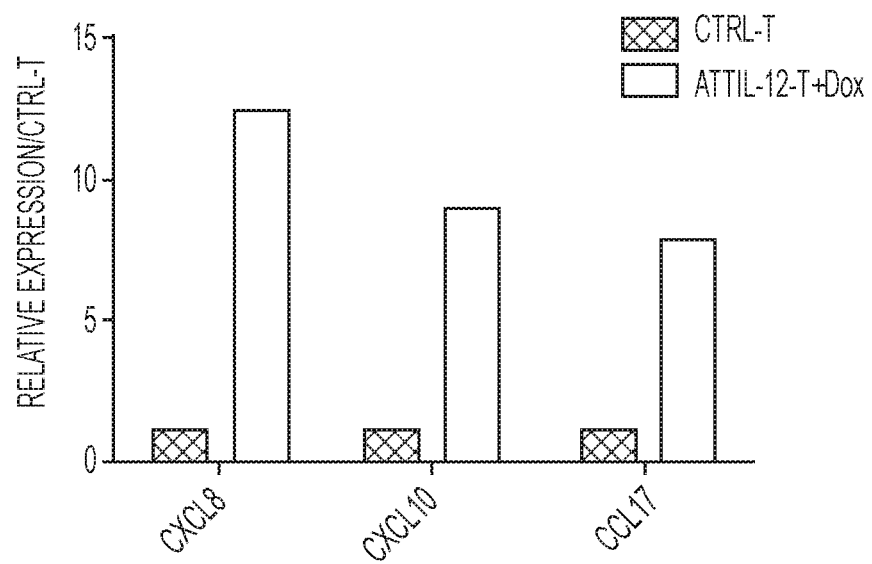
FIG. 9: A549 tumors were tested for mRNA expression of T cell attracting chemokines after the treatment of control or attIL-12-T cells plus doxorubicin. CXCL9, CXCL10 and CCL17 were dramatically induced in tumors by attIL-12-T cells plus doxorubicin. The chemokine induction accounts for T cell penetration into solid tumors.
Figure 10:
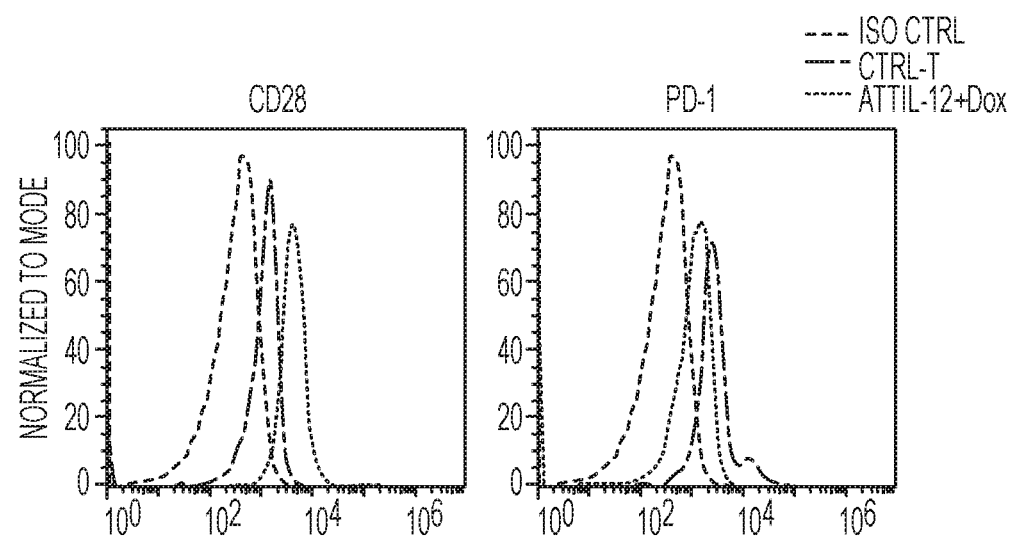
FIG. 10: PDX tumors after ctrl-T cells or attIL-12-T cells plus doxorubicin were subjected to flow cytometry to test the expression of CD28 and PD-1 on tumor infiltrated lymphocytes. Compared to ctrl-T cells treatment, attIL-12-T cells plus doxorubicin induced costimulatory receptor CD28 expression, and simultaneously reduced checkpoint regulator PD-1, increasing the ratio of costimulatory/coinhibitory receptors on infiltrated lymphocytes.
Figure 11:
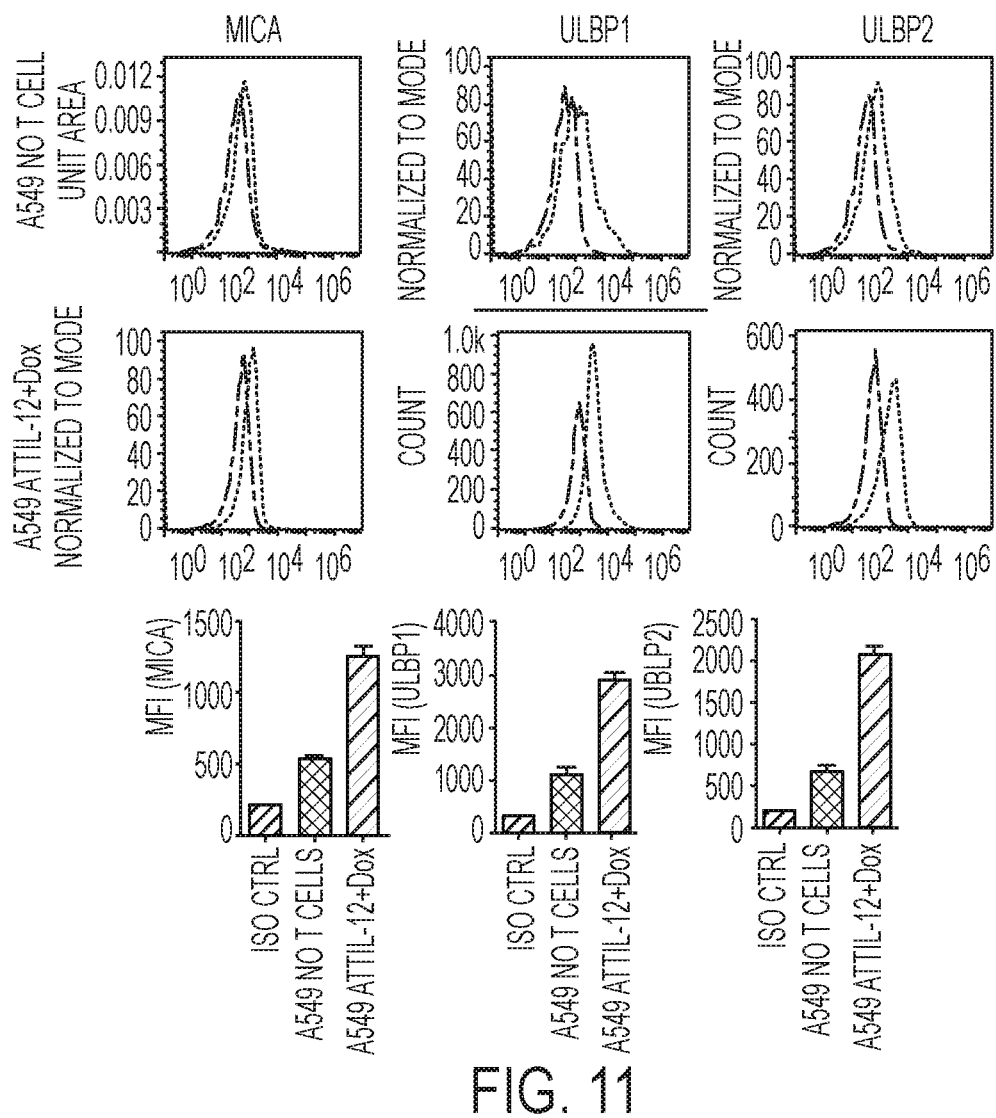
FIG. 11: A549 tumor cells were dissociated from tumors with or without two administrations of attIL-12-T cell infiltration plus doxorubicin, and were subsequently subjected to flow cytometry to test the expression of NKG2D ligands MICA, ULBP1 and ULBP2 on the tumor cell membrane. The treatment induced expression of NKG2D ligands on tumor cells, which could enhance the NKG2D immune surveillance.

A549 tumors were tested for mRNA expression of T cell attracting chemokines after with treatment of control or attIL-12-T plus doxorubicin. CXCL9, CXCL10 and CCL17 were dramatically induced in tumors by attIL-12-T plus doxorubicin (FIG. 9). The chemokine induction accounts for T cell penetration into solid tumors.

Figure 7:
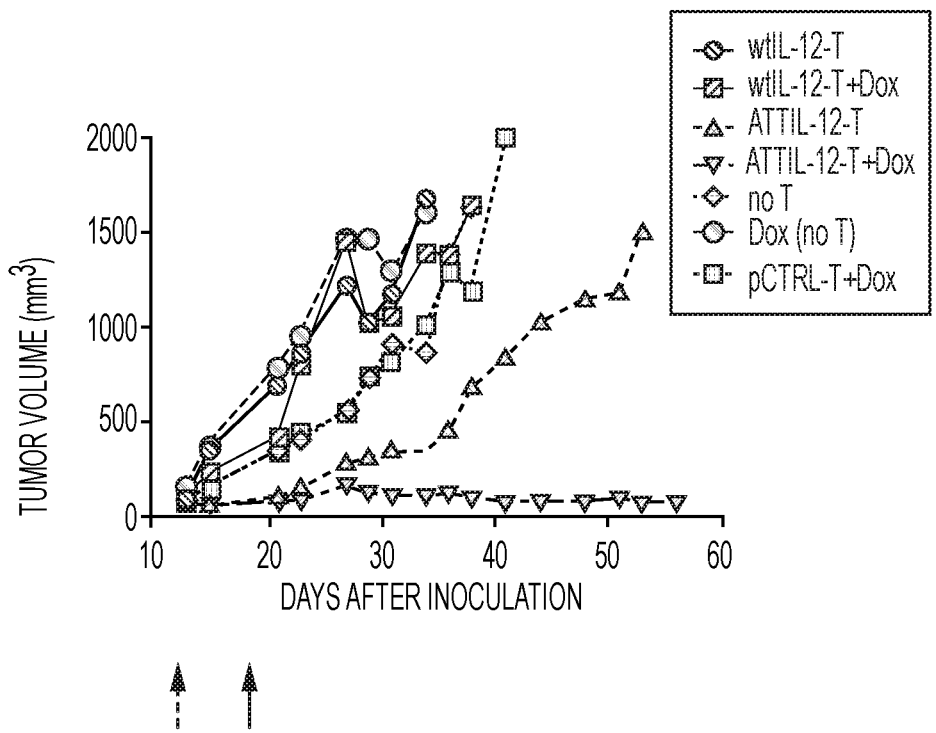
FIG. 7: Tumor volume of nude mice implanted with colon cancer PDX tumors subcutaneously, and subjected to the first described treatment when tumors reached 6-8 mm in diameter, followed by one more treatment on Day 28. All mice received T cell treatment following modification with control DNA (ctrlDNA), wildtype IL12 (wtIL-12), or membrane anchored IL12 (attIL-12) unless specified.

AttIL12 T Cell Infusion Plus Doxorubicin Results in Regression of Large (6-8 mm) and Aggressive Solid PDX Tumors:

Nude mice were implanted with colon cancer PDX tumors subcutaneously, and subjected to the first treatment when tumors were 6-8 mm in diameter, followed by one more treatment on Day 28. All mice received T cell treatment following the modification with control DNA (ctrlDNA), wildtype IL12 (wtIL12), or membrane-anchored IL-12 (attIL12). Doxorubicin (Dox) was administered one day ahead of the T cell administration. Tumor volume was measured twice weekly. The results showed that attIL-12-T cell transfer plus Dox treatment effectively inhibited tumor development with a prolonged survival time (FIG. 7). It was observed that a minimum of 3-20% attIL-12 positive T cells in each administration were needed for achieving solid tumor penetration.

Figure 8:
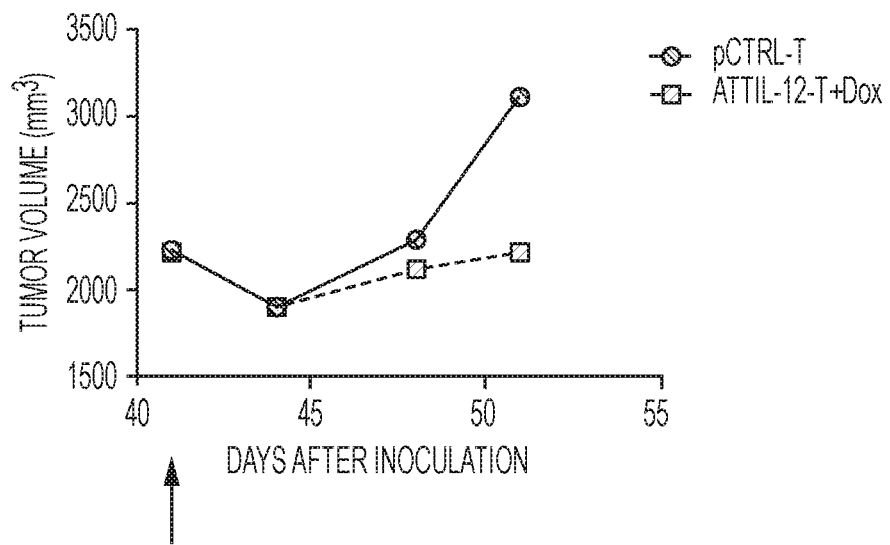
FIG. 8: Extra-large (16-18 mm in diameter) PDX tumors were subjected to control T cells or attIL-12-T cells plus doxorubicin. Compared to the control T cell therapy alone, attIL-12-T cells plus doxorubicin treatment stabilized tumor progression.

AttIL-12-T Cell Infusion ($1\times10^7$ Cells) Plus Doxorubicin can Stabilize Extra-Large (16-18 mm) PDX Tumors:

Extra-large (16-18 mm in diameter) PDX tumors were subjected to control T cell or attIL-12-T plus doxorubicin treatment. Compared to the control T cell therapy alone, attIL-12 T cells plus doxorubicin treatment stabilizes tumor progression (FIG. 8).

Improvement on T Cell Properties in Tumor Microenvironment by Induction of CD28 and Reduction of PD-1 on Infiltrated T Cells:

PDX tumors after ctrl T cell or attIL-12-T plus doxorubicin treatment were subjected to flow cytometry to test the expression of CD28 and PD-1 on tumor infiltrated lymphocytes. Compared to the ctrl-T treatment, attIL-12-T plus doxorubicin induced costimulatory receptor CD28 expression, and simultaneously reduced checkpoint regulator PD-1. In addition, there was induction of cytotoxic T cell ligands and receptors. Thus, doxorubicin upregulated T cell attracting cytokines. Likewise, the penetrated T cells have a low level of the exhausting marker Lag3 expression, which is in contrast to the high level of expression of this marker in the control group. Of note, NKG2D ligands are also high after the second treatment.

Thus, the attIL-12 T cell therapy IL-12 anchored on the T cell membrane was shown to have enhanced anti-tumor properties. In addition, it was discovered that the addition of doxorubicin (Dox) prior to (e.g., 16-24 hours) administration of attIL12 T cells significantly boosts attIL12 T cell penetration into solid tumors. This sequential administration of doxorubicin and attIL-12-T cell allows for both avoidance of T cell death and tumor penetration, which is collectively referred to as iTIL because the infiltrated T cells into tumors was induced by this treatment but not by naturally occurring T cells.

Example 2—Characterization of Lentiviral attIL-12 T Cells

Figure 12:
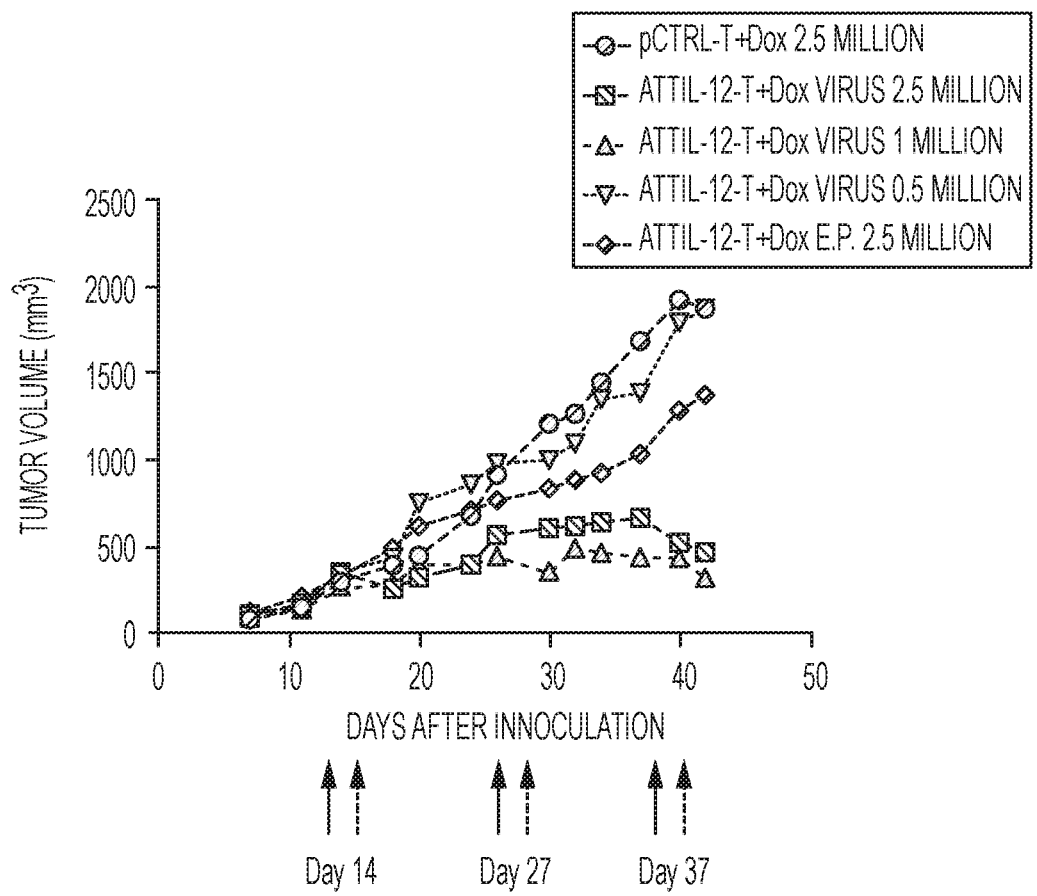
FIG. 12: Tumor volume of NSG mice inoculated with HT29 cells with or without administration of attIL-12 T cells plus doxorubicin. The doxorubicin was administered 3 times on Days 13, 27, and 36 followed by T cell transfer the next day (i.e., Days 14, 28, and 37). The lentiviral attIL-12 T cell plus doxorubicin treatment resulted in the highest inhibition of tumor volume.
Figure 13A:
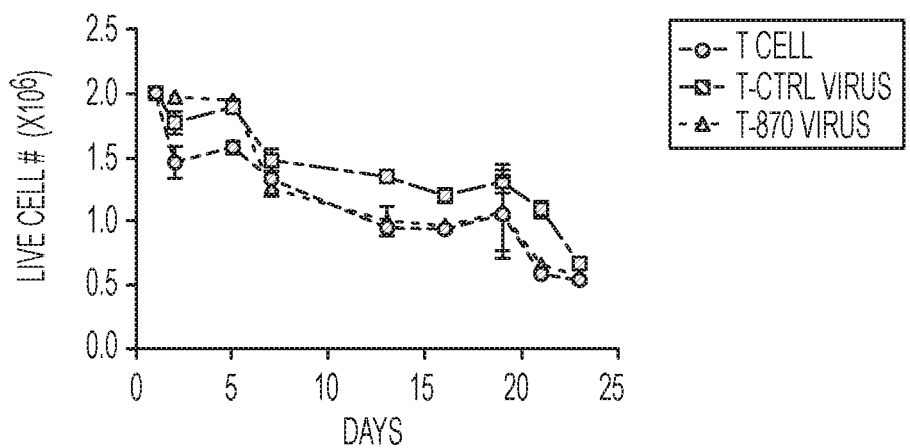
FIGS. 13A-13C: (A) T cell number, (B) viability, (C) and attIL-12 (T-870) expression on T cells during ex vivo culture in the absence of cytokines.
Figure 13B:
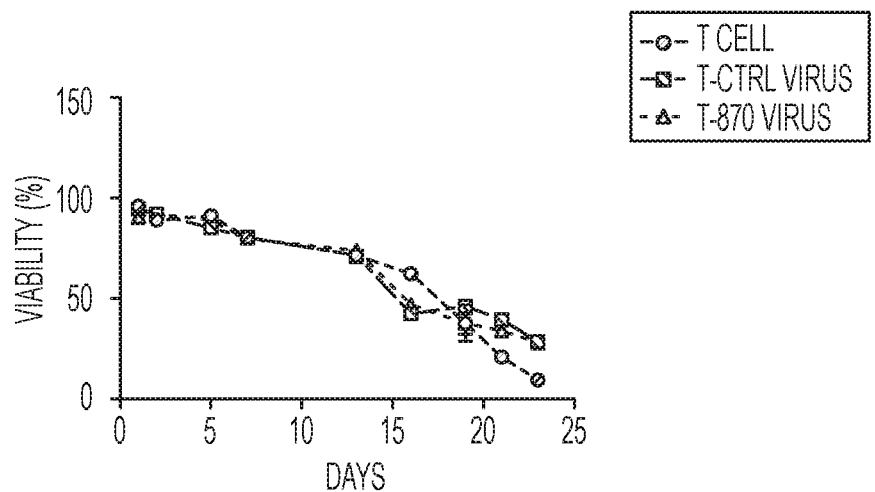
Figure 13C:
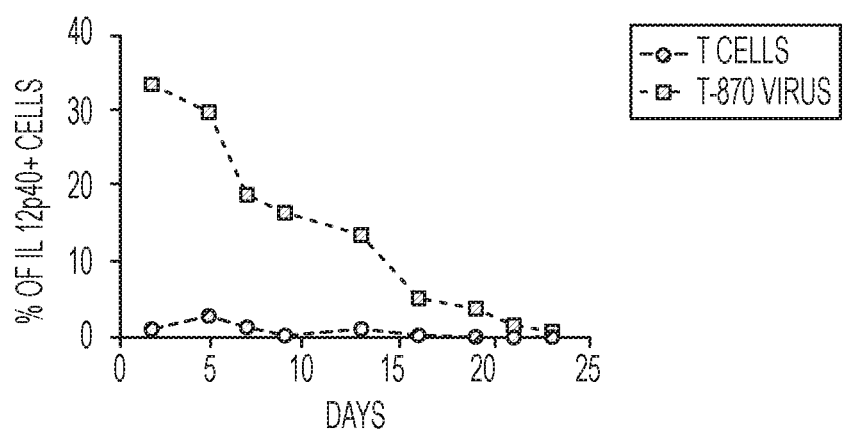

To further characterize the effectiveness of the attIL-12 T cells, a colon adenocarcinoma mice model was used. $5\times10^6$ HT29 cells were inoculated in NSG mice via subcutaneous injection. Treatment started when tumors reach 1.0 cm in diameter. Three administrations of doxorubicin were followed by T cell transfer on day 13/14, 27/28 and 36/37. T cells were infected with lenti-control or lenti-attIL-12 virus 24 h before T cell infusion. T cells were transfected with attIL-12 via electroporation 6 hours prior to infusion, pCtrl-T+Dox and 0.5 million attIL-12-T+Dox failed to delay tumor progression. By contrast, both 2.5 and 1 million of lentivirus attIL-12 infected T cells plus doxorubicin caused tumor regression (FIG. 12).

Figure 14:
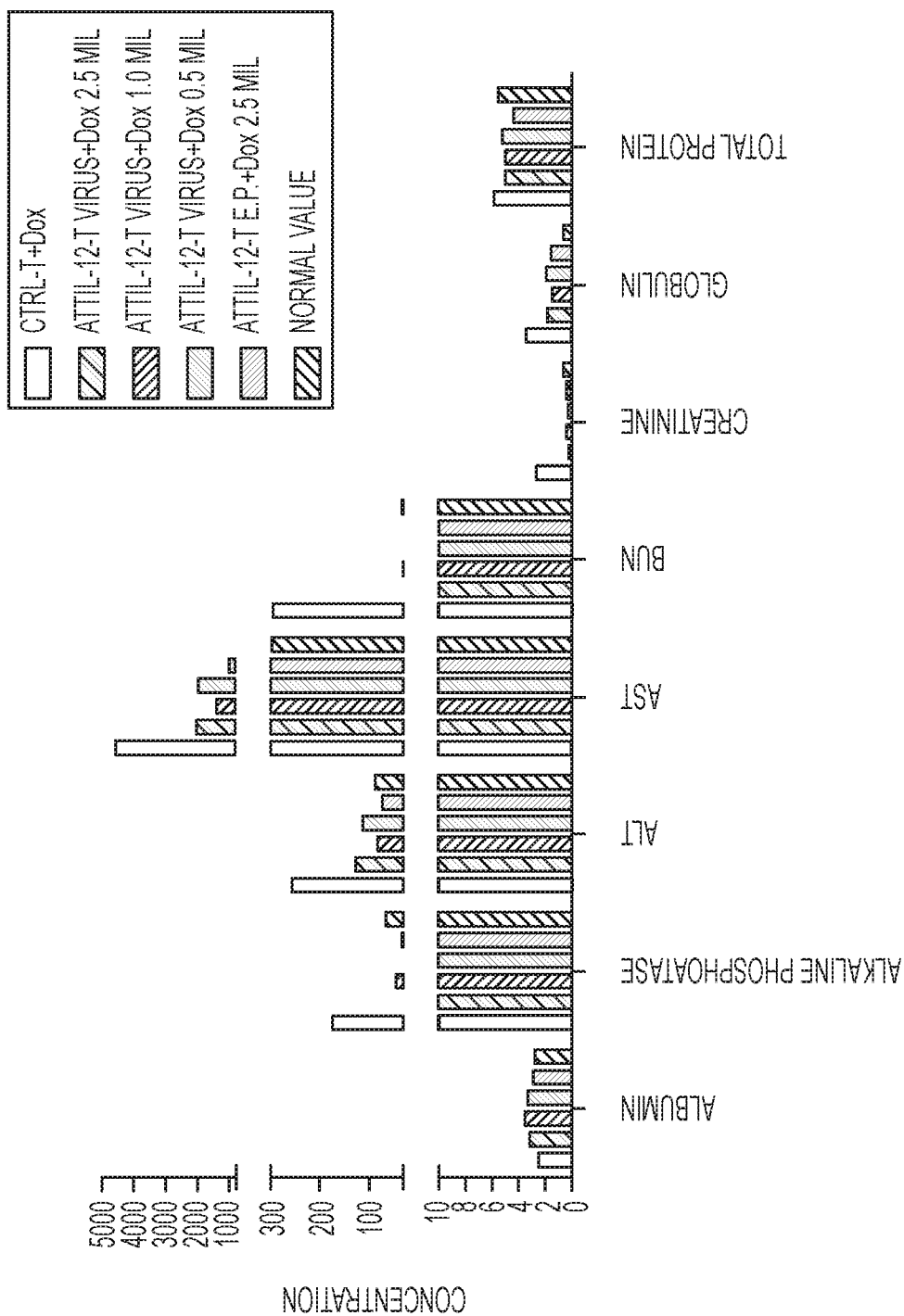
FIG. 14: Blood chemistry of mice bearing large HT29 tumors treated with control doxorubicin or doxorubicin plus attIL-12 T cells.
Figure 17A:
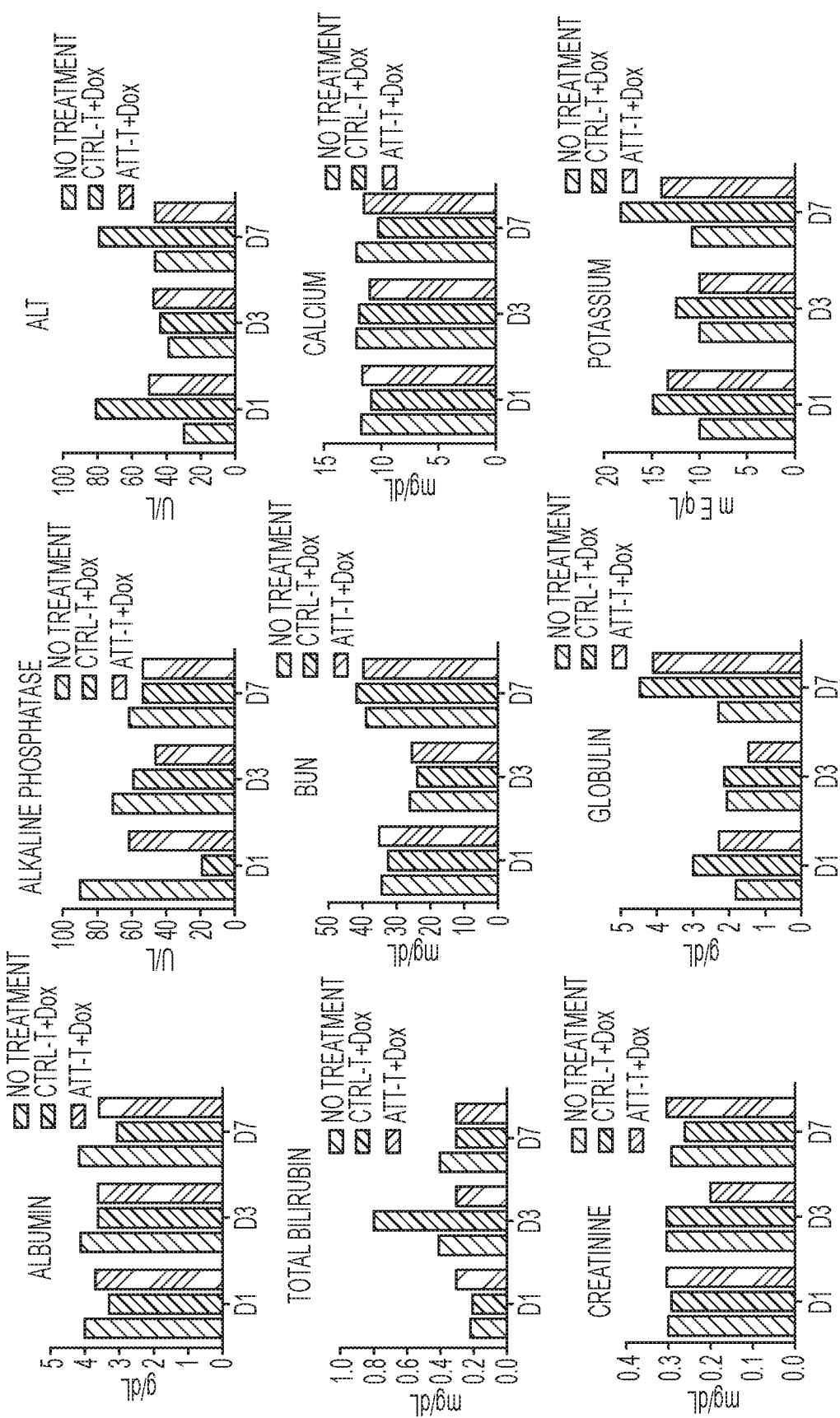
FIGS. 17A-17B: (A-B) Blood chemistry of mice with HT29 tumors treated with control or attIL-12 plus doxorubicin.
Figure 17B:
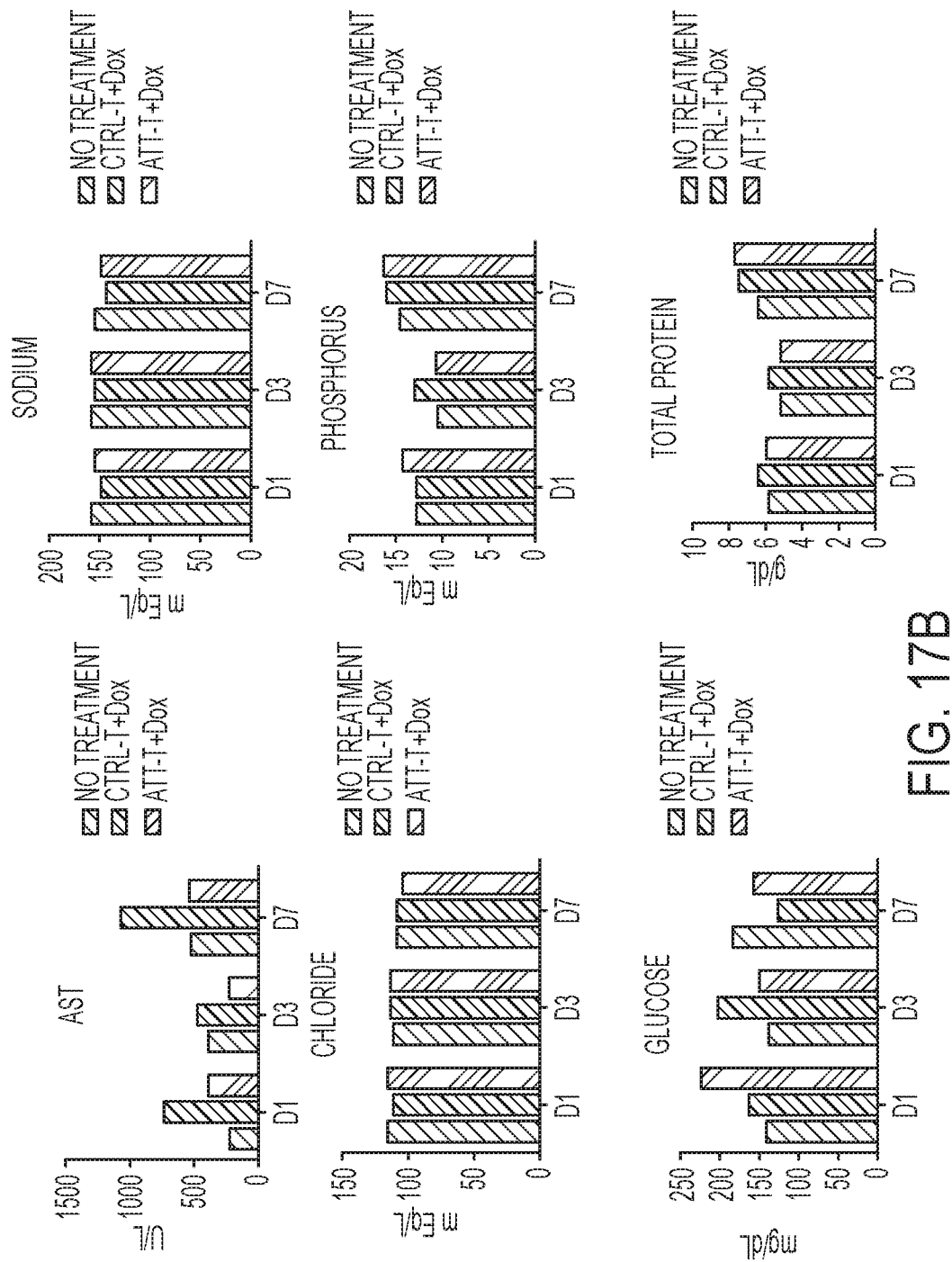

Blood chemistry analysis was performed on the mice bearing the large HT29 tumors including levels of albumin, alkaline phosphatase, ALT, AST, BUN, creatinine, globulin, and total protein (FIG. 14 and FIG. 17). While the attIL-12 T cell treated mice had slightly increased AST and globulin compared to normal baseline values, the control T cell treated mice has abnormally high levels of ALT, AST, BUN, and creatinine suggesting liver and renal damage. However, the attIL12 T cells treated mice were not observed to have the abnormally elevated levels indicating that the attIL-12 T cell does not cause liver or renal damage.

Figure 15:
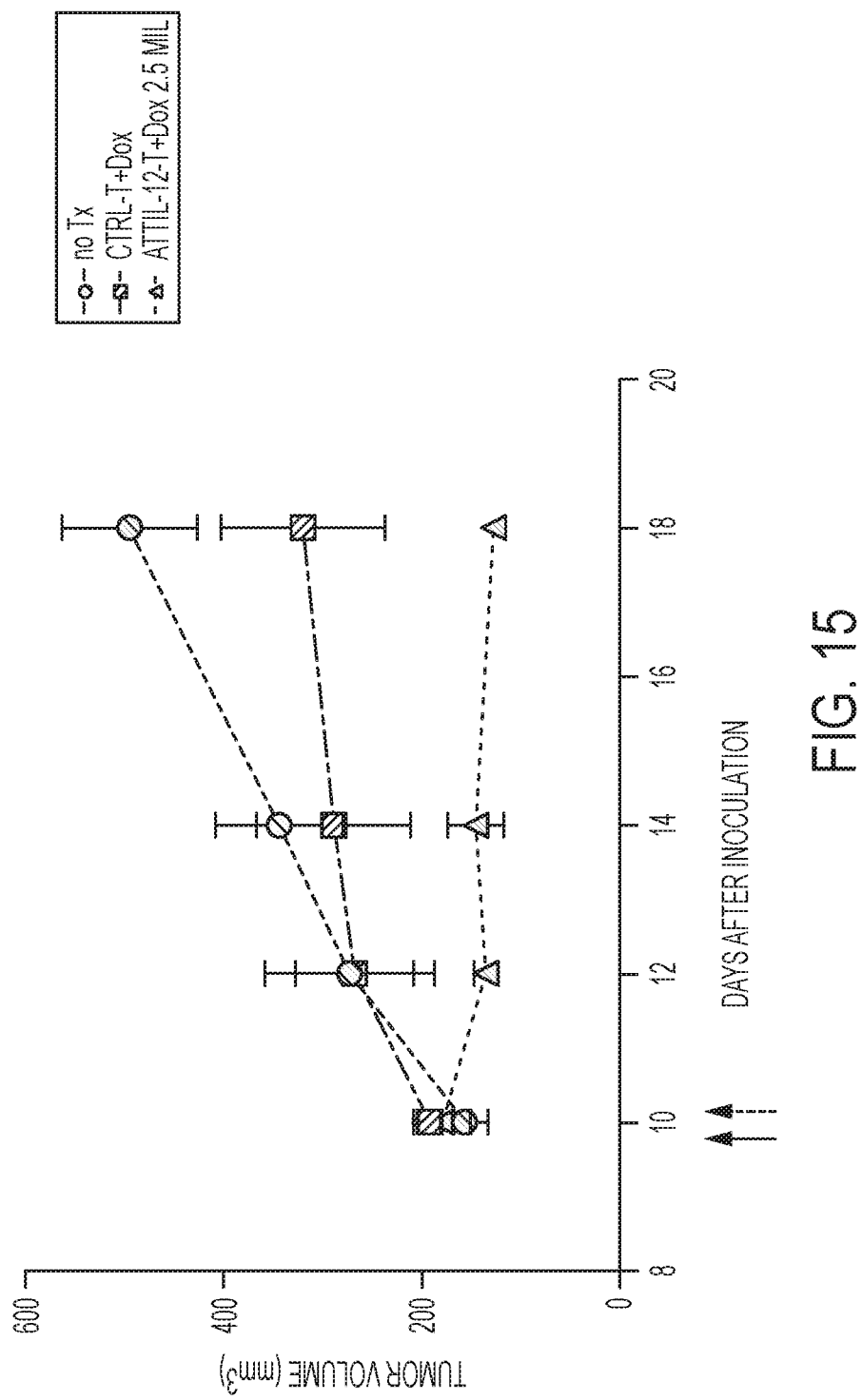
FIG. 15: Tumor volume in mice with HT29 tumors subjected to a single treatment of control, control virus+doxorubicin, or lentiviral attIL-12 T cells+doxorubicin. Mice were euthanized on Day 1, Day 3, and Day 7 after treatment to test T cell distribution.
Figure 16:
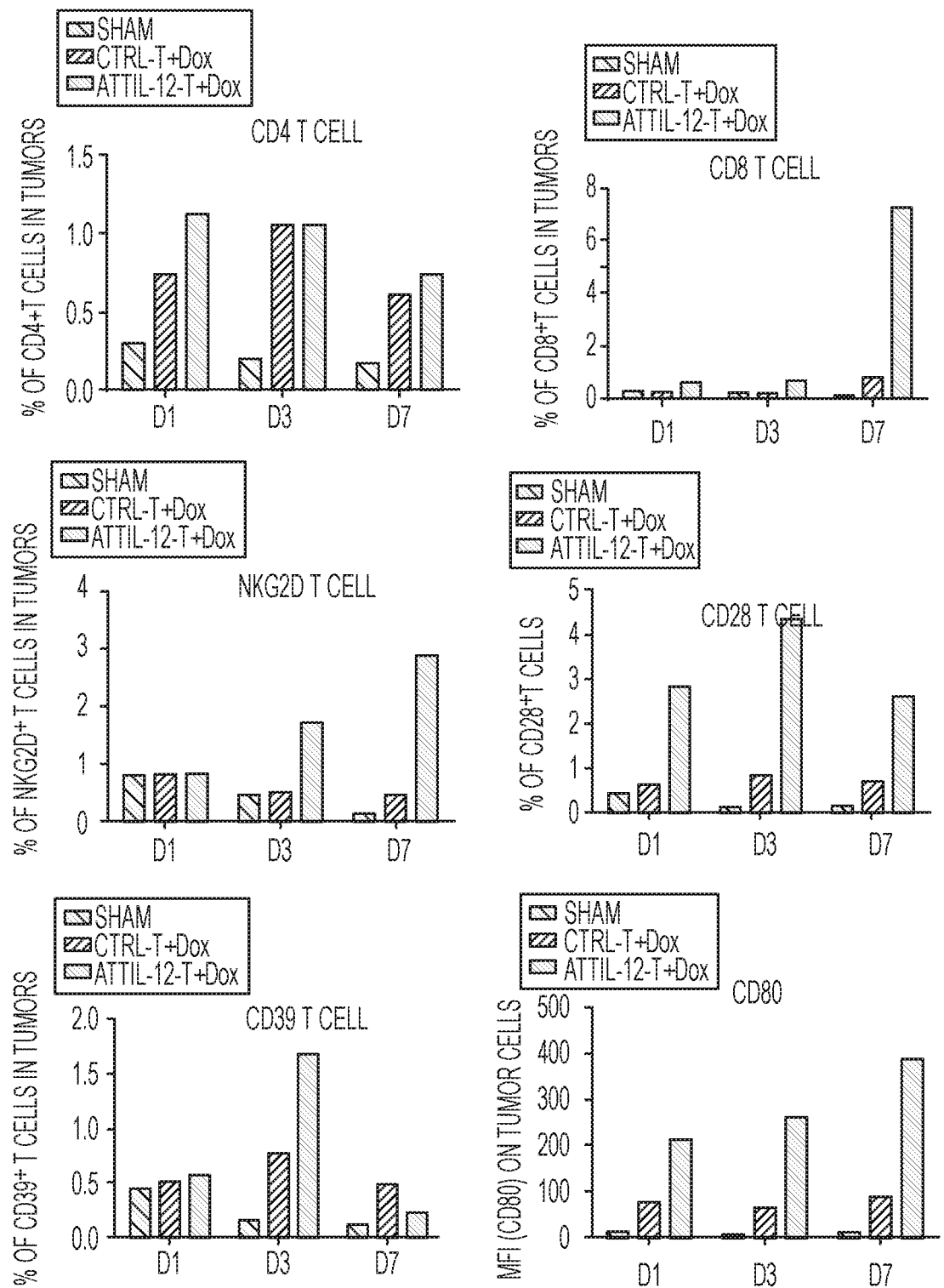
FIG. 16: CD4 T cells, CD8 T cells, NKG2D T cells, CD28 T cells, CD39 T cells, and CD80 expression was detected in tumors on Day 1, 3, and 7. The attIL-12 T cell plus doxorubicin treatment showed a high percentage of CD8 T cells at Day 7 as wells as NKG2D T cell at Days 3 and 7.

To test T cell distribution after infusion, HT29 tumor bearing mice were subject to a single treatment of sham, lenti-control-T+Dox and lenti-attIL-12-T+Dox. Mice were euthanized 1 day, 3 day and 7 days after the treatment, attIL-12-T+Dox induced tumor regression (FIG. 15) as observed in the earlier studies. Analysis of the T cell distribution showed that CD4, CD8 T cells, as well as NKG2D, CD28 and CD39 positive T cells and CD80 expression on tumor cells was detected in tumors on day 1, 3, and 7, attIL-12-T+Dox enhanced CD28 positive T cell accumulation in tumors as early as 1 day after the treatment, attIL-12-T+Dox also induced greatly increased accumulation of CD8 T cells in tumors as well as NKG2D positive T cells on day 7. CD39 was upregulated on T cells on day 3, but reduced to basal level on day 7. Interestingly, CD80 was dramatically induced on tumor cells by attIL-12-T+Dox as early as day 1 (FIG. 16).

Figure 18A:
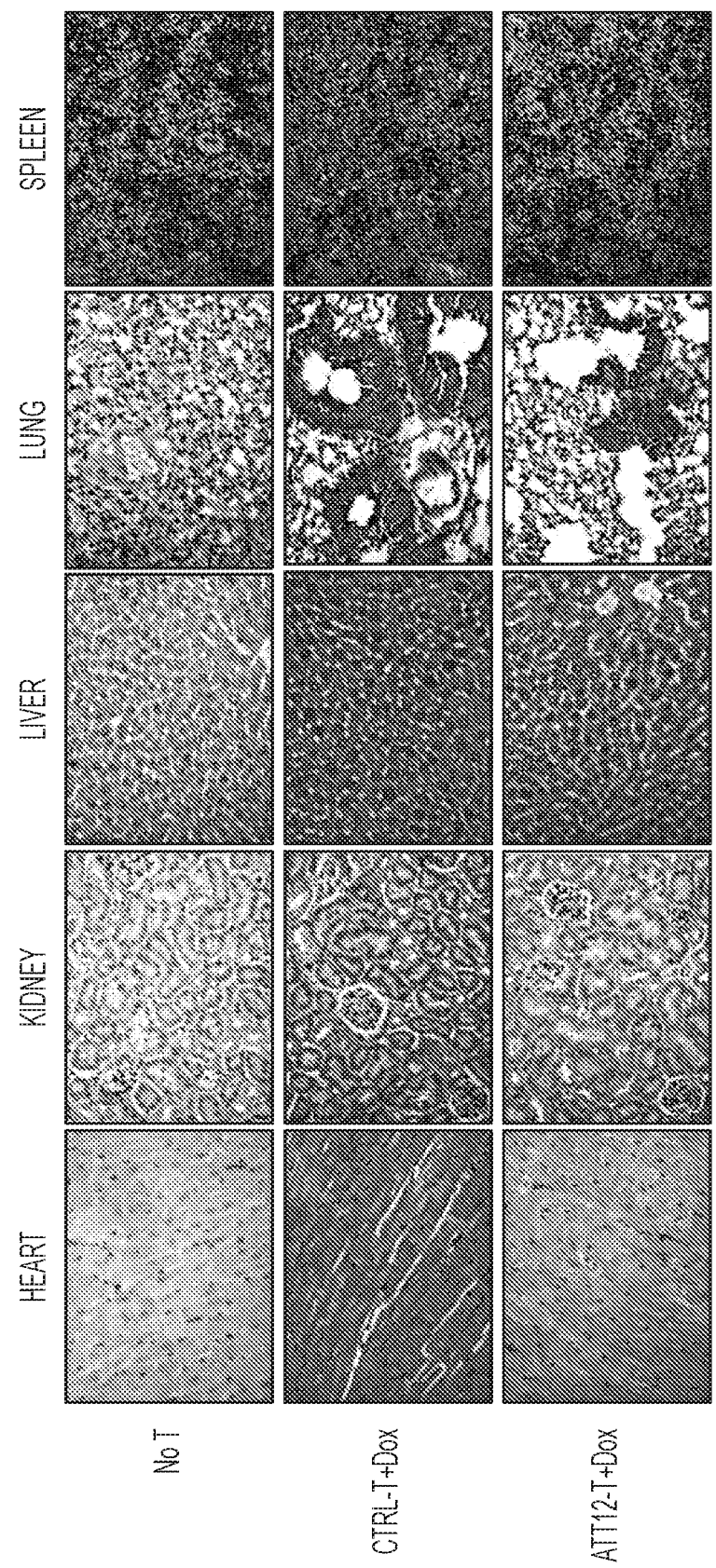
FIGS. 18A-18C: (A) T cell distribution Day 1 post administration in HT29 tumor-bearing mice. The control T cells plus doxorubicin treatment resulted in high accumulation of T cells in the lungs. Decreased accumulation of T cells was observed in the lungs of mice treated with attIL-12 T cells and doxorubicin as compared to the control T cells and doxorubicin. (B) T cell distribution Day 3 post administration in HT29 tumor-bearing mice. Only a few T cells were found in lungs from the attIL-12 T cell and doxorubicin treated mice. (C) T cell distribution Day 3 post administration in HT29 tumor-bearing mice. No T cells were found in lungs from the attIL-12 T cell and doxorubicin treated mice while there is positive staining for T cells in the lungs of mice treated with control T cells plus doxorubicin.
Figure 18B:
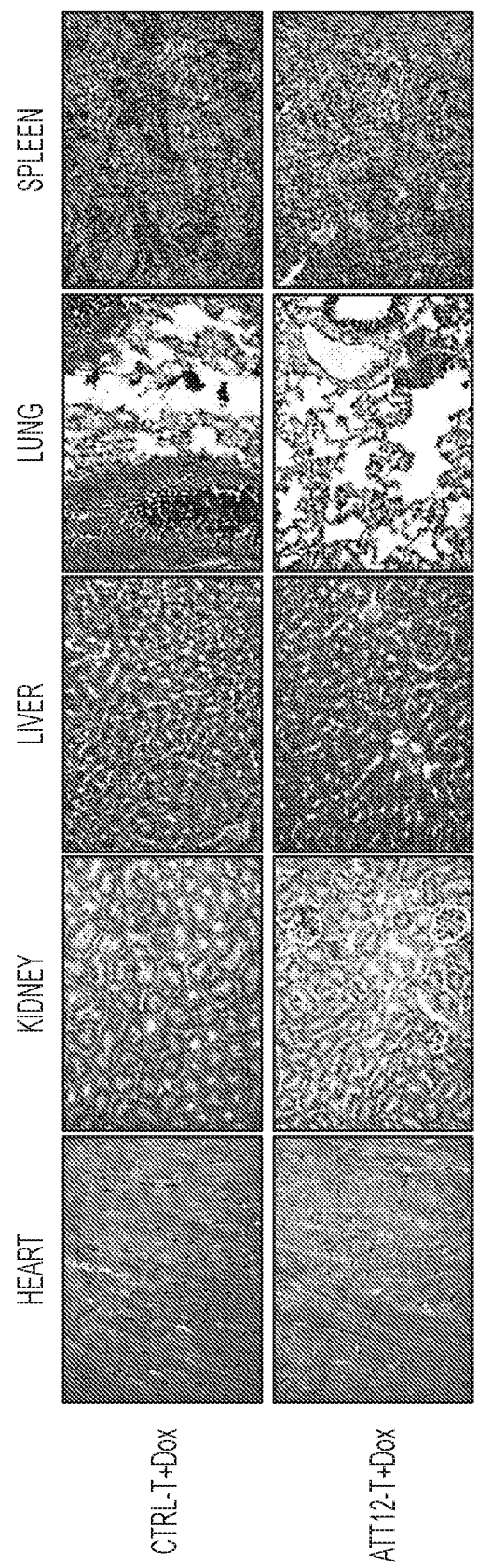
Figure 18C:
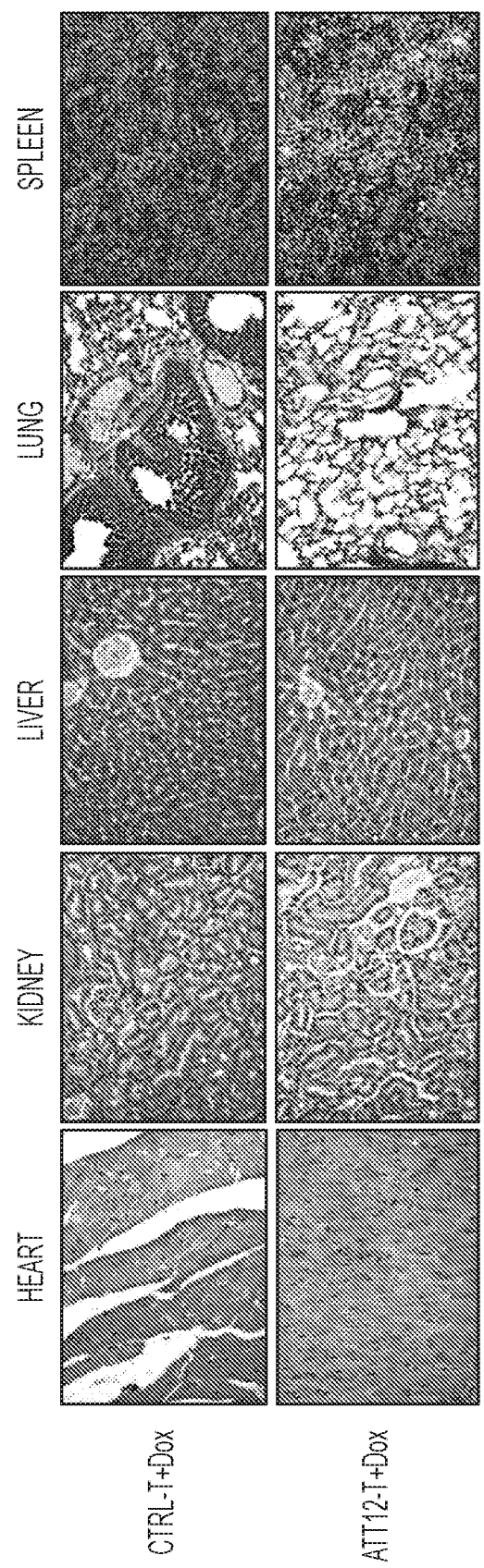
Figure 19:
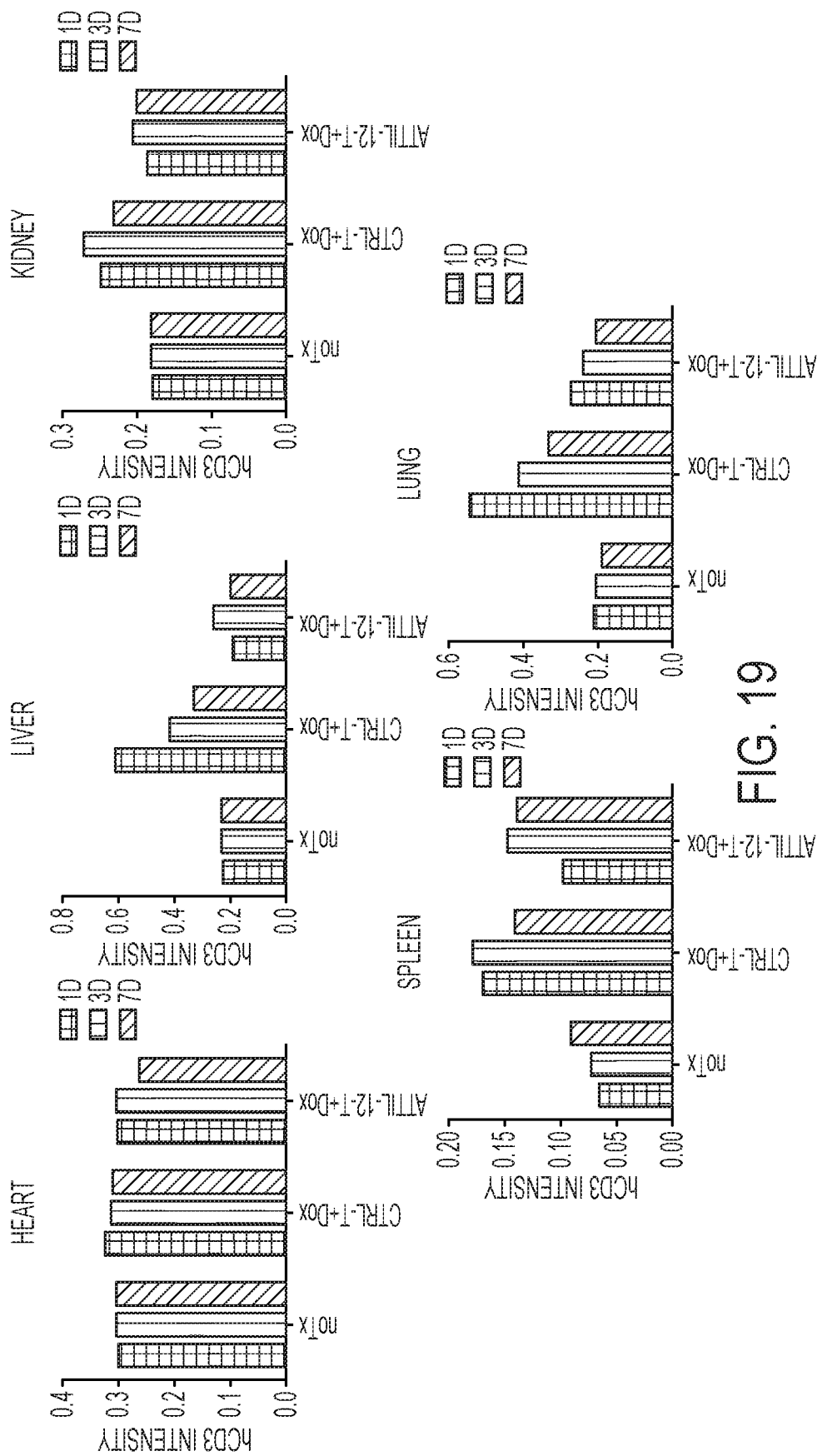
FIG. 19: T cell distribution in indicated organs on Days 1, 3, and 7 after treatment with control or attIL-12 T cells.

Immunohistochemistry analysis was also performed on the mice bearing HT29 tumors to determine T cell distribution in different organs. The lungs of the control T cell-treated mice showed substantial accumulation of T cells. On the other hand, the mice treated with attIL-12 T cells were observed to only have a few T cells accumulated in the lungs (FIG. 18 and FIG. 19). Indeed, no T cells were found in the lungs of the attIL-12 T cell-treated mice at Day 7 (FIG. 18C). Thus, there is a decreased risk of cytokine release syndrome (CRS) after treatment with the lentiviral attIL-12 T cells as compared to the control lentiviral T cell treatment.

Figure 20A:
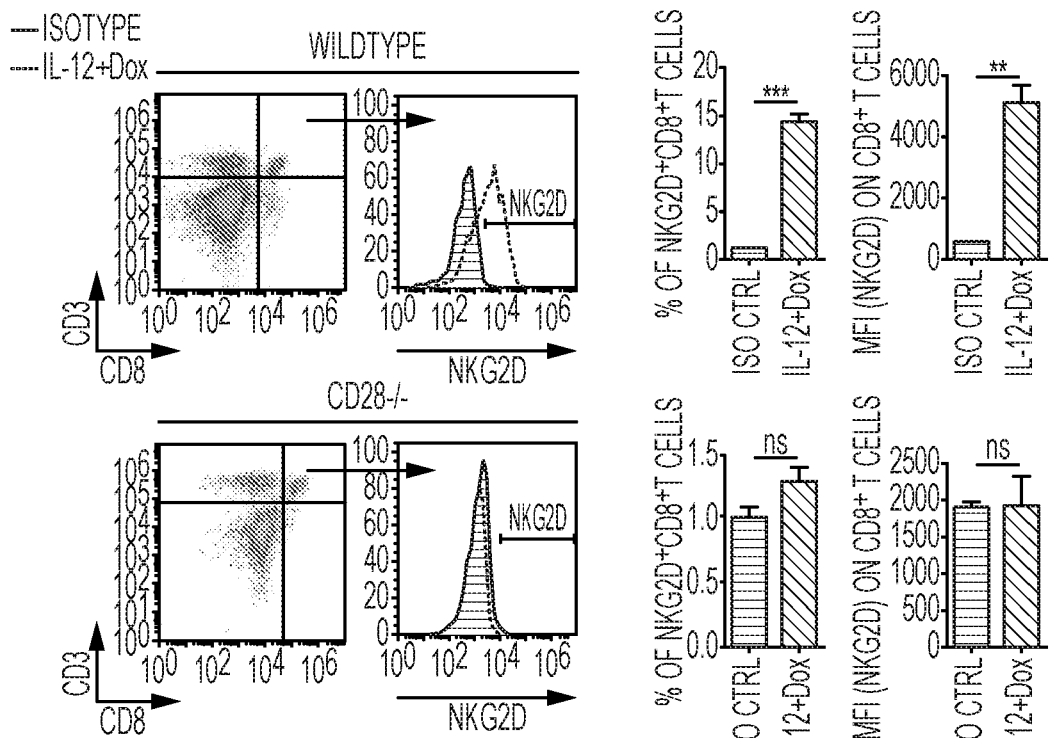
FIGS. 20A-20C: CD80 binding-mediated CD28 activation induces sustained expression of the NKG2D receptor on mouse $CD8^+$ T cells. (A) CD28 deficiency abolished the induction of NKG2D expression on $CD8^+$ T cells. LLC tumor bearing C57bl/6 mice (n=3) and $CD28^{+/+}$ mice were subjected to twice administrations (10 d apart) with IL-12 DNA (10 mg/mouse) plus doxorubicin (1 mg/kg). Four days after the second administration, splenocytes were isolated from C57bl/6 and CD28−/− mice, respectively, and stained with anti-mouse CD3, CD8+, and NKG2D antibodies to evaluate the median fluorescence intensity (MFI) and percentage of $CD8^+$ T cells expressing NKG2D. Treatment with IL-12 plus doxorubicin induced NKG2D expression in wild-type mice while there was no induction observed in CD28−/− mice. (B) Induction of NKG2D expression upon CD80 binding on $CD28^{+/+}$ $CD8^+$ T cells but not CD28−/− $CD8^+$ T cells. Splenocytes obtained from $CD29^{+/+}$ or CD28−/− mice were treated with anti-CD3 microbeads and control Fc or CD80-Fc (1 mg/mL). After 24 h of incubation, cells were stained with anti-$CD8^+$ and anti-NKG2D antibodies to evaluate the MFI and percentage of $CD8^+$ T cells expressing NKG2D. (C) Induction of sustained NKG2D expression on $CD8^+$ T cells by CD28 activation resulting from CD80 binding. Splenocytes obtained from $CD28^{+/+}$ C57BL/6 mice were stimulated with anti-CD3 microbeads and treated with control Fc or CD80-Fc. The $CD8^+$ T cells were stained for $CD8^+$ and NKG2D 1, 2, 3, 4, and 5 d after incubation for flow cytometric analysis. The bar graphs show the mean (±standard error of the mean [SEM]). The data are representative of three repeated experiments.
Figure 20B:
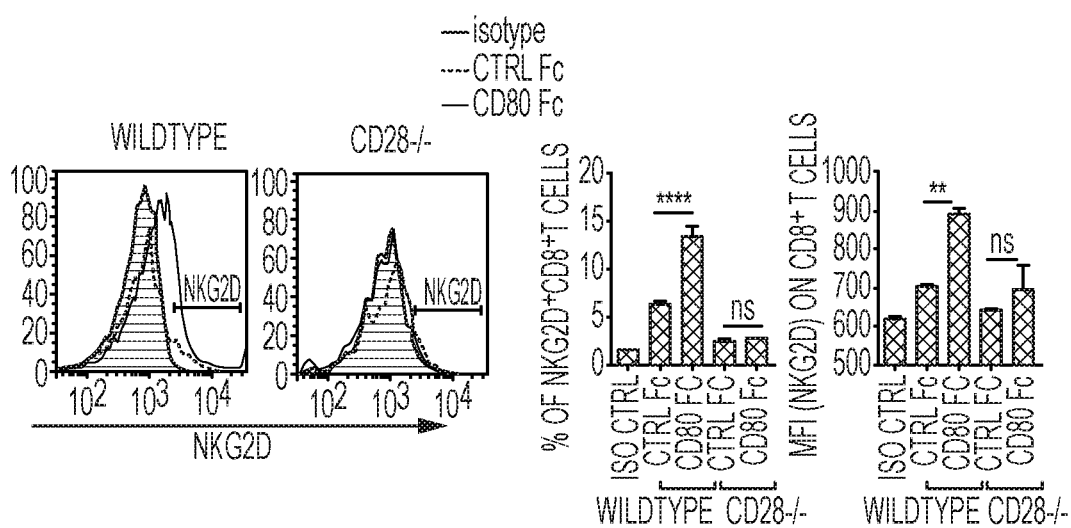
Figure 20C:
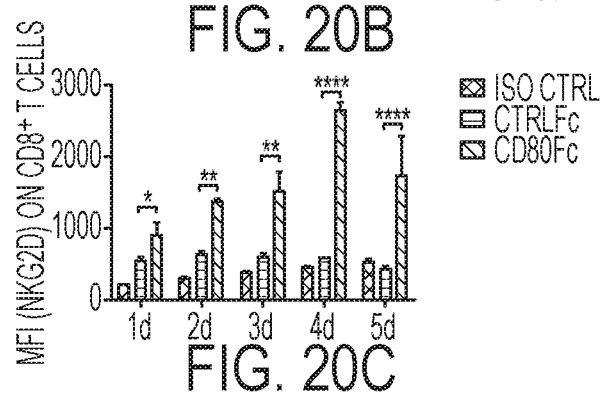
Figure 28:
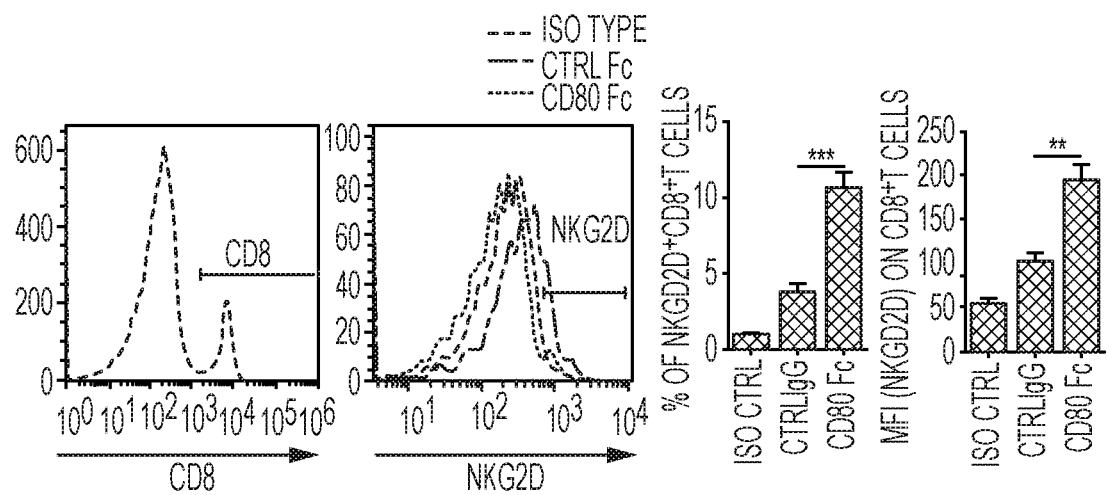
FIG. 28: Induction of NKG2D expression by CD80-Fc on splenic CD8$^+$ T cells obtained from LLC-bearing C57BL/6 mice in vivo. Mice with LLC (n=3) were given treatment with control Fc or CD80-Fc (10 □g) biweekly for 2 weeks. Splenocytes isolated from the LLC tumor bearing mice were stained for CD8 and NKG2D to evaluate the MFI and percentage of CD8+ T cells expressing NKG2D. The bar graphs show the mean (±standard error of the mean [SEM]). The data are representative of three repeated experiments.

Example 3—Regulation of NKG2D$^+$CD8$^+$ T Cell-Mediated Antitumor Immune Surveillance CD28 Activation in CD8$^+$ T Cells Triggers Increased NKG2D Expression:

Previous studies demonstrated that NKG2D expression could be induced on the surface of splenic CD8$^+$ T cells from tumor bearing mice by the treatment of IL-12 plus doxorubicin (FIG. 20A). However, the same treatment failed to augment the NKG2D$^+$CD8$^+$ T cell subpopulation in CD28−/− mice that bear the same tumor model (FIG. 20A). These observations led to that hypothesis that CD28 co-stimulation may play a critical role in the regulation of NKG2D expression on CD8$^+$ T cells. To test this hypothesis, splenocytes isolated from C57BL/6 and CD28−/− tumor-bearing mice were pre-treated with anti-CD3 microbeads and given treatment with control Fc or CD80-Fc recombinant protein, the physiological ligand for CD28, for 24 h. It was found that CD28 activation by CD80 significantly increased the NKG2D$^+$CD8$^+$ T-cell population. However, this was not duplicated in CD28− CD8$^+$ T cells (FIG. 20B), suggesting that CD28 activation can regulate the expression of NKG2D on CD8$^+$ T cells. The mouse NKG2D receptor is only expressed on a few activated mouse CD8$^+$ T cells transiently. Therefore, it was attempted to determine the duration of NKG2D expression on CD8$^+$ T cells. The naive CD8$^+$ T cells were pre-stimulated with anti-CD3 microbeads for 24 h, and then treated with control Fc or CD80-Fc for 1, 2, 3, 4, and 5 d. It was found that CD80-induced NKG2D expression peaked on day 4. By contrast, control Fc only induced the baseline expression of NKG2D on CD8$^+$ T cells (FIG. 20C). Moreover, administration of CD80-Fc to LLC tumor-bearing mice twice weekly for 2 weeks markedly increased NKG2D expression on splenic CD8$^+$ T cells (FIG. 28). These in vivo results further confirmed that CD28 activation induces sustained NKG2D expression on CD8$^+$ T cells.

Figures 21A, 21B:
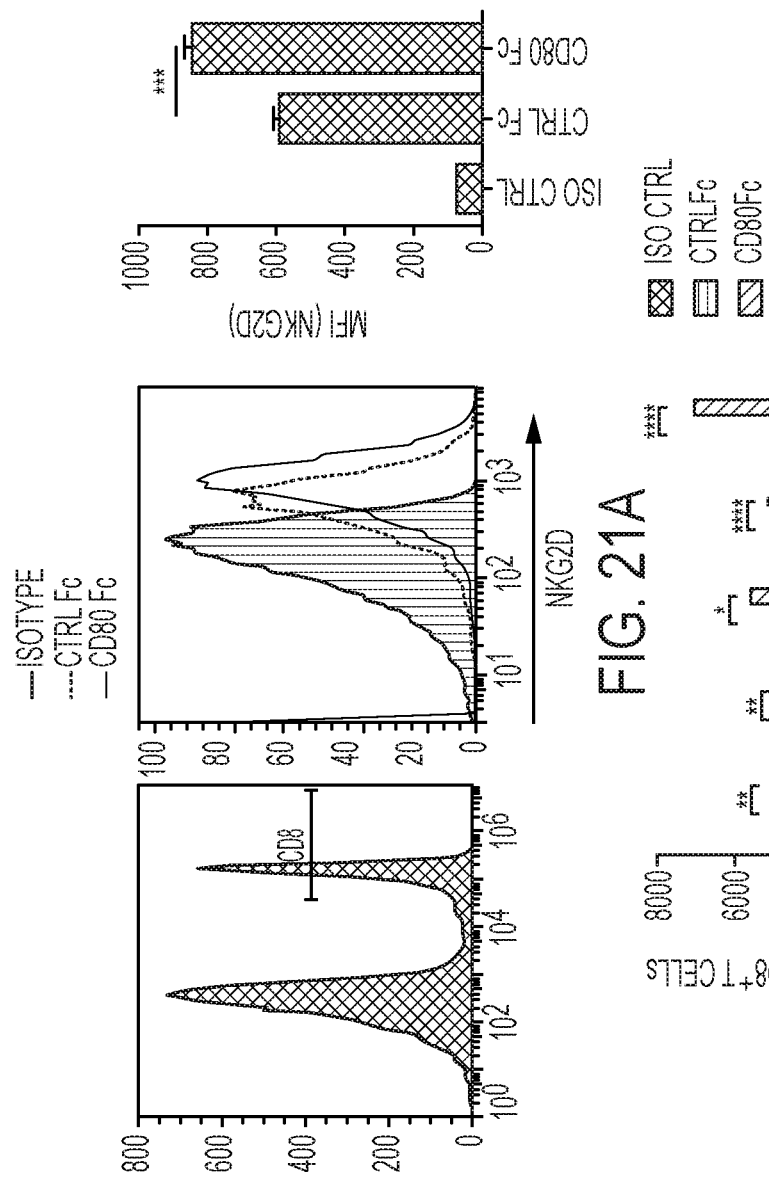
FIGS. 21A-21B: CD80 binding-mediated CD28 activation induces sustained human NKG2D receptor expression on $CD8^+$ T cells. (A) Induction of NKG2D expression on human $CD8^+$ T cells after CD28 activation. PBMCs isolated from healthy donors were stimulated with anti-CD3 microbeads and treated with control Fc or human CD80-Fc (1 mg/mL) for 24 h. The median (±SEM) of NKG2D expression on $CD8^+$ T cells is shown. (B) Induction of sustained NKG2D expression on $CD8^+$ T cells by binding of CD80-Fc to CD28. PBMCs obtained from healthy donors were treated as described in (A) for 1, 2, 3, 4 and 5 d, and stained for $CD8^+$ and NKG2D for flow cytometric analysis. The bar graphs show the mean MFI of NKG2D (±SEM) on $CD8^+$ T cells (n=3). The results represent those for five different healthy donors.

Unlike in mice, human NKG2D is more commonly expressed on CD8$^+$ T cells, NKG2D expression may be lost during ex vivo proliferation. To determine whether CD28 stimulation plays an important role in promoting human NKG2D expression on CD8$^+$ T cells, human T cells were isolated from healthy donors' PBMCs, pre-treated with anti-CD3 microbeads, and then stimulated with control Fc or human CD80-Fc. Despite high expression of the NKG2D receptor on human CD8$^+$ T cells, the treatment with CD80-Fc still markedly elevated NKG2D expression (FIG. 21A), which is consistent with what was observed in mice. Intriguingly, in the time-course study, it was found that prestimulation with anti-CD3 microbeads resulted in baseline expression of NKG2D on CD8$^+$ T cells, but in the absence of CD28 stimulation, the NKG2D$^+$CD8$^+$ T-cell population rapidly decreased from day 1 to day 4 (FIG. 21B). By striking contrast, the treatment with CD80-Fc induced sustained NKG2D expression on CD8$^+$ T cells and peaked on day 5 (FIG. 21B). These results supported the hypothesis that activation of CD28 is crucial for sustained NKG2D expression on CD8$^+$ T cells.

Figure 22A:
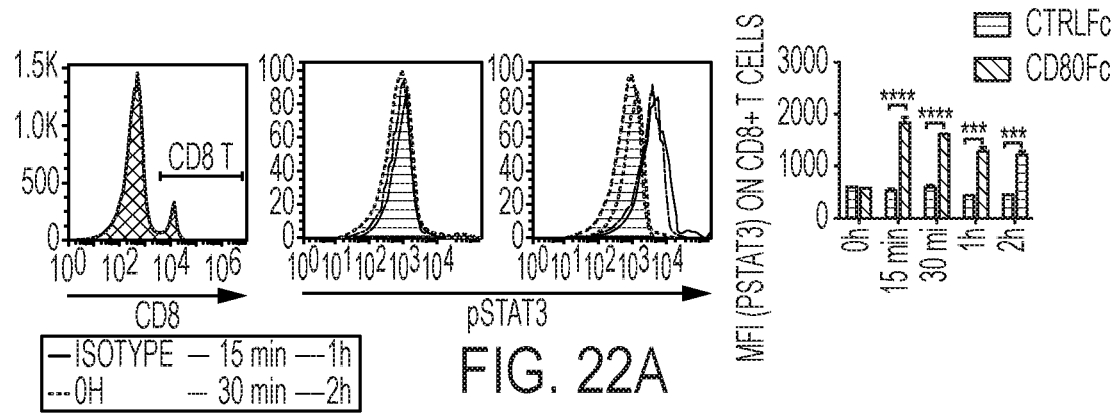
FIGS. 22A-22B: CD80 binding-mediated CD28 activation upregulates pSTAT3 expression on mouse and human $CD8^+$ T cells. (A, B) Mouse splenocytes (A) and human PBMCs (B) were stimulated with anti-CD3 microbeads, treated with control Fc or CD80-Fc for 15 min. 30 min, 1 h or 2 h, and stained for CD8+ and intracellular pSTAT3 for flow cytometric analysis. The median (±SEM) MFI of pSTAT3 expression is shown for the $CD8^+$ T population (n=3). The data are representative of three repeated experiments.
Figure 22B:
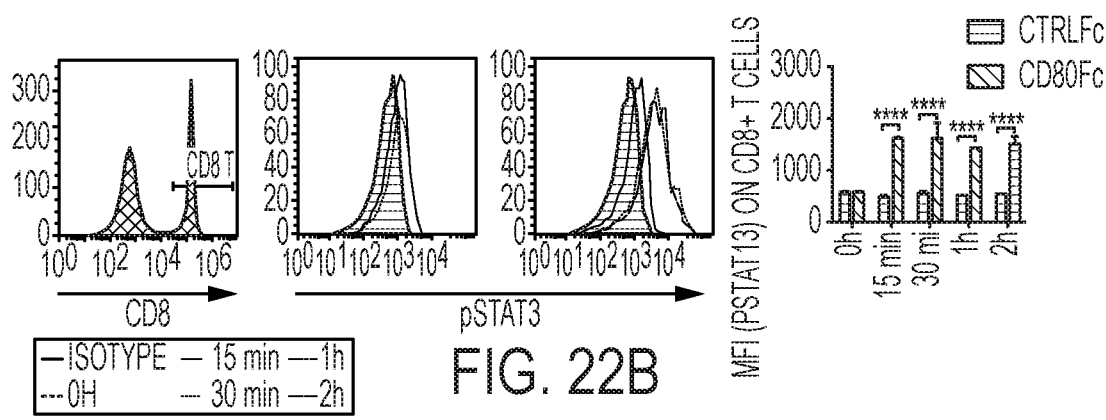
Figure 23:
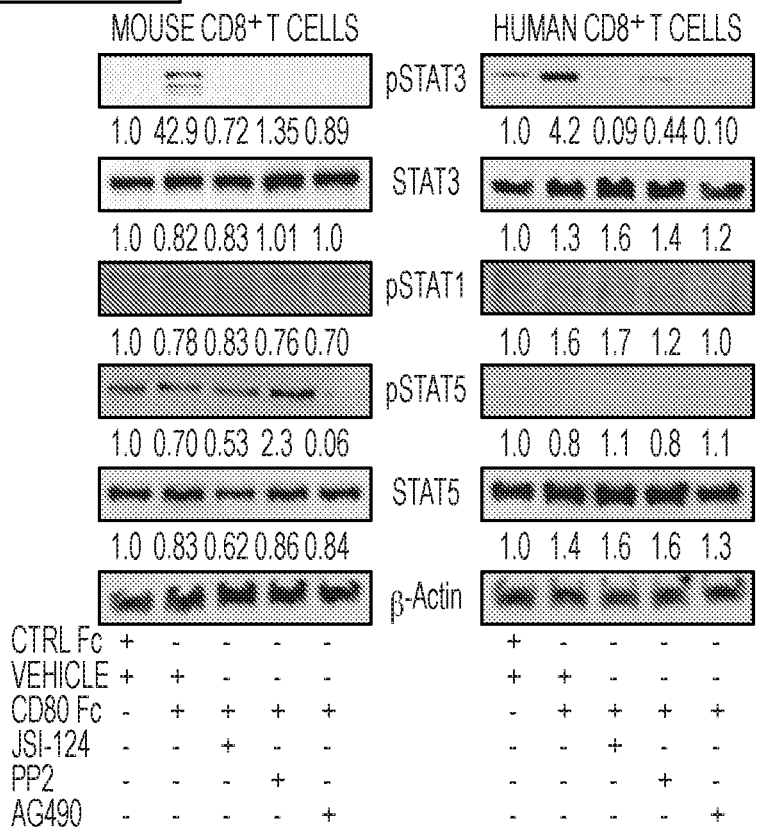
FIG. 23: Elevated STAT3 phosphorylation resulting from CD80 binding-mediated CD28 activation via the tyrosine kinase Lck/JAK/STAT3 signaling pathway. The effect of CD28 activation and treatment with pharmacologic inhibitors on the expression of pSTAT, total STAT, and b-actin according to immunoblot assay. Mouse and human $CD8^+$ T cells were stimulated with anti-CD3 microbeads and treated with ctrl Fc or CD80-Fc in the presence or absence of the pharmacologic inhibitor JSI-124 (0.1 mM), PP2 (1 nM), or AG-490 (50 mM) for 24 h. Vehicle control is included. The intensity quantification shown (intensity of Rae-1/intensity of β-actin) represents the mean intensity from three repeated experiments.
Figure 27:
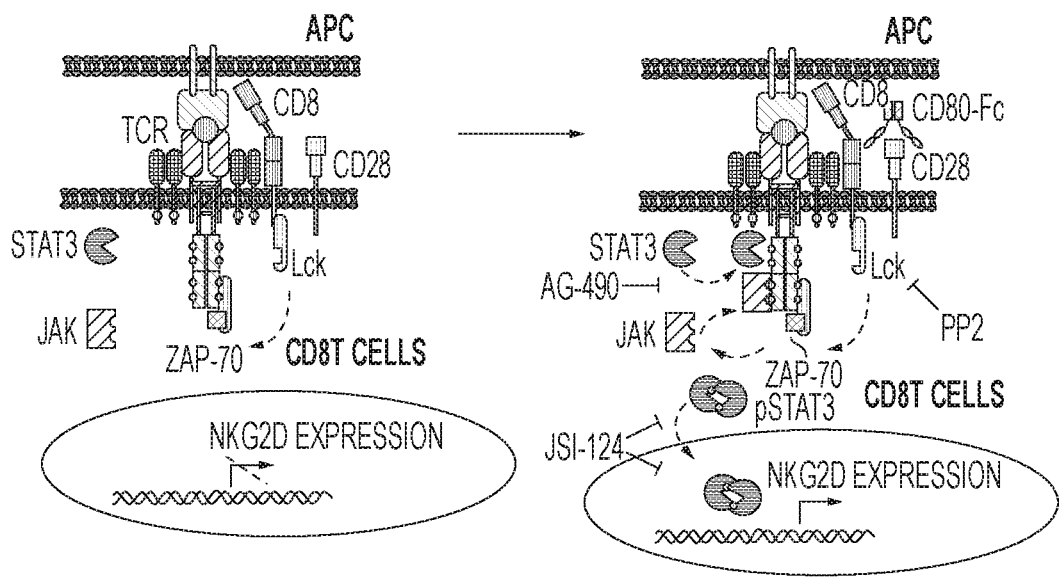
FIG. 27: Schematic of CD80-Fc-induced sustained NKG2D expression on CD8$^+$ T cells. CD80-Fc binding to CD28 can co-stimulate sustained activation of the tyrosine kinase receptor Lck, which triggers a cascade that recruits ZAP70 to amplify the activated Lck-induced signal. JAK/STAT3 is downstream from and activated by ZAP70 and pSTAT3 translocates to the nucleus to induce NKG2D expression.
Figures 29A, 29B:
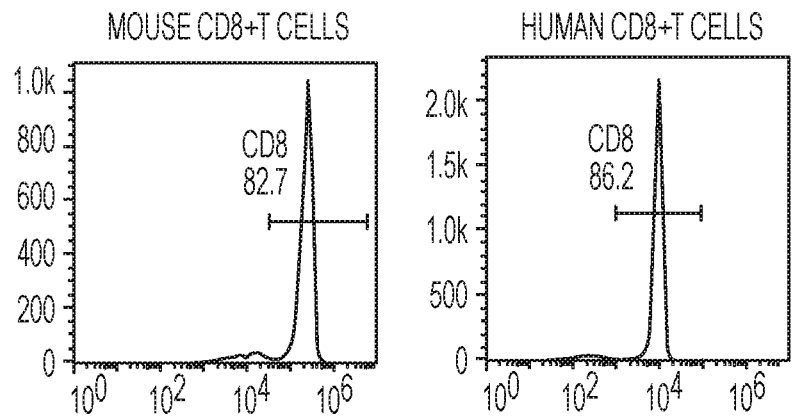
FIGS. 29A-29B: CD8$^+$ T cells were enriched from mouse splenocytes and human PBMCs. The enriched CD8$^+$ T cells were subjected to flow cytometry stained with anti-mouse (A) or human CD8 (B) antibody, respectively to validate the purification efficiency.

STAT3 Phosphorylation by the Lck/ZAP70 Tyrosine Kinase Cascade after CD28 Activation in CD8$^+$ T Cells:

Because NKG2D expression on NK cells is regulated by pSTAT3, the next question was whether pSTAT3 expression is induced in CD8$^+$ T cells by activation of CD28. To address this question, the pSTAT3 expression was measured in both mouse and human CD8$^+$ T cells after incubation with control IgG or CD80-Fc for 15 and 30 min, as well as 1 and 2 h via intracellular flow cytometric staining. Interestingly. CD80-Fc triggered STAT3 phosphorylation (Y705) as early as 15 min, whereas control Fc failed to do so (FIGS. 22A and B). Given that CD28 activation in CD8$^+$ T cells results in STAT3 phosphorylation, it was sought to determine how CD28 activates JAK/STAT3 signaling in CD8$^+$ T cells. In these cells, the co-stimulatory receptor CD28 strengthens TCR signaling via sustained activation of the tyrosine kinase Lck which in turn recruits and activates ZAP70. A previous study demonstrated that CD28 triggers JAK/STAT3 signaling via Lck in CD4C T cells. Thus a pharmacologic model was established to determine whether Lck/ZAP70, as an upstream kinase cascade, activates STAT3 in CD8$^+$ T cells. Mouse and human CD8$^+$ T cells were enriched (FIG. 29) and stimulated with anti-CD3 microbeads and incubated with control IgG or CD80-Fc in the presence or absence of the pharmacologic inhibitor PP2, AG-490, or JSI-124 for 1 h. PP2 was employed because it is a specific Src-family kinase inhibitor sensitive to blockade of Lck activation. Also, AG-490 can inhibit activation of JAK/STAT3 signaling. Furthermore, JSI-124 disrupts JAK/STAT3 activation and pSTAT3 binding to DNA. The immunoblotting results confirmed that STAT3 was activated in CD8$^+$ T cells in response to CD80-Fc-based treatment and that treatment with the pharmacologic inhibitors completed abolished phosphorylation of STAT3. In contrast, the total STAT3 expression level remained similar with the different treatments (FIG. 23), demonstrating that CD28-induced activation of the Src-family tyrosine kinase cascade plays an essential role in STAT3 phosphorylation. Of note, the inhibitors of pSTAT3 may also affect the phosphorylation of other STAT members. To validate the crucial role of pSTAT3, the expression of pSTAT1 and pSTAT5 was also assessed. The results showed that treatment with CD80-Fc failed to affect pSTAT1 and pSTAT5 expression at 1 h.

Figure 30A:
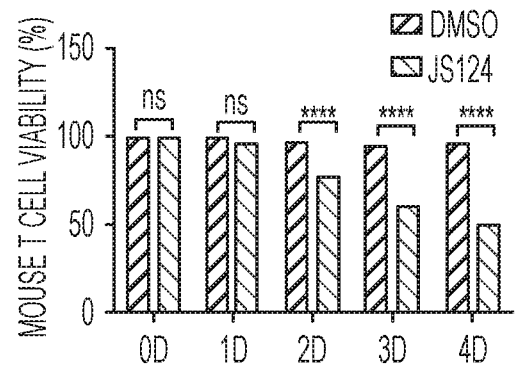
FIGS. 30A-30B: CD8$^+$ T cell viability after JSI-124 treatment. Freshly enriched mouse (A) and human (B) CD8$^+$ T cells were treated with vehicle control or JSI-124 (0.1 µM) for 1, 2, 3, and 4 days. Cell viability was assessed after 7-AAD staining via flow cytometry.
Figure 30B:
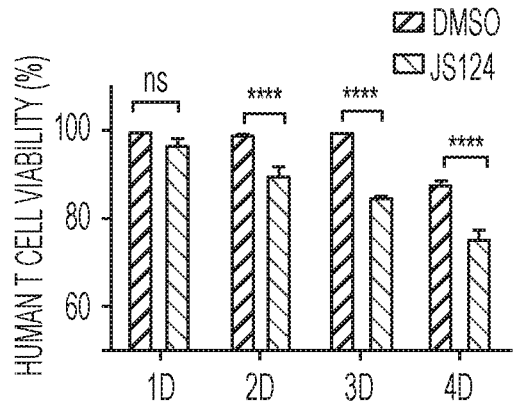

Blockade of STAT3 Activation Disrupts Induction of NKG2D Expression on CD8+ T Cells:

If NKG2D expression is induced by CD80-Fc-based treatment via pSTAT3, inhibition of any upstream activators of STAT3 should abrogate NKG2D induction. A time course study was performed to assess the toxicity of the pharmacologic inhibitors to mouse and human CD8+ T cells. It was noticed that comparing to the vehicle control, cell viability was markedly decreased 48 h after the treatment with JSI-124 (FIG. 30). Therefore, to test the hypothesis, mouse and human CD8+ T cells were enriched and treated with control Fc, CD80-Fc plus control vehicle, or CD80-Fc plus inhibitors of STAT3 activation, including PP2, AG490, and JSI-124, for 24 h. In association with impaired STAT3 activation, treatment with the JAK/STAT3 inhibitors resulted in dramatic decreases in NKG2D expression on CD8+ T cells (FIGS. 24A and B). Overall, these results suggested a biological role for STAT3 in upregulation of NKG2D expression on CD8+ T cells via activation of TCR/CD28 and Lck/JAK tyrosine kinase signaling.

CD28 Activation Stimulates NKG2D-NKG2D Ligand Interaction-Mediated Perforn Production and Antitumor Cytotoxicity:

It was demonstrated that CD28 activation induces NKG2D expression on CD8+ T cells. However, the antitumor cytolytic activity of NKG2D+CD8+ T cells has yet to be evaluated. To assess the function of induced NKG2D expression on CD8+ T cells, mouse CD8+ T cells that were treated with control Fc, CD80-Fc plus sham, or CD80-Fc plus an NKG2D-blocking antibody were co-incubated with NKG2D ligand-positive mouse LLC cells for 5 h. If induced NKG2D expression has effector functions, CD8+ T cells should produce the effector molecule perforin after exposed to NKG2D ligand-positive LLC tumor cells. The concentration of perforin in the medium released from CD8+ T cells was assessed via ELISA, which demonstrated that CD80 stimulation-mediated CD28 activation caused a remarkable increase in perforin production (FIG. 25A). In striking contrast, blockade of NKG2D expression impaired perforin production back to the baseline level, suggesting that increased expression of perforin resulted from NKG2D-NKG2D ligand interaction.

Because increased perforin expression by immune cells often indicates enhanced antitumor cytolytic activity, the cytotoxic T-lymphocyte activity of mouse CD8+ T cells was measured after CD80-Fc-based treatment. Enriched mouse CD8+ T cells were pretreated with control Fc, CD80-Fc plus control IgG, CD80-Fc plus an anti-NKG2D blocking antibody, or CD80-Fc plus the STAT3 inhibitor JSI-124 for 24 h. Also, LLC cells were labeled with CFSE and confirmed with NKG2D ligand Rae-1 expression on the cell surface (FIG. 6B). LLC cells were then incubated with pretreated CD8+ T cells at E:T ratios of 5:1, 10:1, and 25:1 for 5 h. After incubation, the mixed cells were stained with PI (1 mg/mL). Live target cells were identified according to light-scatter parameters and PI negativity. The survival of target cells was determined as the percentage of normalized target cells that remained after incubation with CD8+ T cells. The cytotoxicity of control IgG-treated CD8+ T cells did not increase as the E:T ratio increased. In contrast, CD80-Fc-treated CD8+ T cells exhibited markedly greater killing activity than control Fc-treated CD8+ T cells (FIG. 25C). Consistent with the perforin production in CD8+ T cells described above, blockade of NKG2D expression abrogated CD8+ T-cell mediated cytotoxicity (FIG. 25C). In addition, inhibition of STAT3 activation by JSI-124 impaired the cytolytic activity of CD8+ T cells (FIG. 25C), indicating that expression of NKG2D is associated with the tumor-killing ability of CD8+ T cells.

In a similar manner, the cytolytic activity of human CD8+ T cells was assessed in terms of their degranulation upon CD28 activation. The ability of CD8+ T cells to undergo degranulation was evaluated in response to exposure to target tumor cells by the induction of cell surface marker CD107a. Human CD8+ T cells were enriched from PBMCs, incubated with anti-CD3 microbeads, and treated with control Fc or CD80-Fc in the presence or absence of the STAT3 inhibitor JSI-124 for 24 h. After stimulation, human CD8+ T cells were exposed to CFSE-labeled target NKG2DL+K562 cells at a ratio of 1:1 and co-incubated with an anti-CD107a antibody or isotype control antibody for 4 h. Next, the mixed cells were stained with CD8+ and NKG2D for flow cytometric analysis. The pooled data on three donors' CD8+ T cells demonstrated that without exposure to target cells, stimulated CD8+ T cells had increasing expression of NKG2D but very low levels of degranulation (CD107a). After exposure to target cells, the increased NKG2D expression was associated with enhanced degranulation capacity of cytotoxic CD8+ T cells (FIG. 25D). Conversely, treatment with the STAT3 inhibitor JSI-124 abolished NKG2D expression and, accordingly, reduced degranulation in CD8+ T cells.

Given that ex vivo stimulation with anti-CD3 plus CD80 recombinant protein results in NKG2D induction on CD8+ T cells, this led to wonder whether adoptive transfer of the pre-stimulated CD8+ T cells may improve the therapeutic effects against NKG2D ligand positive tumors. To validate this hypothesis, splenic CD8+ T cells were isolated from Rae-1+LLC tumor bearing mice and stimulated with anti-CD3 plus control Fc or CD80 recombinant protein in the presence or absence of anti-NKG2D antibody for 48 h. The stimulated CD8+ T cells were tested to confirm the induction of NKG2D (FIG. 26A), and then adoptively transferred into LLC tumor bearing mice weekly. Mice were euthanized when the tumors reached 1.5 cm in diameter. The tumors were dissociated and the percentage of tumor infiltrating NKG2D+CD8+ T cells were detected. In agreement with the in vitro results, prestimulation with CD80 greatly enhanced NKG2D+CD8+ T cell population (FIG. 26B) in LLC tumors, whereas blocking NKG2D prior to the CD8+ T cell infusion impaired the CD8+ T cell accumulation in tumors. As a result, the tumor progression was significantly delayed by CD80-stimulated CD8+ T cell therapy in contrast to the control Fc-treated CD8+ T cell therapy (FIG. 26C), and the antitumor effects were completely abolished by blocking NKG2D on the CD8+ T cells. Along with the inhibition of tumor development, CD80 simulated-CD8+ T cell transfer dramatically increased the survival time of tumor bearing mice (FIG. 26C), suggesting that this strategy could benefit for the treatment of NKG2D ligand positive tumors.

Example 4—Materials and Methods

Animals:

Six- to eight-week-old C57BL/6 mice and CD28−/− were purchased from The Jackson Laboratory. The mouse care and handling procedures were approved by the Institutional Animal Care and Use Committee of The University of Texas MD Anderson Cancer Center. To create transplant tumor mouse models, Lewis lung carcinoma (LLC) cells (1.5×10$^5$ per mouse) were inoculated into C57BL/6 mice. Tumor bearing were subject to control DNA (10 mg/mouse), control DNA plus doxorubicin (1 mg/kg), IL-12-encoding DNA (10 mg/mouse), or IL-12-encoding DNA plus doxorubicin, and followed by electroporation as described previously. Tumor volume was calculated by the formula: V D (π/8)£x (a*b$^2$), where V D tumor volume in cubic centimeters, a D maximum tumor diameter, and b=diameter at 90° to a.

Cell Lines:

Buffy coats from de-identified normal blood donors were purchased from the Gulf Coast Regional Blood Center, and their acquisition was approved by the MD Anderson Institutional Review Board. Peripheral blood mononuclear cells (PBMCs) were isolated from buffy coat samples via centrifugation over Ficoll-Paque. Human CD8$^+$ T cells were enriched from PBMCs using an EasySep human CD8$^+$ T-cell isolation kit (STEMCELL Technologies). Human T cells were cultured in 45% RPMI 1640 and 45% Click's medium containing 10% fetal bovine serum. Mouse CD8$^+$ T cells were enriched from splenocytes using an EasySep kit. Mouse T cells were cultured in RPMI 1640 supplemented with 10% fetal bovine serum and 1% penicillin/streptomycin.

Antibodies and Reagents:

Monoclonal antibodies targeting mouse and human CD3, CD8$^+$, and NKG2D as well as isotype control antibodies were purchased from BioLegend. Anti-mouse perforin, human CD107a, and pSTAT3 antibodies were purchased from eBioscience. Anti-human and mouse CD3 microbeads were purchased from Thermo Fisher Scientific. Antibodies targeting pSTAT3 (Tyr705), pSTAT5 (Tyr694) and b-actin were purchased from Cell Signaling Technologies. Antibodies targeting pSTAT1 (Ser727) and total STAT3 were purchased from Santa Cruz Biotechnology. The pharmacologic inhibitors JSI-124, PP2, and AG-490 were purchased from Selleck Chemicals. Human CD80-Fc recombinant protein, human and mouse Fc controls, and human IL-2 were purchased from R&D Systems. Mouse CD80-Fc (Asp37-Lys245-mIgG2a Fc) recombinant protein was synthesized by SYD Labs.

Immunoblotting:

Mouse and human CD8$^+$ T cells were lysed with RIPA buffer. The protein extract was separated from cell debris via centrifugation at a maximum speed for 20 min at 4° C. Twenty micrograms of total protein was separated via 10% sodium dodecyl sulfate-polyacrylamide gel electrophoresis and transferred to nitrocellulose membranes using an iBlot gel transfer device (Invitrogen). The membranes were blotted with different primary and secondary antibodies to detect the proteins of interest.

Flow Cytometry:

Cells were sequentially incubated with primary and secondary antibodies for 30 min each at 4° C. Stained cells were analyzed using an Attune acoustic focusing cytometer (Applied Biosystems). Flow cytometry data were analyzed using the FlowJo software program (BD Biosciences).

Degranulation Assay:

Human CD8$^+$ T cells were treated with control Fc or CD80-Fc (1 mg/mL) in the presence or absence of 0.1 mM JSI-124, 1 nM PP2, or 50 mM AG-490. Cells were then co-incubated with target cells at a ratio of 1:1 (E:T) at 37° C. for 4 h, and anti-CD107a (LAMP1) or isotype control antibodies were added cell mixture during the co-incubation. Cells were stained with an anti-NKG2D antibody for flow cytometric analysis.

Cytotoxic T-Lymphocyte Assay:

LLC cells were labeled with 500 mM carboxyfluorescein succinimidyl ester (CFSE; Invitrogen) and incubated for 5 h at 37° C. together with purified mouse CD8$^+$ T cells at ratios of 5:1, 10:1, and 25:1 (E:T). After incubation, the cells were stained with propidium iodide (PI; 1 mg/mL [Sigma Aldrich]). Live target cells were identified according to light-scatter parameters and PI negativity. Survival of the target cells was measured as the percentage of normalized target cells that remained after incubation with CD8$^+$ T cells.

ELISA:

The levels of mouse perforin in cell culture medium were measured using mouse perforin ELISA kit from BioSource.

Statistical Analysis:

The directly measured outcomes were analyzed using a two-sided Student t-test to compare two treatment groups or one-way ANOVA analysis of variance to compare more than two treatment groups. The statistical significance of each comparison was determined using the GraphPad Prism software program (GraphPad Software). p values less than 0.05 indicated statistical significance. *p<0.05; p<0.01; *p<0.005; ****p<0.001; ns, no statistical significance.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Anderson, *Science* 256:808-813, 1992.
Austin-Ward and Villaseca, *Revista Medica de Chile*, 126 (7):838-845, 1998.
Ausubel et al., *Current Protocols in Molecular Biology*, Greene Publishing Associates and John Wiley & Sons, N Y, 1994.
Besser et al. *Clin Cancer Res.* 16(9):2646-55, 2010.
Bukowski et al., *Clinical Cancer Res.*, 4(10):2337-2347, 1998.
Camacho et al. *J Clin Oncology* 22(145): Abstract No. 2505, 2004.
Carter et al., *Cancer J.* 14(3):154-69, 2008.
Chothia et al., *EMBO J.* 7:3745, 1988.
Christodoulides et al., *Microbiology*, 144(Pt 11):3027-3037, 1998.
Cohen et al. *J Immunol.* 175:5799-5808, 2005.
Cutrera et al., *Molecular therapy: the journal of the American Society of Gene Therapy*, 19(8):1468-77, 2011.
Czerkinsky et al., *J. Immunol. Methods* 1988; 110:29-36.
Davidson et al., *J. Immunother.*, 21(5):389-398, 1998.
Davila et al. *PLoS ONE* 8(4): e61338, 2013.
Dillon. *TIBTECH* 11:167-175, 1993.
Dudley et al. *Clinical Oncology.* 23(10):2346-57.2005.
European patent application number EP2537416
European Patent Publication No. EP957359

Fedorov et al., *Sci. Transl. Medicine*, 5(215), 2013.
Haddada et al., in Current Topics in Microbiology and Immunology, 1995.
Hanibuchi et al., *Int. J. Cancer*, 78(4):480-485, 1998.
Heemskerk et al. *Hum Gene Ther.* 19:496-510, 2008.
Hellstrand et al., *Acta Oncologica*, 37(4):347-353, 1998.
Hollander, *Front. Immun.*, 3:3, 2012.
Hui and Hashimoto, *Infection Immun.*, 66(11):5329-5336, 1998.
Hurwitz et al. *Proc Natl Acad Sci USA* 95(17): 10067-10071, 1998.
International Patent Publication No. WO 00/37504
International Patent Publication No. WO 01/14424
International Patent Publication No. WO 91116024
International Patent Publication No. WO 91117424
International Patent Publication No. WO 98/42752
International Patent Publication No. WO/201405566
International Patent Publication No. WO1995001994
International Patent Publication No. WO1998042752
International Patent Publication No. WO2000037504
International Patent Publication No. WO200014257
International Patent Publication No. WO2001014424
International Patent Publication No. WO2007/103009
International Patent Publication No. WO2012/129514
International Patent Publication No. WO2013/071154
International Patent Publication No. WO2013/123061
International Patent Publication No. WO2013/166321
International Patent Publication No. WO2013126726
International Patent Publication No. WO2014/055668
International Patent Publication No. WO2014031687
International Patent Publication No. WO2015016718
International Patent Publication No. WOO 1/14424
Janeway et al. Immunobiology: The Immune System in Health and Disease, 3 rd Ed., Current Biology Publications, p. 4:33, 1997.
Johnson et al. *Blood* 114:535-46, 2009.
Jores et al., *PNAS U.S.A.* 87:9138, 1990.
Kozma et al., *Nucleic Acids Research* 41 Database Issue, D524-D529, 2013.
Kremer & Perricaudet, *British Medical Bulletin* 51(1):31-44, 1995.
Kyte and Doolittle, *J. Mol. Biol.* 157:105-132, 1982.
Leal et al., *Ann N Y Acad Sci.* 2014; 1321:41-54, 2014.
Lefranc et al., *Dev. Comp. Immunol.* 27:55, 2003.
Li *Nat Biotechnol.* 23:349-354, 2005.
Mellman et al., *Nature* 480:480-48, 2011.
Miller, *Nature* 357:455-460, 1992.
Mitani & Caskey, *TIBTECH* 11:162-166, 1993.
Mokyr et al. *Cancer Res* 58:5301-5304, 1998.
Nabel & Feigner, *TIBTECH* 11:211-217, 1993.
Olsson et al. *J. Clin. Invest.* 1990; 86:981-985.
Pardoll *Nat Rev Cancer,* 12(4): 252-64, 2012.
Parkhurst et al. *Clin Cancer Res.* 15: 169-180, 2009.
Qin et al., *Proc. Natl. Acad. Sci. USA,* 95(24):14411-14416, 1998.
Radvanyi et al. *Clin Cancer Res.* 18(24):6758-70.2012.
Sadelain et al., *Cancer Discov.* 3(4): 388-398, 2013.
Sambrook et al., *Molecular Cloning: A Laboratory Manual,* 3rd ed., Cold Spring Harbor Press, Cold Spring Harbor, N.Y. 2001.
Teicher B A. *Current cancer drug targets.* 9(8):982-1004, 2009.
Teicher B A. *Current opinion in oncology.* 26(5):476-83, 2014.
Terakura et al. *Blood.* 1:72-82, 2012.
Turtle et al., *Curr. Opin. Immunol.,* 24(5): 633-39.2012.
U.S. Pat. No. 4,870,287
U.S. Pat. No. 4,897,355
U.S. Pat. No. 4,946,787
U.S. Pat. No. 5,049,386
U.S. Pat. No. 5,739,169
U.S. Pat. No. 5,760,395
U.S. Pat. No. 5,801,005
U.S. Pat. No. 5,824,311
U.S. Pat. No. 5,830,880
U.S. Pat. No. 5,844,905
U.S. Pat. No. 5,846,945
U.S. Pat. No. 5,885,796
U.S. Pat. No. 5,939,281
U.S. Pat. No. 6,207,156
U.S. Pat. No. 6,218,132
U.S. Pat. No. 6,225,042
U.S. Pat. No. 6,355,479
U.S. Pat. No. 6,362,001
U.S. Pat. No. 6,410,319
U.S. Pat. No. 6,451,995
U.S. Pat. No. 6,790,662
U.S. Pat. No. 7,070,995
U.S. Pat. No. 7,265,209
U.S. Pat. No. 7,354,762
U.S. Pat. No. 7,446,179
U.S. Pat. No. 7,446,190
U.S. Pat. No. 7,446,191
U.S. Pat. No. 8,008,449
U.S. Pat. No. 8,017,114
U.S. Pat. No. 8,119,129
U.S. Pat. No. 8,252,592
U.S. Pat. No. 8,324,353
U.S. Pat. No. 8,329,867
U.S. Pat. No. 8,339,645
U.S. Pat. No. 8,354,509
U.S. Pat. No. 8,398,282
U.S. Pat. No. 8,479,118
U.S. Pat. No. 8,735,553
U.S. Patent Publication No. 2005/0260186
U.S. Patent Publication No. 2006/0104968
U.S. Patent Publication No. 2009/0004142
U.S. Patent Publication No. 2009/0017000
U.S. Patent Publication No. US2002131960
U.S. Patent Publication No. US20110008369
U.S. Patent Publication No. US20130149337
U.S. Patent Publication No. US2013287748
U.S. Patent Publication No. US2014022021
U.S. Patent Publication No. US20140294898
Van Brunt, *Biotechnology* 6(10):1149-1154, 1988.
Varela-Rohena et al. *Nat Med.* 14: 1390-1395, 2008.
Vigne, Restorative Neurology and Neuroscience 8:35-36, 1995.
Wang et al. *J Immunother.* 35(9):689-701, 2012.
Wu et al., *Cancer,* 18(2): 160-75, 2012.
Yu et al. *Gene Therapy* 1:13-26, 1994.

What is claimed is:

1. A nucleic acid encoding a membrane-anchored interleukin 12 (IL-12) heterodimer protein composed of a first and second polypeptide, the nucleic acid comprising:
   a) a first nucleic acid encoding a first polypeptide comprising an IL-12 alpha subunit p35 or a polypeptide at least 90% similar thereto fused to a transmembrane domain; and
   b) a second nucleic acid encoding a second polypeptide comprising an IL-12 beta subunit p40 or a polypeptide at least 90% similar thereto wherein the first nucleic acid and second nucleic acids are under the control of separate promoters.

2. The nucleic acid of claim 1, further comprising a sequence encoding a linker between the first polypeptide and the transmembrane domain.

3. The nucleic acid of claim 1, wherein the first polypeptide comprises an amino acid sequence at least 90% similar to SEQ ID NO:1.

4. The nucleic acid of claim 1, wherein the second polypeptide comprises an amino acid sequence at least 90% similar to SEQ ID NO:4.

5. An expression vector comprising the nucleic acid of claim 1.

6. The expression vector of claim 5, wherein the expression vector is a viral vector.

7. The expression vector of claim 6, wherein the viral vector is further defined as a lentiviral vector, retroviral vector, adenoviral vector, or adeno-associated viral vector.

8. A population of T cells engineered to express a nucleic acid encoding a membrane-anchored IL-12 heterodimer according to claim 1.

9. A method for producing the population of T cells of claim 8 comprising obtaining a starting population of T cells and introducing a vector expressing membrane-anchored IL-12, thereby generating a population of T cells expressing membrane-anchored IL-12.

10. A method of treating a cancer in a subject comprising administering an effective amount of T cells engineered to express the nucleic acid encoding the heterodimer membrane-anchored IL-12 of claim 1 to the subject.

11. The method of claim 10, wherein administration of the T cells expressing membrane-anchored IL-12 does not induce IFNγ or induces a lower level of IFNγ as compared to administration of T cells with wild-type IL-12.

12. The method of claim 11, wherein the IFNγ is measured in a serum sample.

13. The method of claim 10, wherein administering the T cells induces expression of CXCL9, CXCL10 and/or CCL17.

14. The method of claim 10, wherein administering the T cells induces expression of NKG2D and/or NKG2D ligands.

15. The method of claim 10, wherein the nucleic acid further comprises a sequence encoding a tumor-targeting component fused to the second polypeptide.

16. The method of claim 10, wherein the nucleic acid encoding the membrane-anchored IL-12 further comprises sequence encoding a linker between the first polypeptide and the transmembrane domain.

17. The method of claim 10, wherein the first polypeptide comprises an amino acid sequence at least 90% similar to SEQ ID NO:1.

18. The method of claim 10, wherein the second polypeptide comprises an amino acid sequence at least 90% similar to SEQ ID NO:4.

19. The method of claim 16, wherein the transmembrane domain comprises the amino acid sequence of SEQ ID NO:3.

20. The method of claim 16, wherein the linker comprises the amino acid sequence GGGGSGGGGSS (SEQ ID NO:5).

21. The method of claim 10, wherein the T cells are CD8+ T cells.

22. The method of claim 10, wherein the T cells are further engineered to express chimeric antigen receptor (CAR) having antigenic specificity for a tumor-associated antigen.

23. The method of claim 10, wherein the T cells are activated with anti-CD3 and CD80-Fc recombinant protein.

24. The method of claim 10, wherein the T cells are autologous T cells.

25. The method of claim 10, wherein the T cells are engineered to express membrane-anchored IL-12 by lentiviral transduction.

26. The method of claim 25, wherein there is low or essentially no T cell accumulation in the subject's lungs after administering the T cells engineered to express membrane-anchored IL-12.

27. The method of claim 10, wherein the method further comprises administering at least one additional therapeutic agent.

28. The method of claim 10, wherein the at least one additional therapeutic agent is chemotherapy.

29. The method of claim 10, wherein the cancer is colon cancer or lung cancer.

30. The method of claim 10, wherein administering the T cells induces expression of co stimulatory receptor CD28 and/or CD80.

31. The method of claim 10, wherein administering the T cells decreases expression of an immune checkpoint inhibitor.

32. The method of claim 31, wherein the immune checkpoint inhibitor is PD-1 or PD-L1.

33. The method of claim 15, wherein the T cells penetrate to or near the center of a tumor within the subject.

34. The method of claim 25, wherein lentiviral transduction results in a reduced risk of cytokine response syndrome (CRS), reduced systemic toxicity, and/or increased effectiveness of treatment.

* * * * *